US011053507B2

(12) United States Patent
Tian et al.

(10) Patent No.: US 11,053,507 B2
(45) Date of Patent: *Jul. 6, 2021

(54) CURING FOR RECURSIVE NUCLEIC ACID-GUIDED CELL EDITING

(71) Applicant: Inscripta, Inc., Boulder, CO (US)

(72) Inventors: Tian Tian, Boulder, CO (US); Charles Johnson, Boulder, CO (US); Eileen Spindler, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/072,023

(22) Filed: Oct. 15, 2020

(65) Prior Publication Data

US 2021/0040489 A1  Feb. 11, 2021

Related U.S. Application Data

(63) Continuation of application No. 16/892,679, filed on Jun. 4, 2020, now Pat. No. 10,837,021.

(60) Provisional application No. 62/857,967, filed on Jun. 6, 2019.

(51) Int. Cl.
*C12N 15/70* (2006.01)
*C12N 15/113* (2010.01)
*C12N 9/22* (2006.01)

(52) U.S. Cl.
CPC .............. *C12N 15/70* (2013.01); *C12N 9/22* (2013.01); *C12N 15/113* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 6,391,582 B2 | 5/2002 | Ying et al. | |
| 6,837,995 B1 | 1/2005 | Vassarotti et al. | |
| 7,166,443 B2 | 1/2007 | Walker et al. | |
| 8,332,160 B1 | 12/2012 | Platt et al. | |
| 8,697,359 B1 | 4/2014 | Zhang et al. | |
| 8,926,977 B2 | 1/2015 | Miller et al. | |
| 9,260,505 B2 | 2/2016 | Weir et al. | |
| 9,361,427 B2 | 6/2016 | Hillson | |
| 9,499,855 B2 | 11/2016 | Newbold et al. | |
| 9,776,138 B2 | 10/2017 | Innings et al. | |
| 9,790,490 B2 | 10/2017 | Zhang et al. | |
| 9,896,696 B2 | 2/2018 | Begemann et al. | |
| 9,982,279 B1 | 5/2018 | Gill et al. | |
| 9,988,624 B2 | 6/2018 | Serber et al. | |
| 10,011,849 B1 | 7/2018 | Gill et al. | |
| 10,017,760 B2 | 7/2018 | Gill et al. | |
| 10,266,851 B2 | 4/2019 | Chen | |
| 10,837,021 B1 * | 11/2020 | Tian | C12N 15/113 |
| 2002/0139741 A1 | 10/2002 | Kopf | |
| 2004/0110253 A1 | 6/2004 | Kappler et al. | |
| 2010/0076057 A1 | 3/2010 | Sontheimer et al. | |
| 2014/0068797 A1 | 3/2014 | Doudna et al. | |
| 2014/0199767 A1 | 7/2014 | Barrangou et al. | |
| 2014/0273226 A1 | 9/2014 | Wu et al. | |
| 2015/0098954 A1 | 4/2015 | Hyde et al. | |
| 2015/0159174 A1 | 6/2015 | Frendewey et al. | |
| 2015/0176013 A1 | 6/2015 | Musunuru et al. | |
| 2015/0191719 A1 | 7/2015 | Hudson et al. | |
| 2015/0225732 A1 | 8/2015 | Williams et al. | |
| 2016/0024529 A1 | 1/2016 | Carstens et al. | |
| 2016/0053272 A1 | 2/2016 | Wurtzel et al. | |
| 2016/0053304 A1 | 2/2016 | Wurtzel et al. | |
| 2016/0076093 A1 | 3/2016 | Shendure et al. | |
| 2016/0102322 A1 | 4/2016 | Ravinder et al. | |
| 2016/0168592 A1 | 6/2016 | Church et al. | |
| 2016/0281053 A1 | 9/2016 | Sorek et al. | |
| 2016/0289673 A1 | 10/2016 | Huang et al. | |
| 2016/0298134 A1 | 10/2016 | Chen et al. | |
| 2016/0354487 A1 | 12/2016 | Zhang et al. | |
| 2017/0002339 A1 | 1/2017 | Barrangou et al. | |
| 2017/0022499 A1 | 1/2017 | Lu et al. | |
| 2017/0051310 A1 | 2/2017 | Doudna et al. | |
| 2017/0073705 A1 | 3/2017 | Chen et al. | |
| 2017/0191123 A1 | 7/2017 | Kim et al. | |
| 2017/0211078 A1 | 7/2017 | Kamineni et al. | |
| 2017/0240922 A1 | 8/2017 | Gill et al. | |
| 2017/0369870 A1 | 12/2017 | Gill et al. | |
| 2018/0028567 A1 | 2/2018 | Li et al. | |
| 2018/0052176 A1 | 2/2018 | Holt et al. | |
| 2018/0073013 A1 | 3/2018 | Lorenz et al. | |
| 2018/0112235 A1 | 4/2018 | Li et al. | |

(Continued)

FOREIGN PATENT DOCUMENTS

| | | |
|---|---|---|
| EP | 2395087 | 12/2011 |
| EP | 3199632 | 8/2017 |

(Continued)

OTHER PUBLICATIONS

International Search Report and Written Opinion for International Application No. PCT/US20/19379, dated Jul. 22, 2020, p. 1-10.
International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
Bao, et al., "Genome-scale engineering of Saccharomyces cerevisiae with single-nucleotide precision", Nature Biotechnology, doi:10.1038/nbt.4132, pp. 1-6 (May 7, 2018).

(Continued)

*Primary Examiner* — Nancy J Leith
(74) *Attorney, Agent, or Firm* — Sarah Brashears; Dianna L. De Vore

(57) ABSTRACT

The present disclosure provides automated multi-module instrumentation and automated methods for performing recursive editing of live cells with curing of editing vectors from prior rounds of editing.

20 Claims, 40 Drawing Sheets

(56) References Cited

U.S. PATENT DOCUMENTS

| | | |
|---|---|---|
| 2018/0200342 A1 | 7/2018 | Bikard et al. |
| 2018/0230460 A1 | 8/2018 | Gill et al. |
| 2019/0017072 A1 | 1/2019 | Ditommaso et al. |
| 2019/0169605 A1 | 6/2019 | Masquelier et al. |

FOREIGN PATENT DOCUMENTS

| | | | |
|---|---|---|---|
| WO | WO2002/010183 | 2/2002 | |
| WO | WO 2003/087341 | 10/2003 | |
| WO | WO 2010/079430 | 7/2010 | |
| WO | WO 2011/072246 | 6/2011 | |
| WO | WO 2011/143124 | 11/2011 | |
| WO | WO 2013/142578 | 9/2013 | |
| WO | WO 2013/176772 | 11/2013 | |
| WO | WO 2014/018423 | 1/2014 | |
| WO | WO 2014/143381 A1 * | 9/2014 | ............... C12N 9/22 |
| WO | WO 2014/144495 | 9/2014 | |
| WO | WO 2016/110453 | 7/2016 | |
| WO | WO 2017/053902 | 3/2017 | |
| WO | WO 2017/078631 | 5/2017 | |
| WO | WO 2017/083722 | 5/2017 | |
| WO | WO 2017/106414 | 6/2017 | |
| WO | WO 2017/161371 | 9/2017 | |
| WO | WO 2017/174329 | 10/2017 | |
| WO | WO 2017/186718 | 11/2017 | |
| WO | WO 2017/216392 | 12/2017 | |
| WO | WO 2017/223330 | 12/2017 | |
| WO | WO 2018/031950 | 2/2018 | |
| WO | WO 2018/071672 | 4/2018 | |
| WO | WO 2018/083339 | 5/2018 | |
| WO | WO 2018/191715 | 10/2018 | |
| WO | WO2019/006436 | 1/2019 | |

OTHER PUBLICATIONS

Dicarlo, et al., "Genome engineering in Saccharomyces cervisiae using CRISPR-Case systems", Nucleic Acids Research, 41(7):4336-43 (2013).

Garst, et al., "Genome-wide mapping of mutations at single-nucleotide resolution for protein, metabolic and genome engineering", Nature Biotechnology, 35(1):48-59 (2017).

Hsu, et al., "DNA targeting specificity of RNA-guided Cas9 nucleases", Nature Biotechnology, 31(9):827-32 (2013).

Jiang, et al., "RNA-guided editing of bacterial genomes using CRISPR-Cas systems", Nature Biotechnology, 31(3):233-41 (2013).

Jinek, et al., "A Programmable Dual-RNA-Guided DNA Endonuclease in Adaptive Bacterial Immunity", Science, 337:816-20 (2012).

Verwaal, et al., "CRISPR/Cpfl enables fast and simple genome editing of Saccharamyces cerevisiae", Yeast, 35:201-11 (2018).

Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).

Roy, et cl., "Multiplexed precision genome editing with trackable genomic barcodes in yeast", Nature Biotechnolgy, doi:10.1038/nbt.4137, pp. 1-16 (2018).

Dong, "Establishment of a highly efficient virus-inducible CRISPR/Cas9 system in insect cells," Antiviral Res., 130:50-7(2016).

Epinat et al., "A novel engineered meganuclease induces homologous recombination in eukaryotic cells, e.g., yeast and mammalian cells", Nucleic Acids Research, 31(11): 2952-2962 2003.

Farasat et al., "A Biophysical Model of CRISPR/Cas9 Activity for Rational Design of Genome Editing and Gene Regulation," PLoS Comput Biol., 29:12(1):e1004724 (2016).

Liu et al., "A chemical-inducible CRISPR-Cas9 system for rapid control of genome editing", Nature Chemical Biology, 12:980-987(2016).

Eklund, et al., "Altered target site specificity variants of the I-Ppol His-Cys bis homing endonuclease" Nucleic Acids Research, 35(17):5839-50 (2007).

Boles, et al., "Digital-to-biological converter for on-demand production of biologics", Nature Biotechnology, doi:10.1038/nbt.3859 (May 29, 2017).

Pines, et al., "Codon Compression Algorithms for Saturation Mutagenesis", ACS Synthetic Biology, 4:604-14 (2015).

Bessa et al., "Improved gap repair cloning in yeast: treatment of the gapped vector with Taq DNA polymerase avoids vector self-ligation," Yeast, 29(10):419-23 (2012).

Boch, "TALEs of genome targeting," Nature Biotechnology vol. 29, pp. 135-136 (2011).

Campbell et al., "Targeting protein function: the expanding toolkit for conditional disruption," Biochem J., 473(17):2573-2589 (2016).

Casini et al., "Bricks and blueprints: methods and standards for DNA assembly," Nat Rev Mol Cell Biol., (9):568-76 (2015).

Chica et al., "Semi-rational approaches to engineering enzyme activity: combining the benefits of directed evolution and rational design," Current Opinion in Biotechnology, 16(4): 378-384 (2005).

Durai et al., "Zinc finger nucleases: custom-designed molecular scissors for genome engineering of plant and mammalian cells", Nucleic Acids Res., 33(18):5978-90 (2005).

Kadonaga et al., "Regulation of RNA polymerase II transcription by sequence-specific DNA binding factors", Cell, 116(2):247-57 (2004).

Lee et al., "Targeted chromosomal deletions in human cells using zinc finger nucleases", Genome. Res., 20 (1): 81-9 (2009).

Miller et al., "A TALE nuclease architecture for efficient genome editing", Nature Biotechnology, 29 (2): 143-8 (2011).

Mittelman et al., "Zinc-finger directed double-strand breaks within CAG repeat tracts promote repeat instability in human cells", PNAS USA, 106 (24): 9607-12 (2009).

Shivange, "Advances in generating functional diversity for directed protein evolution", Current Opinion in Chemical Biology, 13 (1): 19-25 (2009).

Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).

Urnov et al., "Genome editing with engineered zinc finger nucleases", Nature Reviews Genetics, 11:636-646 (2010).

International Search Report and Written Opinion for International Application No. PCT/US2018/053608, dated Dec. 13, 2018, p. 1-9.

International Search Report and Written Opinion for International Application No. PCT/US2018/053670, dated Jan. 3, 2019, p. 1-13.

International Search Report and Written Opinion for International Application No. PCT/US2018/053671, dated Sep. 26, 2018, p. 1-12.

International Search Report and Written Opinion for International Application No. PCT/US2018/040519, dated Sep. 26, 2018, p. 1-8.

International Search Report and Written Opinion for International Application No. PCT/US2019/026836, dated Jul. 2, 2019, p. 1-10.

International Search Report and Written Opinion for International Application No. PCT/US2019/023342, dated Jun. 6, 2019, p. 1-34.

International Search Report and Written Opinion for International Application No. PCT/US2019/030085, dated Jul. 23, 2019, p. 1-14.

International Search Report and Written Opinion for International Application No. PCT/US20/24341, dated Jun. 19, 2020, p. 1-9.

NonFinal Office Action for U.S. Appl. No. 16/399,988, dated Jul. 31, 2019, p. 1-20.

First Office Action Interview Pilot Program Pre-Interview Communication for U.S. Appl. No. 16/024,831, dated Feb. 12, 2019, p. 1-37.

NonFinal Office Action for U.S. Appl. No. 16/024,816 dated Sep. 4, 2018, p. 1-10.

Final Office Action for U.S. Appl. No. 16/024,816 dated Nov. 26, 2018, p. 1-12.

First Office Action Interview Pilot Program Pre-Interview Communication Preinterview for U.S. Appl. No. 16/454,865 dated Aug. 16, 2019, p. 1-36

Yoshioka, et al., "Development of a mono-promoter-driven CRISPR/Cas9 system in mammalian cells", Scientific Reports, Jul. 3, 2015, p. 1-8.

Remaut, et al., "Plasmid vectors for high-efficiency expression controlled by the PL promoter of coliphage lambda," Laboratory of Molecular Biology, Apr. 15, 1981, p. 81-93.

(56) References Cited

OTHER PUBLICATIONS

International Search Report and Written Opinion for International Application No. PCT/US2019/028821, dated Aug. 2, 2019, p. 1-14
International Search Report and Written Opinion for International Application No. PCT/US2019/028883, dated Aug. 16, 2019, p. 1-12
International Search Report and Written Opinion for International Application No. PCT/US2019/46526, dated Dec. 18, 2019, p. 1-17
International Search Report and Written Opinion for International Application No. PCT/US2018/34779, dated Nov. 26, 2018, p. 1-39
International Search Report and Written Opinion for International Application No. PCT/US19/57250, dated Feb. 25, 2020, p. 1-16
International Search Report and Written Opinion for International Application No. PCT/US19/47135, dated Jun. 11, 2020, p. 1-15.

* cited by examiner

ENGINE CURING

SELF - CURING

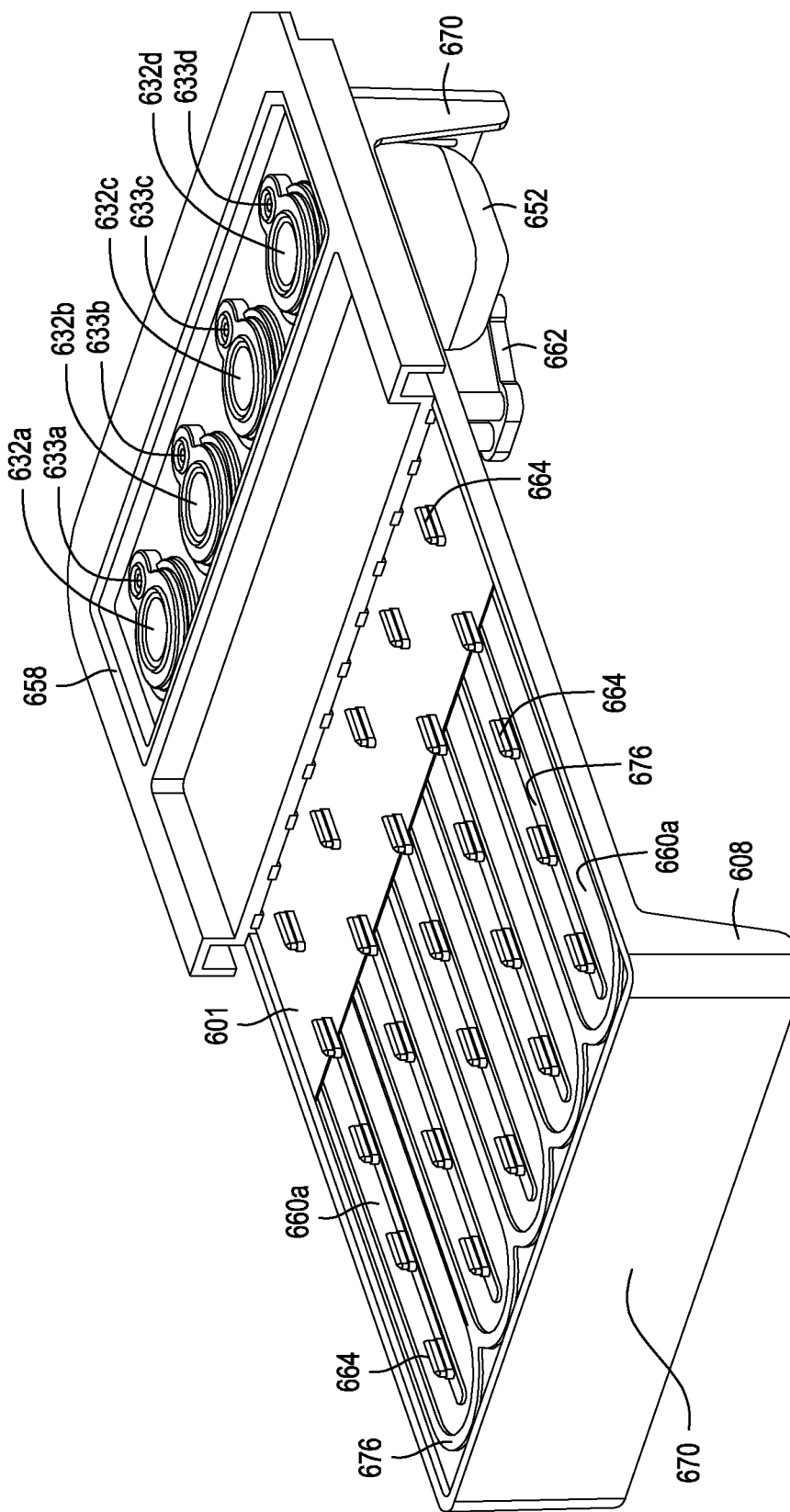

CURING FOR RECURSIVE NUCLEIC ACID-GUIDED CELL EDITING

RELATED CASES

The present application is a continuation of U.S. Ser. No. 16/892,967, entitled "Curing for Recursive Nucleic Acid-Guided Cell Editing", filed 5 Jun. 2020, now U.S. Pat. No. 10,837,021; which claims priority to U.S. Ser. No. 62/857,967, entitled "Curing for Recursive Nucleic Acid-Guided Cell Editing", filed 6 Jun. 2019.

FIELD OF THE INVENTION

The present disclosure relates to automated multi-module instruments, compositions and methods for performing recursive genomic editing technologies.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The ability to make precise, targeted changes to the genome of living cells has been a long-standing goal in biomedical research and development. Recently, various nucleases have been identified that allow for manipulation of gene sequences, and hence gene function. The nucleases include nucleic acid-guided nucleases and nuclease fusions, which enable researchers to generate permanent edits in live cells. It is desirable to be able to perform two to many rounds of nucleic acid-guided nuclease editing sequentially (e.g., perform recursive editing), but in doing so it is also desirable to clear or "cure" a prior editing nucleic acid from the cells before transforming or transfecting the cells with a subsequent editing nucleic acid. Curing is a way to eliminate the prior editing vector including the attendant gRNA and donor DNA sequences editing or CREATE cassette) contained on an editing vector and also selection genes and other sequences contained on the editing vector. Further, eliminating the editing vector from a prior round of editing permits a new editing vector to propagate within a cell without competition from the prior editing vector.

There is thus a need in the art of nucleic acid-guided nuclease gene editing for improved methods, compositions, modules and instruments for curing editing vectors used in prior rounds of editing. The present invention satisfies this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides compositions, automated methods and multi-module automated instrumentation for performing curing of editing vectors in recursive editing protocols.

Thus, in some embodiments there is provided a method for curing cells during recursive nucleic acid-directed nuclease editing comprising: designing and synthesizing sets of editing cassettes, wherein the sets of editing cassettes comprise one or more editing gRNA and donor DNA pairs wherein each editing gRNA and donor DNA pair is under the control of a first inducible promoter; assembling the editing cassettes into a vector backbone thereby forming editing vectors, wherein the vector backbone comprises a first selectable marker, and a curing target sequence; making cells of choice electrocompetent, wherein the cells of choice comprise an engine vector and the engine vector comprises a curing gRNA under the control of a second inducible promoter, a nuclease under the control of the third inducible promoter; and a second selectable marker; transforming the cells of choice with a first set editing vectors to produce transformed cells; selecting for transformed cells via the first and second selectable markers; inducing editing in the selected cells by inducing the first and third inducible promoters thereby inducing transcription of the one or more editing gRNA and donor DNA pairs and the nuclease; growing the cells until the cells reach a stationary phase of growth; curing the editing vector by inducing the third and second inducible promoters thereby inducing transcription of the nuclease and curing gRNA; growing the cells; rendering the cells electrocompetent; and transforming the cells with a second set of the editing vectors to produce second transformed cells, wherein the second set of editing vectors comprises editing cassettes with one or more gRNA and donor DNA pairs under the control of the first inducible promoter, a third selectable marker, and the curing target sequence.

In some aspects of this embodiment, the first inducible promoter and the third inducible promoters are the same inducible promoter, and in some aspects, the first and third inducible promoters are pL promoters and either the editing vector or the engine vector comprises a c1857 gene under the control of a constitutive promoter.

In some aspects, the target curing sequence is a pUC origin of replication, and the curing gRNA is an anti-pUC origin gRNA.

In some aspects, the second inducible promoter is a pPhIF promoter.

In some aspects, the method further comprises, after the second transforming step, the additional steps of: selecting for the second transformed cells via the second and third selectable markers; inducing editing in the selected cells by inducing the first and third inducible promoter thereby inducing transcription of the one or more editing gRNA and donor DNA pairs and the nuclease; growing the induced cells until the cells reach a stationary phase of growth; curing the editing vectors from the second set of editing vectors in the induced cells by inducing the third and second inducible promoters thereby inducing transcription of the nuclease and curing gRNA; growing the cells; rendering the cells electrocompetent; and transforming the cells with a third set of the editing vectors to produce third transformed cells, wherein the third set of editing vectors comprises editing cassettes with one or more gRNA and donor DNA pairs under the control of the first inducible promoter, a fourth selectable marker, and the curing target sequence.

In other aspects, the method further comprises after the third transforming step, the steps of: selecting for the third transformed cells via the second and fourth selectable markers; inducing editing in the selected cells by inducing the first and third inducible promoter thereby inducing transcription of the one or more editing gRNA and donor DNA pairs and the nuclease; growing the induced cells until the cells reach a stationary phase of growth; curing the editing vectors from the third set of editing vectors in the induced cells by inducing the third and second inducible promoters thereby inducing transcription of the nuclease and curing gRNA; growing the cells; rendering the cells electrocompetent; and transforming the cells with a fourth set of the editing vectors to produce fourth transformed cells, wherein the fourth set of editing vectors comprises editing cassettes with one or more gRNAs and donor DNA pairs under the control of the first inducible promoter, a fifth selectable marker, and the curing target sequence.

In some aspects, the first, second, third and fourth sets of editing cassettes each comprise a library of editing gRNA and donor DNA pairs; and in some aspects, the libraries of editing vectors each comprises at least 1000 different editing gRNA and donor DNA pairs.

Other embodiments provide a method for curing cells during recursive nucleic acid-directed nuclease editing comprising: designing and synthesizing sets of editing cassettes, wherein the sets of editing cassettes comprise one or more editing gRNA and donor DNA pairs wherein each editing gRNA and donor DNA pair is under the control of a first inducible promoter; assembling the editing cassettes into a vector backbone thereby forming editing vectors, wherein the vector backbone comprises a first selectable marker, a curing target sequence, and a curing gRNA under the control of a second inducible promoter; making cells of choice electrocompetent, wherein the cells of choice comprise an engine vector and the engine vector comprises a nuclease under the control of the third inducible promoter, and a second selectable marker; transforming the cells of choice with a first set editing vectors to produce transformed cells; selecting for transformed cells via the first and second selectable markers; inducing editing in the selected cells by inducing the first and third inducible promoters thereby inducing transcription of the one or more editing gRNA and donor DNA pairs and nuclease; growing the cells until the cells reach a stationary phase of growth; curing the editing vector by inducing the third and second inducible promoters thereby inducing transcription of the nuclease and curing gRNA; growing the cells; rendering the cells electrocompetent; and transforming the cells with a second set of the editing vectors to produce second transformed cells, wherein the second set of editing vectors comprises editing cassettes with one or more gRNA and donor DNA pairs under the control of the first inducible promoter, a third selectable marker, the curing target sequence, and the curing gRNA under the control of the second inducible promoter.

In some aspects of this embodiment, the first inducible promoter and the third inducible promoters are the same inducible promoter, and in some aspects, the first and third inducible promoters are pL promoters and either the editing vector or the engine vector comprises a cI857 gene under the control of a constitutive promoter.

In some aspects, the target curing sequence is a pUC origin of replication, and the curing gRNA is an anti-pUC origin gRNA.

In some aspects, the second inducible promoter is a pPhlF promoter.

In some aspects of this embodiment, the method further comprises, after the second transforming step, the additional steps of: selecting for the second transformed cells via the second and third selectable markers; inducing editing in the selected cells by inducing the first and third inducible promoter thereby inducing transcription of the one or more editing gRNA and donor DNA pairs and the nuclease; growing the induced cells until the cells reach a stationary phase of growth; curing the editing vectors from the second set of editing vectors in the induced cells by inducing the third and second inducible promoters thereby inducing transcription of the nuclease and curing gRNA; growing the cells; rendering the cells electrocompetent; and transforming the cells with a third set of the editing vectors to produce third transformed cells, wherein the third set of editing vectors comprises editing cassettes with one or more gRNA and donor DNA pairs under the control of the first inducible promoter, a fourth selectable marker, the curing target sequence, and the curing gRNA under the control of the second inducible promoter.

In yet another aspect, the method may further comprise the steps of, after the third transforming step: selecting for the third transformed cells via the second and fourth selectable markers; inducing editing in the selected cells by inducing the first and third inducible promoter thereby inducing transcription of the one or more editing gRNA and donor DNA pairs and the nuclease; growing the induced cells until the cells reach a stationary phase of growth; curing the editing vectors from the third set of editing vectors in the induced cells by inducing the third and second inducible promoters thereby inducing transcription of the nuclease and curing gRNA; growing the cells; rendering the cells electrocompetent; and transforming the cells with a fourth set of the editing vectors to produce fourth transformed cells, wherein the fourth set of editing vectors comprises editing cassettes with one or more gRNA and donor DNA pairs under the control of the first inducible promoter, a fifth selectable marker, the curing target sequence, and the curing gRNA under the control of the second inducible promoter.

In some aspects of any of the methods, the method further comprises between the transforming step and inducing step, singulating the cells in a SWIIN, and wherein the selecting, inducing, growing, and curing steps are performed in the SWIIN.

In some aspects, the first, second, third and fourth sets of editing cassettes each comprise a library of editing gRNA and donor DNA pairs; and in some aspects, the libraries of editing vectors each comprises at least 1000 different editing gRNA and donor DNA pairs.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which:

FIGS. 6B-6D depict an embodiment of a solid wall isolation incubation and normalization (SWIIN) module.

It should be understood that the drawings are not necessarily to scale, and that like reference numbers refer to like features.

DETAILED DESCRIPTION

Figure 1A:
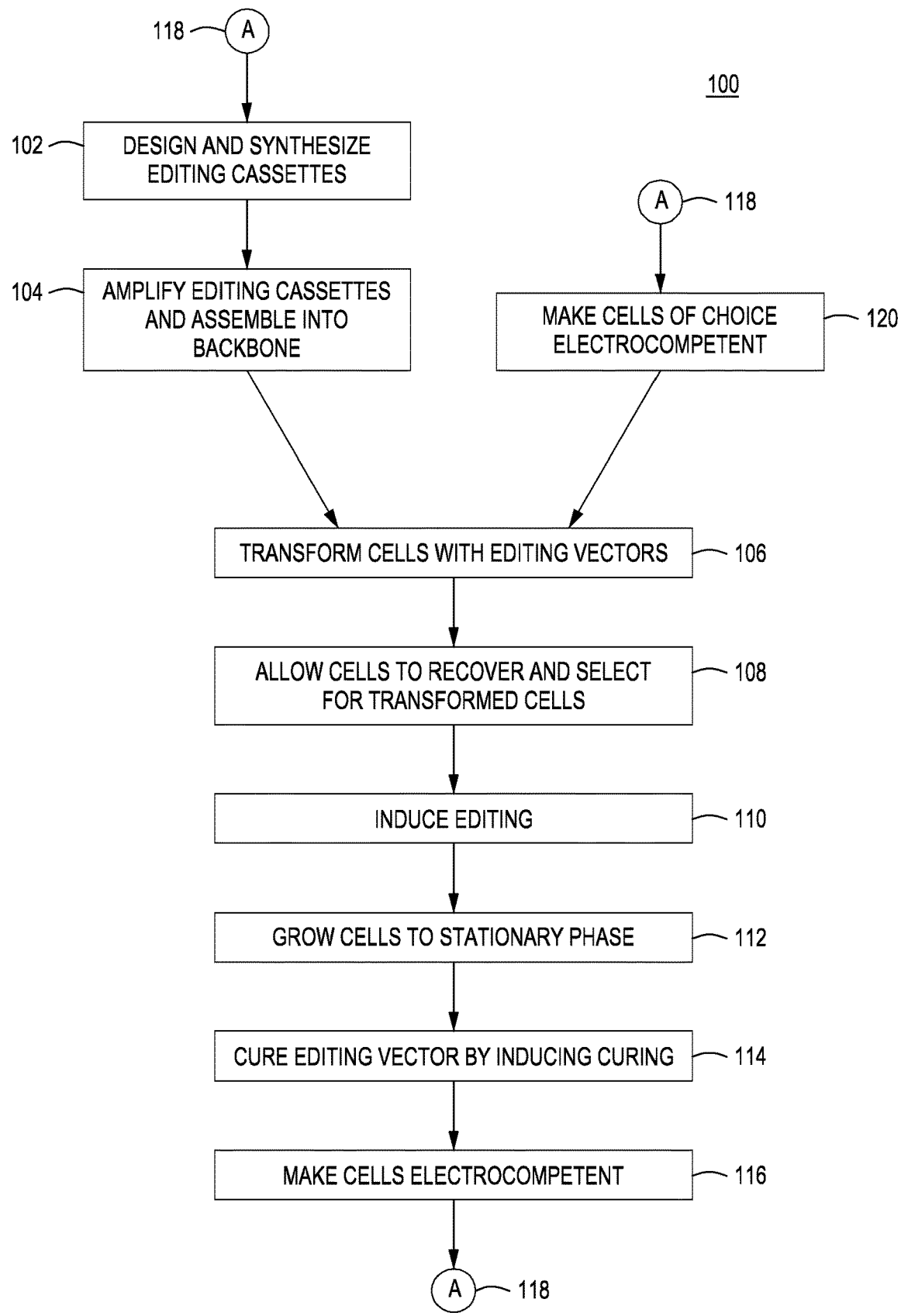
FIG. 1A is a flow chart showing steps for an exemplary curing method according to the present disclosure.

All of the functionalities described in connection with one embodiment of the methods, devices or instruments described herein are intended to be applicable to the additional embodiments of the methods, devices and instruments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of molecular biology (including recombinant techniques), cell biology, biochemistry, and genetic engineering technology, which are within the skill of those who practice in the art. Such conventional techniques and descriptions can be found in standard laboratory manuals such as Green and Sambrook, *Molecular Cloning: A Laboratory Manual.* 4th, ed., Cold Spring Harbor Laboratory Press, Cold Spring Harbor, N.Y., (2014); *Current Protocols* in *Molecular Biology,* Ausubel, et al. eds., (2017); Neumann, et al., *Electroporation and Electrofusion in Cell Biology,* Plenum Press, New York, 1989; and Chang, et al., *Guide to Electroporation and Electrofusion,* Academic Press, California (1992), all of which are herein incorporated in their entirety by reference for all purposes. Nucleic acid-guided nuclease techniques can be found in, e.g., *Genome Editing and Engineering from TALENs and CRISPRs to Molecular Surgery,* Appasani and Church (2018); and *CRISPR: Methods and Protocols,* Lindgren and Charpentier (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "a cell" refers to one or more cells, and reference to "the system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" refers to nucleic acid that is designed to introduce a DNA sequence modification (insertion, deletion, substitution) into a locus (e.g., a target genomic DNA sequence or cellular target sequence) by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. The donor DNA will have two regions of sequence homology (e.g., two homology arms) to the genomic target locus. Preferably, an "insert" region or "DNA sequence modification" region—the nucleic acid modification that one desires to be introduced into a genome target locus in a cell—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the genomic target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the genomic target sequence.

As used herein, "enrichment" refers to enriching for edited cells by singulation, inducing editing, and growth of singulated cells into terminal-sized colonies (e.g., saturation or normalization of colony growth).

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease. The term "editing gRNA" refers to the gRNA used to edit a target sequence in a cell, typically a sequence endogenous to the cell. The term "curing gRNA" refers to the gRNA used to target the curing target sequence on the editing vector.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

As used herein, the terms "protein" and "polypeptide" are used interchangeably. Proteins may or may not be made up entirely of amino acids.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible, and in some embodiments—particularly many embodiments such as those described herein—the transcription of at least one component of the nucleic acid-guided nuclease editing system—and typically at least three components of the nucleic acid-guided nuclease editing system—is under the control of an inducible promoter.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, nourseothricin N-acetyl transferase, chloramphenicol, erythromycin, tetracycline, gentamicin, bleomycin, streptomycin, rifampicin, puromycin, hygromycin, blasticidin, and G418 may be employed. In other embodiments, selectable markers include, but are not limited to sugars such as rhamnose, human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); and Cytidine deaminase (CD; selectable by Ara-C). "Selective medium" as used herein refers to cell growth medium to which has been added a chemical compound or biological moiety that selects for or against selectable markers.

The term "specifically binds" as used herein includes an interaction between two molecules, e.g., an engineered peptide antigen and a binding target, with a binding affinity represented by a dissociation constant of about $10^{-7}$ M, about $10^{-8}$ M, about $10^{-9}$ M, about $10^{-10}$ M, about $10^{-11}$M, about $10^{-12}$M, about $10^{-13}$M, about $10^{-14}$M or about $10^{-15}$M The terms "target genomic DNA sequence", "cellular target sequence", or "genomic target locus" refer to any locus in vitro or in vivo, or in a nucleic acid (e.g., genome) of a cell or population of cells, in which a change of at least one nucleotide is desired using a nucleic acid-guided nuclease editing system. The cellular target sequence can be a genomic locus or extrachromosomal locus. The term "curing target sequence" refers to a sequence in the editing vector that is cleaved or cut to cure or clear the editing vector. The term "target sequence" refers to either or both of a cellular target sequence and a curing target sequence.

The term "variant" may refer to a polypeptide or polynucleotide that differs from a reference polypeptide or polynucleotide but retains essential properties. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide may be a conservatively modified variant. A substituted or inserted amino acid residue may or may not be one encoded by the genetic code (e.g., a non-natural amino acid). A variant of a polypeptide may be naturally occurring, such as an allelic variant, or it may be a variant that is not known to occur naturally.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like. As used herein, the phrase "engine vector" comprises a coding sequence for a nuclease to be used in the nucleic acid-guided nuclease systems and methods of the present disclosure. The engine vector may also comprise, in a bacterial system, the λ Red recombineering system or an equivalent thereof. Engine vectors also typically comprise a selectable marker. As used herein the phrase "editing vector" comprises a donor nucleic acid, including an alteration to the cellular target sequence that prevents nuclease binding at a PAM or spacer in the cellular target sequence after editing has taken place, and a coding sequence for a gRNA. The editing vector may also and preferably does comprise a selectable marker and/or a barcode. In some embodiments, the engine vector and editing vector may be combined; that is, all editing and selection components may be found on a single vector. Further, the engine and editing vectors comprise control sequences operably linked to, e.g., the nuclease coding sequence, recombineering system coding sequences (if present), donor nucleic acid, guide nucleic acid(s), and selectable marker(s).

Nuclease-Directed Genome Editing Generally

In preferred embodiments, the automated instrument described herein performs recursive nuclease-directed genome editing methods for introducing edits to a population of cells, where editing vectors from previous rounds of editing are cured (e.g., cleared) before a subsequent editing vector is introduced into the population of cells. A recent discovery for editing live cells involves nucleic acid-guided nuclease (e.g., RNA-guided nuclease) editing. A nucleic acid-guided nuclease complexed with an appropriate synthetic guide nucleic acid in a cell can cut the genome of the cell at a desired location. The guide nucleic acid helps the nucleic acid-guided nuclease recognize and cut the DNA at a specific target sequence (either a cellular target sequence or a curing target sequence). By manipulating the nucleotide sequence of the guide nucleic acid, the nucleic acid-guided nuclease may be programmed to target any DNA sequence for cleavage as long as an appropriate protospacer adjacent motif (PAM) is nearby. In certain aspects, the nucleic acid-guided nuclease editing system may use two separate guide nucleic acid molecules that combine to function as a guide nucleic acid, e.g., a CRISPR RNA (crRNA) and trans-activating CRISPR RNA (tracrRNA). In other aspects, the guide nucleic acid may be a single guide nucleic acid that includes both the crRNA and tracrRNA sequences.

In general, a guide nucleic acid (e.g., gRNA) complexes with a compatible nucleic acid-guided nuclease and can then hybridize with a target sequence, thereby directing the nuclease to the target sequence. A guide nucleic acid can be DNA or RNA; alternatively, a guide nucleic acid may comprise both DNA and RNA. In some embodiments, a guide nucleic acid may comprise modified or non-naturally occurring nucleotides. In cases where the guide nucleic acid comprises RNA, the gRNA may be encoded by a DNA sequence on a polynucleotide molecule such as a plasmid, linear construct, or the coding sequence may and preferably does reside within an editing cassette and is under the control of an inducible promoter as described below. For additional information regarding "CREATE" editing cassettes, see U.S. Pat. Nos. 9,982,278; 10,266,849; 10,240,167; 10,351,877; 10,364,442; 10,435,715; and 10,465,207 and U.S. Ser. Nos. 16/551,517; 16,773,618; and 16,773,712, all of which are incorporated by reference herein.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In the present methods and compositions, the guide nucleic acids are provided as a sequence to be expressed from a plasmid or vector and comprises both the guide sequence and the scaffold sequence as a single transcript under the control of an inducible promoter. The guide nucleic acids are engineered to target a desired target sequence (either cellular target sequence or curing target sequence) by altering the guide sequence so that the guide sequence is complementary to a desired target sequence, thereby allowing hybridization between the guide sequence and the target sequence. In general, to generate an edit in the target sequence, the gRNA/nuclease complex binds to a target sequence as determined by the guide RNA, and the nuclease recognizes a protospacer adjacent motif (PAM) sequence adjacent to the target sequence. The target sequence can be any polynucleotide endogenous or exogenous to a prokaryotic or eukaryotic cell, or in vitro. For example, the target sequence can be a polynucleotide residing in the nucleus of a eukaryotic cell. A target sequence can be a sequence encoding a gene product (e.g., a protein) or a non-coding sequence (e.g., a regulatory polynucleotide, an intron, a PAM, or "junk" DNA) or a curing target sequence in an editing vector. In the present description, the target sequence for one of the gRNAs, the curing gRNA, is on the editing vector.

The editing guide nucleic acid may be and preferably is part of an editing cassette that encodes the donor nucleic acid that targets a cellular target sequence. Alternatively, the editing guide nucleic acid may not be part of the editing cassette and instead may be encoded on the editing vector backbone. For example, a sequence coding for an editing guide nucleic acid can be assembled or inserted into a vector backbone first, followed by insertion of the donor nucleic acid in, e.g., an editing cassette. In other cases, the donor nucleic acid in, e.g., an editing cassette can be inserted or assembled into a vector backbone first, followed by insertion of the sequence coding for the editing guide nucleic acid. Preferably, the sequence encoding the editing guide nucleic acid and the donor nucleic acid are located together in a rationally-designed editing cassette and are simultaneously inserted or assembled into a vector backbone to create an editing vector. In yet other embodiments, the sequence encoding the guide nucleic acid and the sequence encoding the donor nucleic acid are both included in the editing cassette.

The target sequence—both the cellular target sequence and the curing target sequence—is associated with a protospacer mutation (PAM), which is a short nucleotide sequence recognized by the gRNA/nuclease complex. The precise preferred PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve target site recognition fidelity, decrease target site recognition fidelity, or increase the versatility of a nucleic acid-guided nuclease.

In certain embodiments, the genome editing of a cellular target sequence both introduces a desired DNA change to a cellular target sequence, e.g., the genomic DNA of a cell, and removes, mutates, or renders inactive a proto-spacer mutation (PAM) region in the cellular target sequence. Rendering the PAM at the cellular target sequence inactive precludes additional editing of the cell genome at that cellular target sequence, e.g., upon subsequent exposure to a nucleic acid-guided nuclease complexed with a synthetic guide nucleic acid in later rounds of editing. Thus, cells having the desired cellular target sequence edit and an altered PAM can be selected for by using a nucleic acid-guided nuclease complexed with a synthetic guide nucleic acid complementary to the cellular target sequence. Cells that did not undergo the first editing event will be cut rendering a double-stranded DNA break, and thus will not continue to be viable. The cells containing the desired cellular target sequence edit and PAM alteration will not be cut, as these edited cells no longer contain the necessary PAM site and will continue to grow and propagate.

The range of target sequences (both cellular target sequences and curing target sequences) that nucleic acid-guided nucleases can recognize is constrained by the need for a specific PAM to be located near the desired target sequence. As a result, it often can be difficult to target edits with the precision that is necessary for genome editing. It has been found that nucleases can recognize some PAMs very well (e.g., canonical PAMs), and other PAMs less well or poorly (e.g., non-canonical PAMs). Because the methods disclosed herein allow for identification of edited cells in a background of unedited cells, the methods allow for identification of edited cells where the PAM is less than optimal; that is, the methods for identifying edited cells herein allow for identification of edited cells even if editing efficiency is very low. Additionally, the present methods expand the scope of target sequences that may be edited since edits are more readily identified, including cells where the genome edits are associated with less functional PAMs.

As for the nuclease component of the nucleic acid-guided nuclease editing system, a polynucleotide sequence encoding the nucleic acid-guided nuclease can be codon optimized for expression in particular cell types, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammals including non-human primates. The choice of nucleic acid-guided nuclease to be employed depends on many factors, such as what type of edit is to be made in the target sequence and whether an appropriate PAM is located close to the desired target sequence. Nucleases of use in the methods described herein include but are not limited to Cas 9, Cas 12/CpfI, MAD2, or MAD7 or other MADzymes and nuclease fusions thereof. Nuclease fusion enzymes typically comprise a CRISPR nucleic acid-guided nuclease engineered to cut one DNA strand in the target DNA rather than making a double-stranded cut, and the nuclease portion is fused to a reverse transcriptase. For more information on nickases and nuclease fusion editing see U.S. Ser. Nos. 16/740,418; 16/740,420 and 16/740,421, all filed 11 Jan. 2020. As with the guide nucleic acid, the nuclease is encoded by a DNA sequence on a vector (e.g., the engine vector) and be under the control of an inducible promoter. In some embodiments, the inducible promoter may be separate from but the same as the inducible promoter controlling transcription of the guide nucleic acid; that is, a separate inducible promoter drives the transcription of the nuclease or nuclease fusionand guide nucleic acid sequences but the two inducible promoters may be the same type of inducible promoter (e.g., both are pL promoters). Alternatively, the inducible promoter controlling expression of the nuclease may be different from the inducible promoter controlling transcription of the guide nucleic acid; that is, e.g., the nuclease may be under the control of the pBAD inducible promoter, and the guide nucleic acid may be under the control of the pL inducible promoter.

Another component of the nucleic acid-guided nuclease system is the donor nucleic acid comprising homology to the cellular target sequence. In some embodiments, the donor nucleic acid is on the same polynucleotide (e.g., editing vector or editing cassette) as the guide nucleic acid and preferably is (but not necessarily is) under the control of the same promoter as the editing gRNA (e.g., a single promoter driving the transcription of both the editing gRNA and the donor nucleic acid). The donor nucleic acid is designed to serve as a template for homologous recombination with a cellular target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length. In certain preferred aspects, the donor nucleic acid can be provided as an oligonucleotide of between 20-300 nucleotides, more preferably between 50-250 nucleotides. The donor nucleic acid comprises a region that is complementary to a portion of the cellular target sequence (e.g., a homology arm). When optimally aligned, the donor nucleic acid overlaps with (is complementary to) the cellular target sequence by, e.g., about 20, 25, 30, 35, 40, 50, 60, 70, 80, 90 or more nucleotides. The donor nucleic acid comprises two homology arms (regions complementary to the cellular target sequence) flanking the mutation or difference between the donor nucleic acid and the cellular target sequencee. The donor nucleic acid comprises at least one mutation or alteration compared to the cellular target sequence, such as an insertion, deletion, modification, or any combination thereof compared to the cellular target sequence.

Again, the donor nucleic acid is preferably provided as part of a rationally-designed editing cassette, which is inserted into an editing vector backbone where the editing vector backbone may comprise a promoter driving transcription of the editing gRNA and the donor DNA, and also comprise a selectable marker different from the selectable marker contained on the engine vector, as well as a curing target sequence that is cut or cleaved during curing. Moreover, there may be more than one, e.g., two, three, four, or more editing gRNA/donor nucleic acid rationally-designed editing cassettes inserted into an editing vector (alternatively, a single rationally-designed editing cassette may comprise two to several editing gRNA/donor DNA pairs), where each editing gRNA is under the control of separate different promoters, separate like promoters, or where all gRNAs/donor nucleic acid pairs are under the control of a single promoter. In preferred embodiments the promoter driving transcription of the editing gRNA and the donor nucleic acid (or driving more than one editing gRNA/donor nucleic acid pair) is an inducible promoter and the promoter driving transcription of the nuclease or nuclease fusion is an inducible promoter as well. In some embodiments and preferably, the nuclease and editing gRNA/donor DNA are under the control of the same inducible promoter.

Inducible editing is advantageous in that singulated cells can be grown for several to many cell doublings before editing is initiated, which increases the likelihood that cells with edits will survive, as the double-strand cuts caused by active editing are largely toxic to the cells. This toxicity results both in cell death in the edited colonies, as well as possibly a lag in growth for the edited cells that do survive but must repair and recover following editing. However, once the edited cells have a chance to recover, the size of the colonies of the edited cells will eventually catch up to the size of the colonies of unedited cells. It is this toxicity, however, that is exploited herein to perform curing.

In addition to the donor nucleic acid, an editing cassette may comprise and preferably does comprise one or more primer sites. The primer sites can be used to amplify the editing cassette by using oligonucleotide primers; for example, if the primer sites flank one or more of the other components of the editing cassette.

Also, as described above, the donor nucleic acid may comprise—in addition to the at least one mutation relative to a cellular target sequence—one or more PAM sequence alterations that mutate, delete or render inactive the PAM site in the cellular target sequence. The PAM sequence alteration in the cellular target sequence renders the PAM site "immune" to the nucleic acid-guided nuclease and protects the cellular target sequence from further editing in subsequent rounds of editing if the same nuclease is used.

In addition, the editing cassette may comprise a barcode. A barcode is a unique DNA sequence that corresponds to the donor DNA sequence such that the barcode can identify the edit made to the corresponding cellular target sequence. The barcode typically comprises four or more nucleotides. In some embodiments, the editing cassettes comprise a collection or library editing gRNAs and of donor nucleic acids representing, e.g., gene-wide or genome-wide libraries of editing gRNAs and donor nucleic acids. The library of editing cassettes is cloned into vector backbones where, e.g., each different donor nucleic acid is associated with a different barcode.

Additionally, in some embodiments, an expression vector or cassette encoding components of the nucleic acid-guided nuclease system further encodes a nucleic acid-guided nuclease comprising one or more nuclear localization sequences (NLSs), such as about or more than about 1, 2, 3, 4, 5, 6, 7, 8, 9, 10, or more NLSs. In some embodiments, the engineered nuclease comprises NLSs at or near the amino-terminus, NLSs at or near the carboxy-terminus, or a combination.

The engine and editing vectors comprise control sequences operably linked to the component sequences to be transcribed. As stated above, the promoters driving transcription of one or more components of the nucleic acid-guided nuclease editing system preferably are inducible. A number of gene regulation control systems have been developed for the controlled expression of genes in plant, microbe, and animal cells, including mammalian cells, including the pL promoter (induced by heat inactivation of the cI857 repressor), the pPhlF promoter (induced by the addition of 2,4 diacetylphloroglucinol (DAPG)), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, Calif.); Bujard and Gossen, PNAS, 89(12): 5547-5551 (1992)), the Lac Switch Inducible system (Wyborski et al., Environ Mol Mutagen, 28(4):447-58 (1996); DuCoeur et al., Strategies 5(3):70-72 (1992); U.S. Pat. No. 4,833,080), the ecdysone-inducible gene expression system (No et al., PNAS, 93(8):3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others. In the present methods used in the modules and instruments described herein, it is preferred that at least one of the nucleic acid-guided nuclease editing components (e.g., the nuclease and/or the gRNA) is under the control of a promoter that is activated by a rise in temperature, as such a promoter allows for the promoter to be activated by an increase in temperature, and de-activated by a decrease in temperature, thereby "turning off" the editing process. Thus, in the scenario of a promoter that is de-activated by a decrease in temperature, editing in the cell can be turned off without having to change media; to remove, e.g., an inducible biochemical in the medium that is used to induce editing.

Curing

"Curing" is a process in which a vector—here, the editing vector used in a prior round of editing or an engine vector after the final round of editing—is eliminated from the cells being edited. Curing can be accomplished by 1) cleaving the editing vector using a curing gRNA on the engine or editing vectors thereby rendering the editing vector nonfunctional; 2) diluting the editing vector in the cell population via cell growth—that is, the more growth cycles the cells go through in medium without the antibiotic that selects for the editing vector the fewer daughter cells will retain the editing or engine vector(s)); or 3) by utilizing a heat-sensitive origin of replication on the editing vector. The present disclosure is drawn to transcribing a curing gRNA located on either the editing vector ("self cure") or the engine vector ("engine cure") to cut or cleave a locus located in a curing target sequence in the editing vector after a round of editing and before a next round of editing in a recursive editing process.

FIG. 1A is a flow chart for the curing methods 100 according to the present disclosure. In a first step, a library of rationally-designed editing cassettes is synthesized 102. Methods and compositions particularly favored for designing and synthesizing editing cassettes are described in U.S. Pat. Nos. 9,982,278; 10,266,849; 10,240,167; 10,351,877; 10,364,442; 10,435,715; and 10,465,207 and U.S. Ser. Nos. 16/551,517; 16,773,618; and 16,773,712, all of which are incorporated by reference herein.

Once designed and synthesized, the editing cassettes are amplified, purified and assembled into a vector backbone 104 to create editing cassettes. A number of methods may be used to assemble the editing cassettes including Gibson Assembly®, CPEC, SLIC, Ligase Cycling etc. Additional assembly methods include gap repair in yeast (Bessa, Yeast, 29(10):419-23 (2012)), gateway cloning (Ohtsuka, Curr Pharm Biotechnol, 10(2):244-51 (2009); U.S. Pat. No. 5,888,732 to Hartley et al.; U.S. Pat. No. 6,277,608 to Hartley et al.; and topoisomerase-mediated cloning (Udo, PLoS One, 10(9):e0139349 (2015)); U.S. Pat. No. 6,916,632 B2 to Chestnut et al. These and other nucleic acid assembly techniques are described, e.g., in Sands and Brent, Curr Protoc Mol Biol., 113:3.26.1-3.26.20 (2016); Casini et al., Nat Rev Mol Cell Biol., (9):568-76 (2015); and Patron, Curr Opinion Plant Biol., 19:14-9 (2014)).

In addition to preparing editing cassettes, cells of choice are made electrocompetent 120 for transformation. The cells that can be edited include any prokaryotic, archaeal or eukaryotic cell. For example, prokaryotic cells for use with the present illustrative embodiments can be gram positive bacterial cells, e.g., Bacillus subtilis, or gram-negative bacterial cells, e.g., E. coli cells. Eukaryotic cells for use with the automated multi-module cell editing instruments of the illustrative embodiments include any plant cells and any animal cells, e.g. fungal cells, insect cells, amphibian cells nematode cells, or mammalian cells.

Once the cells of choice are rendered electrocompetent 120, the cells and editing vectors are combined and the editing vectors are transformed into (e.g., electroporated into) the cells 106. The cells may be also transformed simultaneously with a separate engine vector expressing an editing nuclease; alternatively and preferably, the cells may already have been transformed with an engine vector configured to express the nuclease; that is, the cells may have already been transformed with an engine vector or the coding sequence for the nuclease may be stably integrated into the cellular genome such that only the editing vector needs to be transformed into the cells.

Transformation is intended to include to a variety of art-recognized techniques for introducing an exogenous nucleic acid sequence (e.g., DNA) into a target cell, and the term "transformation" as used herein includes all transformation and transfection techniques. Such methods include, but are not limited to, electroporation, lipofection, optoporation, injection, microprecipitation, microinjection, liposomes, particle bombardment, sonoporation, laser-induced poration, head transfection, calcium phosphate or calcium chloride co-precipitation, or DEAE-dextran-mediated transfection. Cells can also be prepared for vector uptake using, e.g., a sucrose or glycerol wash. Additionally, hybrid techniques that exploit the capabilities of mechanical and chemical transfection methods can be used, e.g., magnetofection, a transfection methodology that combines chemical transfection with mechanical methods. In another example, cationic lipids may be deployed in combination with gene guns or electroporators. Suitable materials and methods for transforming or transfecting target cells can be found, e.g., in Green and Sambrook, *Molecular Cloning: A Laboratory Manual*, 4th, ed., Cold Spring Harbor Laboratory Press, Cold Spring Harbor, N.Y., 2014). The present automated methods using the automated multi-module cell processing instrument utilize flow-through electroporation such as the exemplary device shown in FIGS. 5C-5G.

Once transformed, the cells are allowed to recover and selection is performed 108 to select for cells transformed with the editing vector, which in addition to an editing cassette comprises an appropriate selectable marker. As described above, drug selectable markers such as ampilcillin/carbenicillin, kanamycin, chloramphenicol, nourseothricin N-acetyl transferase, erythromycin, tetracycline, gentamicin, bleomycin, streptomycin, puromycin, hygromycin, blasticidin, and G418 or other selectable markers may be employed.

Following selection for properly transformed cells, editing is induced 110 in the cells by induction of transcription of one or both—preferably both—of the nuclease and gRNA. Induction of transcription of one, or, preferably both, of the nuclease and gRNA is prompted by, e.g., using a pL promoter system where the pL promoter is induced by raising the temperature of the cells in the medium to 42° C. for, e.g., one to many hours to induce expression of the nuclease and gRNA for cutting and editing. A number of gene regulation control systems have been developed for the controlled expression of genes in plant, microbe, and animal cells, including mammalian cells, including, in addition to the pL promoter, the pPhIF promoter (induced by the addition of 2,4 diacetylphloroglucinol (DAPG)), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, Calif.); Bujard and Gossen, PNAS, 89(12): 5547-5551 (1992)), the Lac Switch Inducible system (Wyborski et al., Environ Mol Mutagen, 28(4):447-58 (1996); DuCoeur et al., Strategies 5(3):70-72 (1992); U.S. Pat. No. 4,833,080), the ecdysone-inducible gene expression system (No et al., PNAS, 93(8):3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others.

The present compositions and methods preferably make use of rationally-designed editing cassettes such as CREATE cassettes, as described above. Each editing cassette comprises an editing gRNA, a donor DNA comprising an intended edit and a PAM or spacer mutation; thus, e.g., a two-cassette multiplex editing cassette comprises a first editing gRNA, a first editing donor DNA, and a first intended edit and a first PAM or spacer mutation, and at least a second editing gRNA, at least a second donor DNA, and at least a second intended edit and a second PAM or spacer mutation. In some embodiments, a single promoter may drive transcription of both the first and second editing gRNAs and both the first and second donor DNAs, and in some embodiments, separate promoters may drive transcription of the first editing gRNA and first donor DNA, and transcription of the second editing gRNA and second donor DNA. In addition, multiplex editing cassettes may comprise nucleic acid elements between the editing cassettes with, e.g., primer sequences, bridging oligonucleotides, and other "cassette-connecting" sequence elements that allow for the assembly of the multiplex editing cassettes.

Once editing is induced 110, the cells are grown until the cells enter (or are close to entering) the stationary phase of growth 112, followed by inducing curing of the editing vector 114 by activating an inducible promoter driving transcription of the curing gRNA and inducing the inducible promoter driving transcription of the nuclease. It has been found that curing is particularly effective if the edited cells are in the stationary phase of growth. In yet some aspects, the cells are grown for at least 75% of log phase, 80% of log phase, 85% of log phase, 90% of log phase, 95% of log phase, or are in a stationary phase of growth before inducing curing. Exemplary genetic and inducing components for inducing curing are described in more detail in relation to FIGS. 1C and 1D. Once the editing vector has been cured 114, the cells are allowed to recover and grow, and then the cells are made electrocompetent 116 once again, ready for another round of editing 118.

Figure 1B:
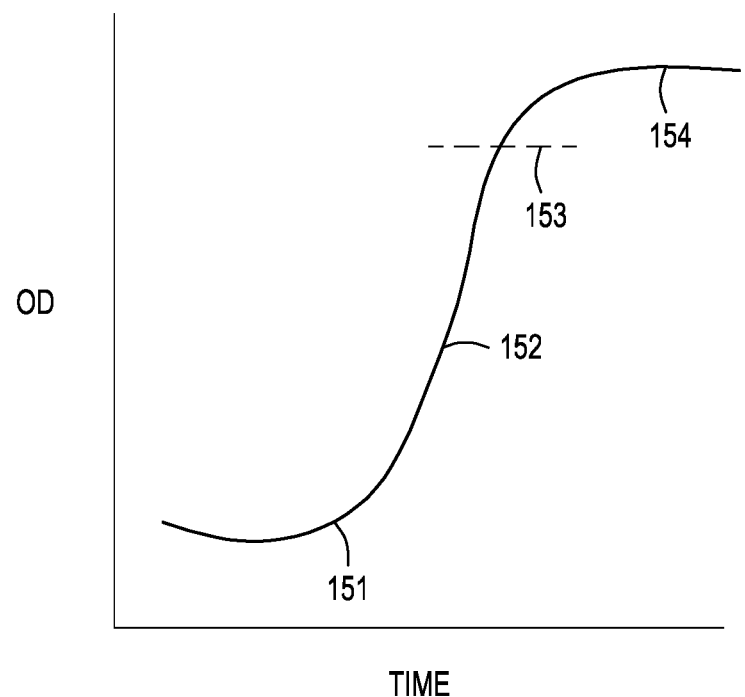
FIG. 1B is an exemplary growth curve for cells.

FIG. 1B depicts a typical growth curve 150 for cells in culture (optical density versus time). Initially there is a lag phase 151, then the cells enter log phase 152 where they grow quickly, and finally the cells reach stationary phase 154 where the cells are no longer dividing. The present methods employ inducing curing at timepoint 153 or later when the cells are in the stationary phase of growth or nearly so; that is, the cells are induced at a timepoint at least 60% into the log phase of growth, or at least 65% into the log phase of growth, or at least 70% into the log phase of growth, or at least 71, 72, 73, 74, 75, 76, 77, 78, 79, 80, 81, 82, 83, 84, 85, 86, 87, 88, 89, 90, 91, 92, 93, 94, 95, 96, 79, 98, or 99% into the log phase of growth, and at any time during the stationary phase of growth.

Figure 1C:
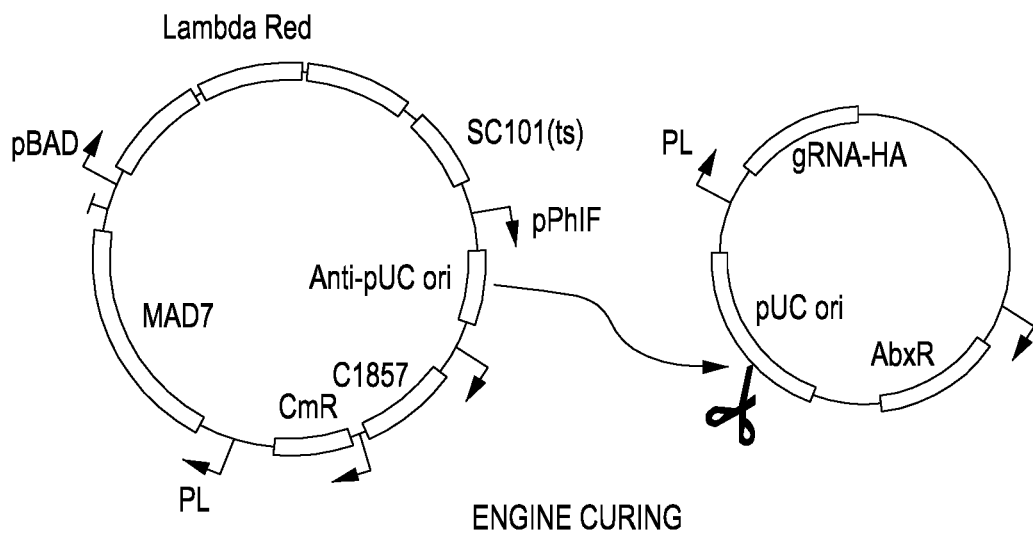
FIG. 1C depicts an exemplary plasmid architecture for engine vector curing of an editing vector and FIG. 1D depicts an exemplary plasmid architecture for self-curing of an editing vector.

FIG. 1C depicts an exemplary plasmid architecture for engine curing of an editing vector comprising an engine vector (on left) and an editing vector (on right); that is, the sequence for the curing gRNA that targets the curing target sequence on the editing vector is located on the engine vector. The engine vector comprises a pBAD inducible promoter 5' of and driving a lambda Red recombineering system. The λ Red recombineering system works as a "band aid" or repair system for double-strand breaks in bacteria, and in some species of bacteria the λ Red recombineering system (or some other recombineering system) must be present for the double-strand breaks that occur during editing to resolve. In yeast and other eukaryotic cells, however, recombineering systems are not required. The inducible promoter (in this case pBAD, but other inducible promoters may be used) driving transcription of the λ Red recombineering system components is most preferably a different inducible promoter than that driving transcription of the nuclease and the editing gRNA, as it is preferred that the recombineering system be active before the nuclease is induced. That is, it is preferred that the "band aid" double-strand break repair machinery be active before the nuclease starts cutting the cellular genome.

In addition to the λ Red recombineering system, the engine vector also comprises an origin of replication (here an SC101 origin, which may be temperature sensitive, but need not be) 3' of the λ Red recombineering system, followed by a pPhIF inducible primer 3' of the SC101 origin driving transcription of the curing gRNA, in this case the curing gRNA is a gRNA that renders inactive the pUC origin of replication on the editing vector (e.g., the curing target sequence). Next, 3' of the curing gRNA sequence is a promoter (typically a constitutive promoter) driving transcription of the c1857 repressor gene, which actively represses the pL promoter at 30° C. and degrades at 42° C. thereby activating the pL promoter. Three prime of the c1857 coding sequence is a promoter (also typically a constitutive promoter) driving transcription of an antibiotic resistance gene—here, a carbenicillin resistance gene—followed by a pL inducible promoter driving transcription of MAD7, the nuclease.

The editing vector on the right in FIG. 1C comprises a pL promoter driving transcription of an editing cassette, where the editing cassette includes a coding sequence for an editing gRNA and a donor DNA sequence (e.g., a homology arm or "HA"). The donor DNA sequence—in addition to a sequence for a desired edit in a nucleic acid sequence endogenous to the cell (e.g., the cellular target sequence)-often further comprises a PAM-altering sequence, which is most often a sequence that disables the PAM at the cellular target sequence in the genome. The editing vector further comprises a promoter (typically a constitutive promoter) driving transcription of an antibiotic resistance gene (e.g., kanamycin or chloramphenicol), followed by a pUC origin of replication. The anti-pUC gRNA (e.g., the curing gRNA), whose transcription is controlled by the pPhIF inducible promoter on the engine, comprises a gRNA that disables the pUC origin on the editing vector (represented by an arrow and scissors in FIG. 1C).

Figure 1D:
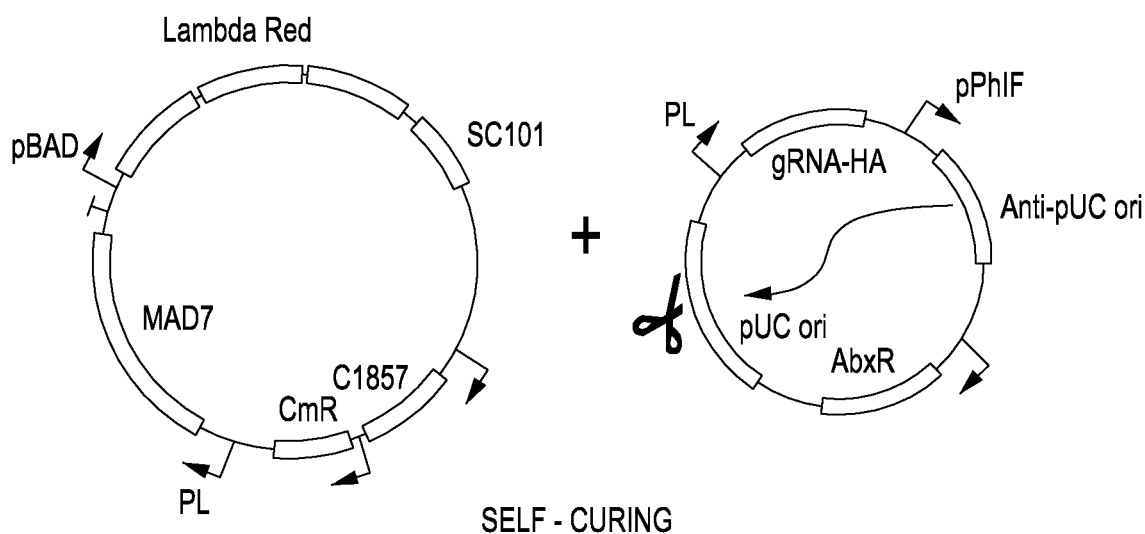

FIG. 1D depicts an exemplary plasmid architecture for self-curing of an editing vector, comprising an engine vector (on left) and an editing vector (on right); that is, the sequence for the curing gRNA that targets the curing target sequence on the editing vector is located on the editing vector itself. The engine vector comprises a pBAD inducible promoter 5' of and driving a lambda red recombineering system. As described above, the λ Red recombineering system works as a "band aid" or repair system for double-strand breaks in bacteria. The inducible promoter (in this case pBAD, but other inducible promoters may be used) driving transcription of the λ Red recombineering system components is most preferably a different inducible promoter than that driving transcription of the nuclease and the editing gRNA, as it is preferred that the recombineering system be active before the nuclease is induced. In addition to the λ Red recombineering system, the engine vector also comprises an origin of replication (here an SC101 origin, which may be temperature sensitive, but need not be) 3' of the λ Red recombineering system, followed by a promoter (typically a constitutive promoter) driving transcription of the c1857 repressor gene, which actively represses the pL promoter at 30° C. and degrades at 42° C. thereby activating the pL promoter. Three prime of the c1857 coding sequence is a promoter (also typically a constitutive promoter) driving transcription of a carbenicillin resistance gene, followed by a pL inducible promoter driving transcription of MAD7, the nuclease.

The editing vector on the right in FIG. 1D comprises a pL promoter driving transcription of an editing cassette, where the editing cassette includes a coding sequence for an editing gRNA and a donor DNA sequence (e.g., a homology arm or "HA"). The donor DNA sequence—in addition to a sequence for a desired, intended edit in a nucleic acid sequence endogenous to the cell—further comprises a PAM-altering sequence, a sequence that disables the PAM at the cellular target sequence in the genome. The editing vector further comprises a pPhIF inducible primer 3' of the editing cassette, where the pPhIF promoter drives transcription of the curing gRNA. As in FIG. 1C, the curing gRNA is a gRNA that renders inactive the pUC origin located on the editing vector; however, in this architecture the curing gRNA is located on the editing vector, hence the editing vector is "self-curing." Three prime of the curing gRNA sequence is a promoter, typically a constitutive promoter, driving transcription of an antibiotic resistance gene (e.g., kanamycin or chloramphenicol, that is an antibiotic resistance gene different from the antibiotic resistance gene located on the engine vector), followed by the pUC origin of replication. The anti-pUC curing gRNA, whose transcription is controlled by the pPhIF inducible promoter, comprises a curing gRNA that cures the editing vector by disabling (e.g., cleaving or cutting) the pUC origin on the editing vector (represented by an arrow and scissors in FIG. 1D). Thus, in the system in FIG. 1D, the editing vector self cures, as the curing gRNA (e.g., the anti-pUC gRNA) is transcribed from the editing vector and disables the pUC origin of replication on the editing vector.

Figure 1E:
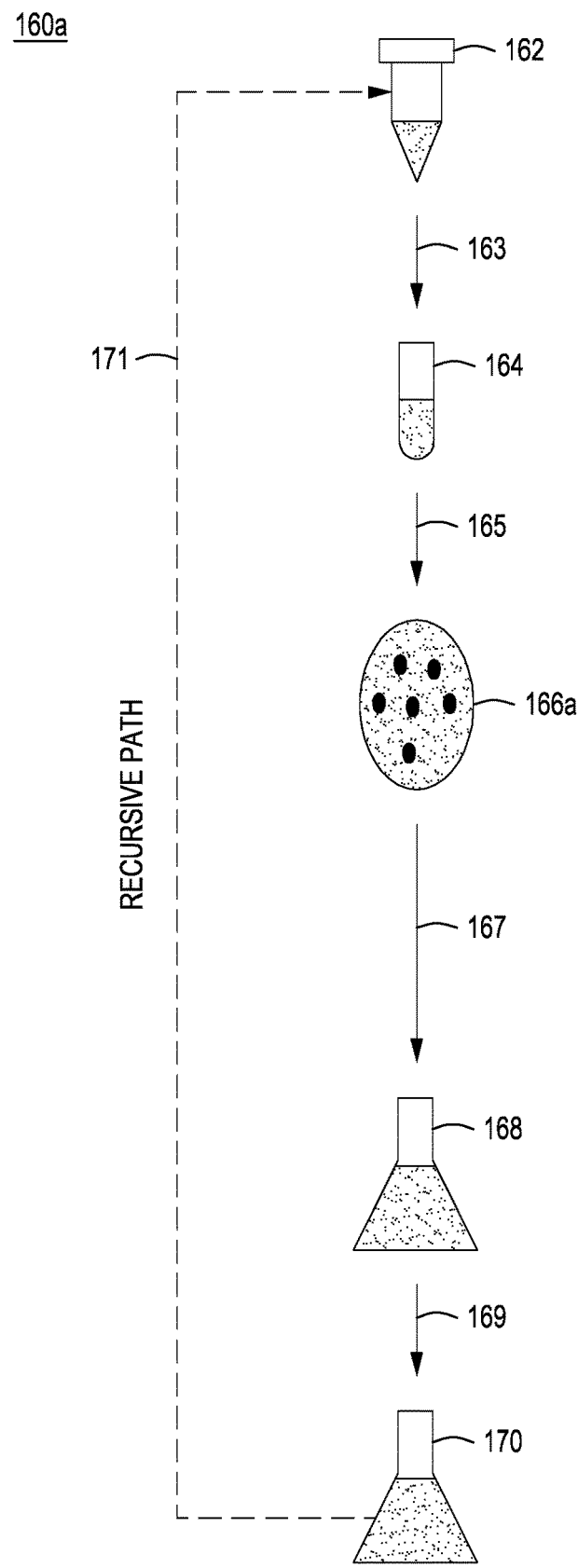
FIG. 1E depicts an exemplary recursive method using a standard plating protocol.

FIG. 1E depicts an exemplary recursive method 160a using a standard plating protocol (SPP) employing, e.g., the exemplary engine and editing vectors shown in FIGS. 1C or 1D. The recursive method 160a begins with competent cells 162, for example, E. coli cells that have been previously transformed with an engine vector expressing a nucleic acid-guided nuclease such as MAD7 and a selective marker, such as a chloramphenicol resistance gene. At step 163, the competent cells are transformed with a library of editing vectors, where each editing vector in the library of editing vectors comprises an editing cassette with a sequence coding for an editing gRNA and a donor DNA, and each editing vector also comprises an antibiotic resistance gene such as a gene conferring resistance to carbenicillin and a curing target sequence. Following transformation, the cells are allowed to recover 164 in medium without antibiotic, and then at step 165, the cells are diluted if necessary, or transferred into medium containing, e.g., chloramphenicol and, e.g., carbenicillin to select for both the engine and editing vectors. The cells are then plated 166a on solid medium containing, e.g., arabinose, which induces the lambda red recombination system encoded by, e.g., the engine vector (see, e.g., FIGS. 1C and 1D). Once plated the cells are allowed to grow at, e.g., 30° C. for 9 hours, at 42° C. for 2 hours—thereby inducing the pL promoters driving transcription of the nuclease on the engine vector and the editing cassette (e.g., the editing gRNA and donor DNA) on the editing vector—then at 30° C. for at least 9 more hours.

At step 167, colonies formed by the transformed cells are removed from the solid medium by, e.g., scraping the colonies from the medium or by picking colonies and then the harvested cells are placed in medium, washed to remove the carbenicillin and resuspended in medium containing chloramphenicol (continuing to select for the engine vector) and allowed to grow until the cells reach the stationary phase of growth or nearly so. Again, it has been found that curing is particularly effective if the edited cells are in the stationary phase of growth when curing is induced. For example, the cells are grown until they have grown for at least 75% of log phase, 80% of log phase, 85% of log phase, 90% of log phase, 95% of log phase, or are in a stationary phase of growth before inducing curing.

The editing vectors in the cells are then cured 168 by inducing transcription of the curing gRNA that cuts the pUC origin of replication on the editing vector. Induction of the curing gRNA is accomplished by first raising the temperature of the culture to 42° C. for 2 hours, thereby inducing the pL promoter driving transcription of the nuclease, and second by the addition of 2,4 diacetylphloroglucinol (DAPG) to induce the pPhIF promoter driving transcription of the anti-pUC gRNA. After 2 hours at 42° C., the temperature of the cell culture is lowered to 30° C. thereby halting transcription of the nuclease, and the cells are allowed to recover and grow for 6 additional hours. The co-expression of the nuclease and the anti-pUC gRNA permits targeting of the pUC origin of expression on the editing vector (e.g., the curing target sequence). As an alternative protocol to increasing the temperature of the culture to 42° C. combined with addition of DAPG, one can induce the pL promoter driving transcription of the nuclease by increasing the temperature of the culture to 42° C. for two hours, then lower the temperature of the culture to 30° C. and add DAPG to induce transcription of the anti-pUC gRNA; that is, the induction of the nuclease and the anti-pUC gRNA may be sequential rather than simultaneous.

At step 169, the cells are washed with medium containing chloramphenicol (again to select for cells comprising the engine vector), and the cells are allowed to recover. At this point, the edited cells can be grown to, e.g., OD=0.5, made electrocompetent once more 170, and be subjected to a second round of editing 171.

Figure 1F:
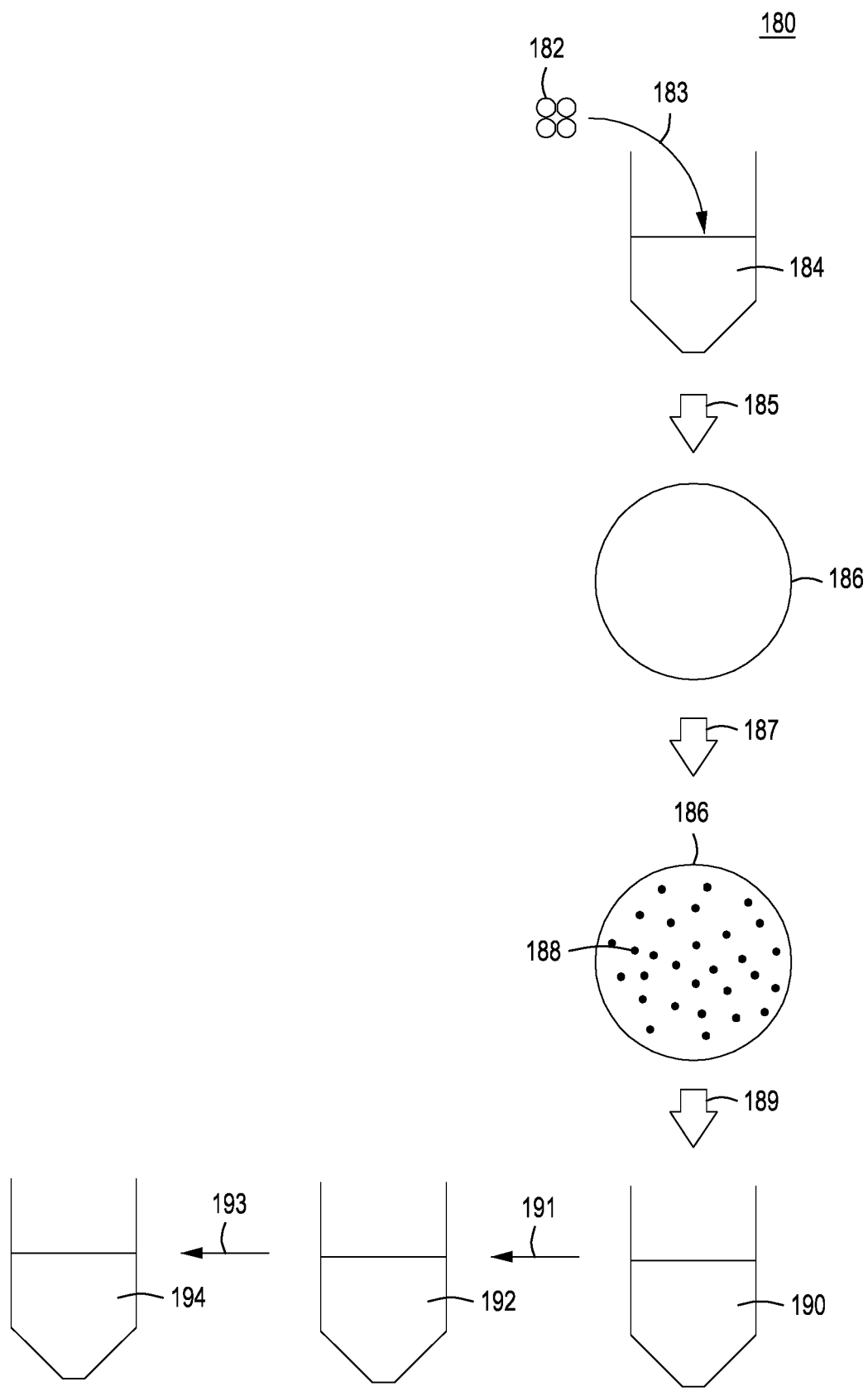
FIG. 1F depicts the exemplary recursive method using the standard plating protocol of FIG. 1E.

FIG. 1F depicts the exemplary recursive editing and curing method using the standard plating protocol (SPP) of FIG. 1E. FIG. 1F depicts the exemplary standard plating protocol embodiment of an improved protocol 180 for performing nucleic acid-guided nuclease genome editing and curing using inducible promoters to drive expression of the editing gRNA, the nuclease, and the curing gRNA. In FIG. 1F as in FIG. 1E, a library or collection of editing vectors 182 is introduced 183 (e.g., electroporated) into cultured cells 184 that already comprise a coding sequence for a nuclease under the control of an inducible promoter. Like FIG. 1E (and as depicted in FIGS. 1C and 1D), the coding sequence for the nuclease is contained on an "engine vector" with a selectable marker that has already been transformed into the cells, although in other embodiments, the coding sequence for the nuclease may be integrated into the genome of the cells. In yet other embodiments, the coding sequence for the nuclease may be located on the editing vector (that is, a combined engine and editing vector).

The editing vectors 182 comprise a donor DNA with a desired, intended edit vis-à-vis a cellular target sequence with a PAM-altering sequence which is most often a sequence that disables the PAM at the target site in the genome, a coding sequence for an editing gRNA under the control of an inducible promoter, and a selectable marker. Depending on whether the system is an engine curing system or a self-curing system, there is also a coding sequence for a curing gRNA under the control of an inducible promoter located on the engine vector or editing vector, respectively.

Once the cells 184 have been transformed with the editing vectors, the cells are plated 185 on selective medium on substrate or plate 186 to select for cells that have both the engine and the editing vectors. The cells are diluted before plating such that the cells are substantially or largely singulated—separated enough so that they and the colonies they form are separated from other cell colonies—and the cells are then grown 187 on plate or substrate 186 until colonies 188 begin to form. The cells are allowed to grow at, e.g., 30° C. for, e.g., between 2 and 300, or between 5 and 150, or between 10 and 50 doublings, establishing clonal colonies. This initial growth of cells is to accumulate enough clonal cells in a colony to survive induction of editing.

Once colonies are established, cutting and editing of the cellular genome is induced by first inducing the promoter driving transcription of the λ. Red recombineering system, and second by inducing or activating the promoters driving the gRNA and nuclease. The inducible promoter driving expression of the λ. Red recombineering system preferably is different from the inducible promoter driving transcription of the gRNA and nuclease and preferably the λ. Red recombineering system is induced before induction of the nuclease and gRNA, as the λ. Red recombineering system works as the "band aid" or repair system for double-strand breaks in bacteria, and in some species of bacteria (but not in other cell types such as yeast or other eukaryotic cells) must be present for the double-strand breaks that occur during editing to resolve. The λ Red recombineering system may be under the control of, e.g., a pBAD promoter. The pBAD promoter is regulated (induced) by the addition of arabinose to the growth medium. Thus, if there is arabinose contained in the selective medium of substrate or plate 186, the λ Red recombineering system will be activated when the cells are grown 187. As for induction of editing, if transcription of the gRNA and nuclease are both under control of the pL promoter, transcription of the gRNA and nuclease is induced by increasing the temperature to 42° C. for, e.g., a half-hour to two hours (or more, depending on the cell type), which activates the pL inducible promoter. Following induction of cutting and editing and a two-hour 42° C. incubation, the temperature is returned to 30° C. to allow the cells to recover and to disable the pL promoter system.

Once the cells have been edited and have been grown at 30° C. for several hours, the colonies are then pooled 189 by, e.g., scraping the colonies off the substrate or plate to pool 190 the cells from the cell colonies. Once the colonies are pooled, curing 191 can take place. As described in relation to FIG. 1E, the editing vectors in the cells are cured by growing the cells until they are in the stationary phase of growth or nearly so, and by inducing transcription of the curing gRNA that cuts the pUC origin of replication on the editing vector. Induction of the anti-pUC gRNA is accomplished by first raising the temperature of the culture to 42° C. for 2 hours, thereby inducing the pL promoter driving transcription of the nuclease, and second by the addition of 2,4 diacetylphloroglucinol (DAPG) to induce the pPhIF promoter driving transcription of the anti-pUC gRNA. After 2 hours at 42° C., the temperature of the cell culture is lowered to 30° C., and the cells are allowed to recover and grow for 6 additional hours. The co-expression of the nuclease and the anti-pUC gRNA permits targeting of the pUC origin of expression on the editing vector thereby producing edited cells in which the editing vector has been cured 192. Additionally, growing the cells performs "passive" curing as well, where the editing vector is "diluted out" of the growing cell population, as removing from the medium the antibiotic that selects for the editing vector removes pressure on cells to retain the editing vector. Finally, at step 193 the edited cells are allowed to recover, then are grown to, e.g., OD=0.5, and rendered electrocompetent 193 so that the cells 194 are ready for another round of editing.

Figure 1G:
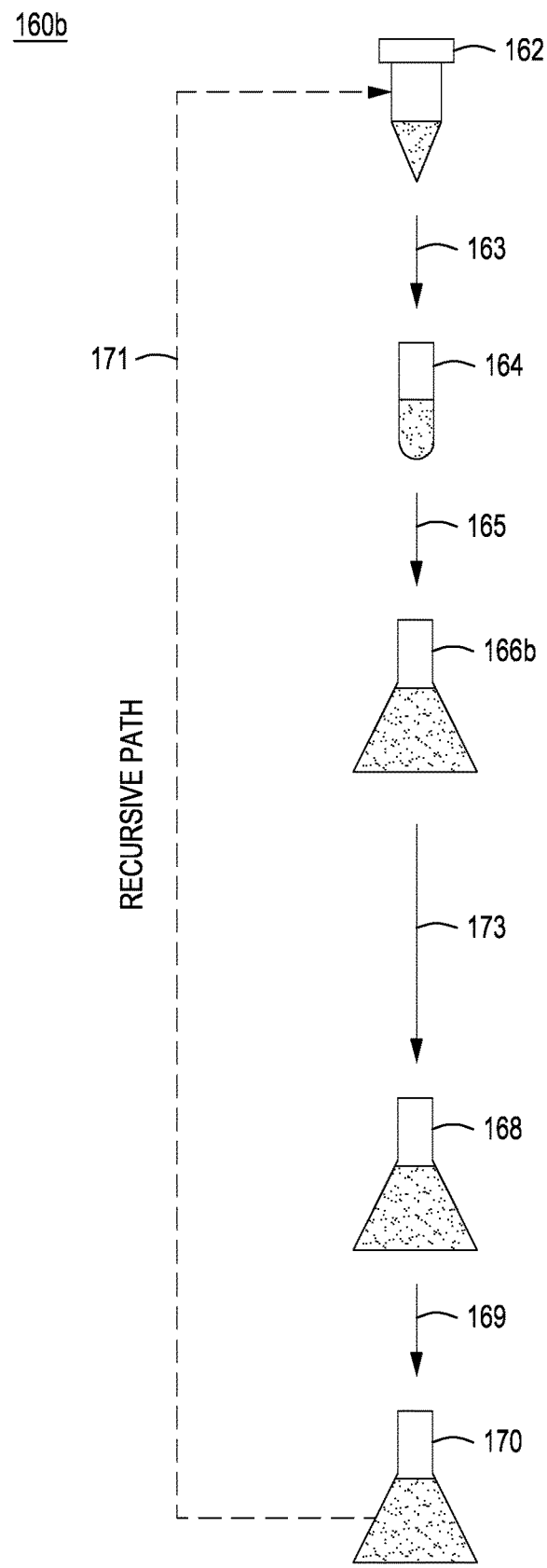
FIG. 1G depicts an exemplary recursive method using a bulk liquid editing protocol.

FIG. 1G depicts an exemplary recursive method 160*b* using a bulk liquid editing protocol. The recursive method 160b—as with the recursive method 160a—begins with competent cells 162, for example E. coli cells that have been previously transformed with an engine vector expressing a nucleic acid-guided nuclease such as MAD7 and a selective marker, such as a chloramphenicol resistance gene. At step 163, the competent cells are transformed with a library of editing vectors, where each editing vector in the library of editing vectors comprises an editing cassette with a sequence coding for an editing gRNA and a donor DNA, and each editing vector also comprises an antibiotic resistance gene such as a gene conferring resistance to, e.g., carbenicillin, where the antibiotic resistance gene located on the editing vector is different from the antibiotic resistance gene located on the engine vector. Following transformation, the cells are allowed to recover 164 in medium without antibiotic, and then at step 165, the cells are diluted, if necessary, or transferred into medium containing chloramphenicol and carbenicillin to select for both the engine and editing vectors.

After transfer to a larger liquid volume 166b for bulk liquid editing, the cells are outgrown; that is, the cells are grown to saturation (see FIG. 1B). Like the curing step, it has been determined that editing in a bulk liquid culture is optimized when the cells have been grown to late log phase or saturation before inducing editing. Again, the cells are grown through at least 60% of log phase, or at least 75% of log phase, 80% of log phase, 85% of log phase, 90% of log phase, 95% of log phase, or are in a stationary phase of growth before inducing curing. Thus, the cells are outgrown, then arabinose is added to the medium, inducing the lambda Red recombination system encoded by, e.g., the engine vector (see, e.g., FIGS. 1C and 1D). Once the lambda Red recombination system is induced for, e.g., 30 minutes to an hour, the temperature is increased 42° C. for 2 hours, thereby inducing the pL promoters driving transcription of the nuclease on the engine vector and the editing cassette on the editing vector and thus editing. After 2 hours at 42° C., the cells are grown at 30° C. for at least 9 more hours.

At step 173, the cells are washed to, e.g., remove the carbenicillin, and resuspended in medium containing chloramphenicol (continuing to select for the engine vector) and the cells may be grown for another length of time to assure that the cells are in the stationary phase of growth for curing. The editing vectors in the cells are then cured 168 by inducing transcription of the editing gRNA that cuts the pUC origin of replication on the editing vector. Induction of the anti-pUC gRNA is accomplished by first raising the temperature of the culture to 42° C. for 2 hours, thereby inducing the pL promoter driving transcription of the nuclease, and second by the addition of 2,4 diacetylphloroglucinol (DAPG) to induce the pPhlF promoter driving transcription of the anti-pUC gRNA (see, e.g., the vector architecture of the engine and editing vectors in FIGS. 1C and 1D). After 2 hours at 42° C., the temperature of the cell culture is lowered to 30° C., and the cells are allowed to recover and grow for 6 additional hours. The co-expression of the nuclease and the anti-pUC gRNA permits targeting of the pUC origin of expression on the editing vector. At step 169, the cells are washed with medium containing chloramphenicol (again to select for cells comprising the engine vector), and the cells are allowed to recover. At this point, the edited cells can be grown to a proper OD (e.g., OD=0.5), made electrocompetent once more 170, and subjected to a second round of editing 171.

Figure 1H:
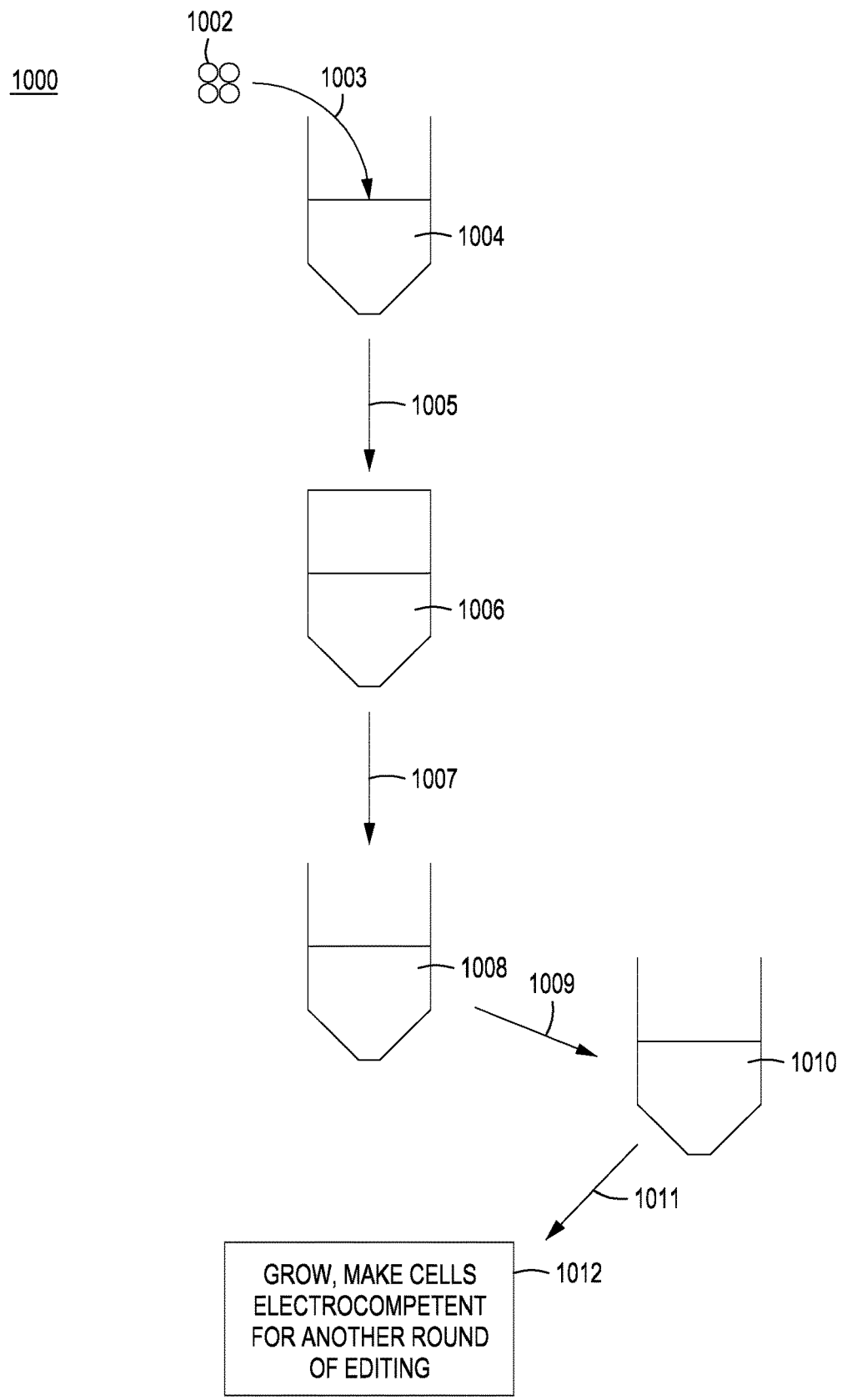
FIG. 1H depicts the exemplary recursive method using the bulk liquid editing protocol of FIG. 1G.

FIG. 1H depicts the exemplary recursive method using the bulk liquid editing protocol of FIG. 1G. FIG. 1H depicts an exemplary protocol 1000 for performing nucleic acid-guided nuclease genome editing and curing. FIG. 1H depicts the protocol 160b shown in FIG. 1G for editing cells. First, a library or collection of editing vectors 1002 (editing vectors each comprising an editing cassette) is introduced 1003 (e.g., electroporated) into cultured cells 1004 that comprise a coding sequence for a nuclease (e.g., MAD7) under the control of an inducible promoter, contained on an engine vector (along with a selectable marker) that has already been transformed into the cells or already integrated into the genome of the cells being transformed. The editing vectors 1002 comprise a donor DNA comprising a PAM or spacer-altering sequence, a coding sequence for an editing gRNA under the control of an inducible promoter, and a selectable marker. Depending on whether the system is an engine curing system or a self-curing system, a coding sequence for a curing gRNA under the control of an inducible promoter is located on the engine vector or editing vector, respectively.

At step 1005, cells are grown until they reach stationary phase, or nearly so. Once the cells reach the stationary phase 1006, editing is induced 1007 where transcription of the nuclease and gRNA is induced and the cells in the culture 1008 are edited and then allowed to recover from editing. Induction of editing in some embodiments comprises raising the temperature of the bulk liquid culture to 42° C. to activate the pL promoter driving transcription of the nuclease, editing gRNA, and donor DNA. Once recovered, the cells are washed, and resuspended in medium 1009 and again outgrown so that the cells are in the stationary phase of growth or nearly so. The editing vectors in the cells are then cured 1010 by inducing transcription of the curing gRNA that cuts the pUC origin of replication on the editing vector. Induction of the anti-pUC gRNA is accomplished by first raising the temperature of the culture to 42° C. for 2 hours, thereby inducing the pL promoter driving transcription of the nuclease, and second by the addition of 2,4 diacetylphloroglucinol (DAPG) to induce the pPhlF promoter driving transcription of the anti-pUC gRNA (see the vector architectures of the exemplary engine and editing vectors in FIGS. 1C and 1D).

After 2 hours at 42° C., the temperature of the cell culture is lowered to 30° C., and the cells are allowed to recover and grow for 6 additonal hours. The co-expression of the nuclease and the anti-pUC gRNA permits targeting of the pUC origin of expression on the editing vector. Growing the cells further performs "passive editing" as described above. At step 1011, the cells are washed with medium containing chloramphenicol (again to select for cells comprising the engine vector), and the cells are allowed to recover. At this point, the edited cells can be made electrocompetent once more 1012 and be subjected to a second round of editing.

Figure 1I:
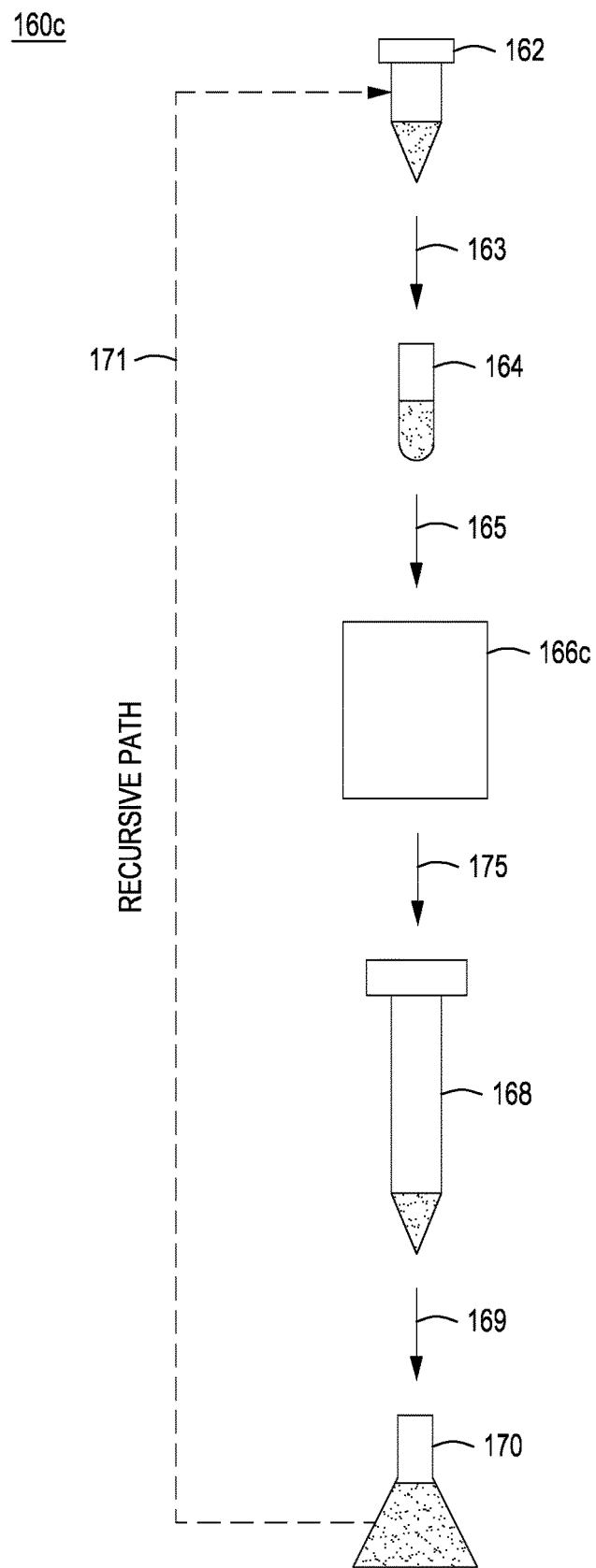
FIG. 1I depicts an exemplary recursive method using a solid wall isolation device.

FIG. 1I depicts an exemplary recursive method 160c using a solid wall isolation device. The recursive method 160c—as with the recursive methods 160a and 160b—begins with competent cells 162, for example, E. coli cells that have been previously transformed with an engine vector expressing a nucleic acid-guided nuclease such as MAD7 and a selective marker, such as a chloramphenicol resistance gene. At step 163, the competent cells are transformed with a library of editing vectors, where each editing vector in the library of editing vectors comprises an editing cassette with a sequence coding for an editing gRNA and a donor DNA, and each editing vector also comprises an antibiotic resistance gene such as a gene conferring resistance to carbenicillin or other antibiotic gene different from the antibiotic gene on the engine vector. Following transformation, the cells are allowed to recover 164 in medium without antibiotic, and then at step 165, the cells are diluted, if necessary, and loaded onto a solid wall singulation, induction, isolation and normalization device (a SWIIN, described in detail below in relation to FIGS. 6B-6E) 166c where the editing process takes place. The cells are loaded into the SWIIN in a Poisson or substantial Poisson distribution (described in detail below) and are grown for at 30° C. for approximately 8-9 hours. After the initial growth phase, medium exchange is performed, adding arabinose to the culture medium to induce the lambda Red recombination system encoded by, e.g., the engine vector (see, e.g., the exemplary vector architectures of FIGS. 1C and 1D).

Once the lambda Red recombination system is induced for, e.g., 30 minutes to an hour, the temperature of the SWIIN is increased 42° C. for 2 hours, thereby inducing the pL promoters driving transcription of the nuclease on the engine vector and the editing cassette (editing gRNA and donor DNA) on the editing vector and thus inducing editing. After 2 hours at 42° C., the cells are grown at 30° C. for at least 9 more hours.

At step 175, the cells are recovered from the SWIIN and washed to, e.g., remove the carbenicillin. The cells are then resuspended in medium containing chloramphenicol (continuing to select for the engine vector) and out-grown so that the cells are in late log phase or stationary phase. The editing vectors in the cells are then cured 168 by inducing transcription of the curing gRNA that cuts the pUC origin of replication on the editing vector. Induction of the anti-pUC gRNA is accomplished by first raising the temperature of the culture to 42° C. for 2 hours, thereby inducing the pL promoter driving transcription of the nuclease, and second by performing media exchange to medium with of 2,4 diacetylphloroglucinol (DAPG) added to induce the pPhlF promoter driving transcription of the anti-pUC gRNA (see FIGS. 1C and 1D).

Figure 6A:
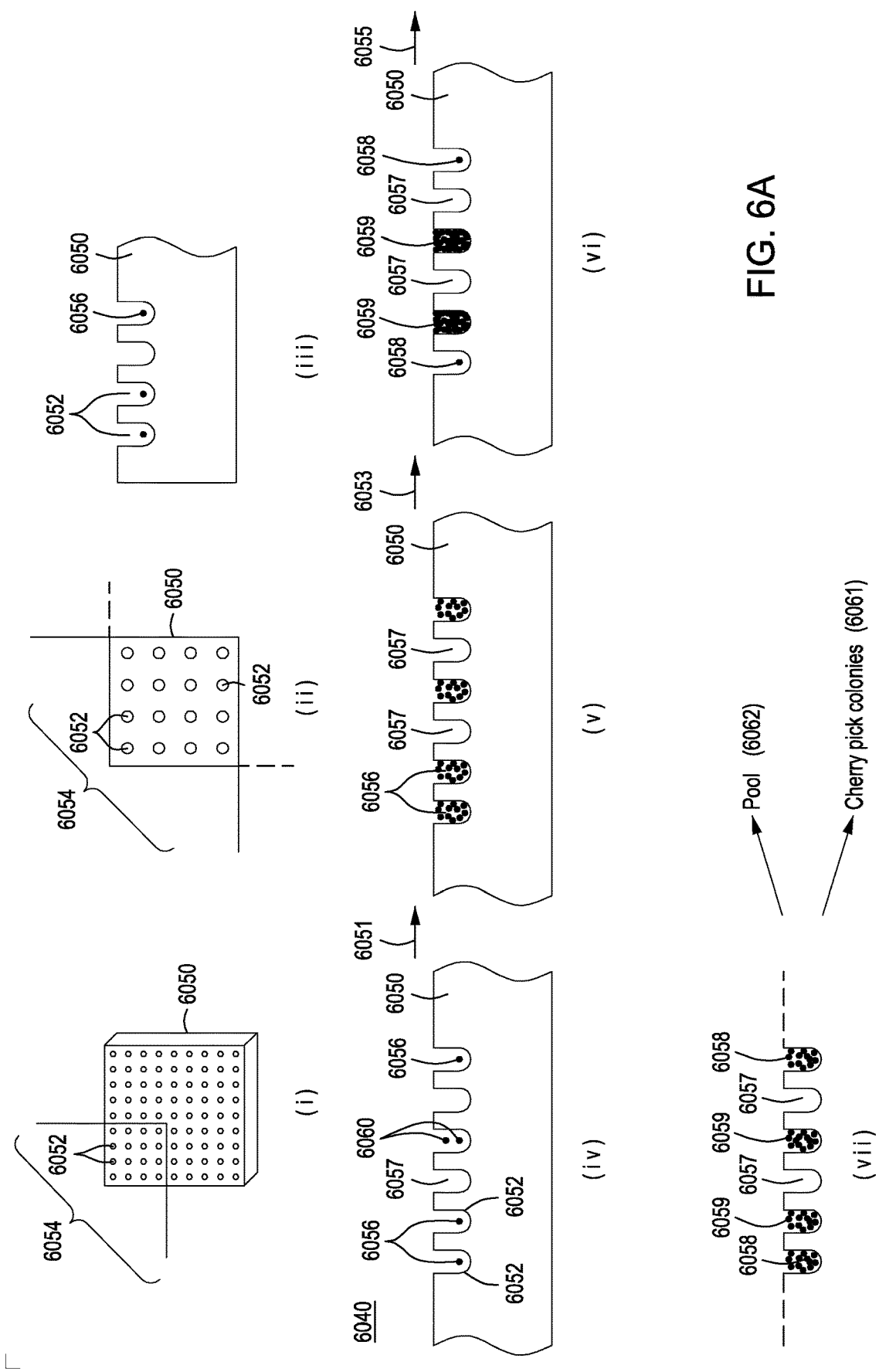
FIG. 6A depicts a simplified graphic of a workflow for singulating, editing and normalizing cells in a solid wall device.

After 2 hours at 42° C., the temperature of the cell culture is lowered to 30° C., and the cells are allowed to recover and grow for 6 hours. The co-expression of the nuclease and the anti-pUC gRNA permits targeting of the pUC origin of expression on the editing vector. At step 169, the cells are washed with medium containing chloramphenicol (again to select for cells comprising the engine vector), and the cells are allowed to recover and are grown to be made electrocompetent. Growing the cells also performs "passive" curing, where the editing vector is "diluted out" of the growing cell population, as removing from the medium the antibiotic that selects for the editing vector removes pressure on cells to retain the editing vector. At this point, the edited cells can be made electrocompetent once more 170 and be subjected to a second round of editing 171. FIG. 6A depicts and the description of FIG. 6A presents this method in additional detail.

Figure 2A:
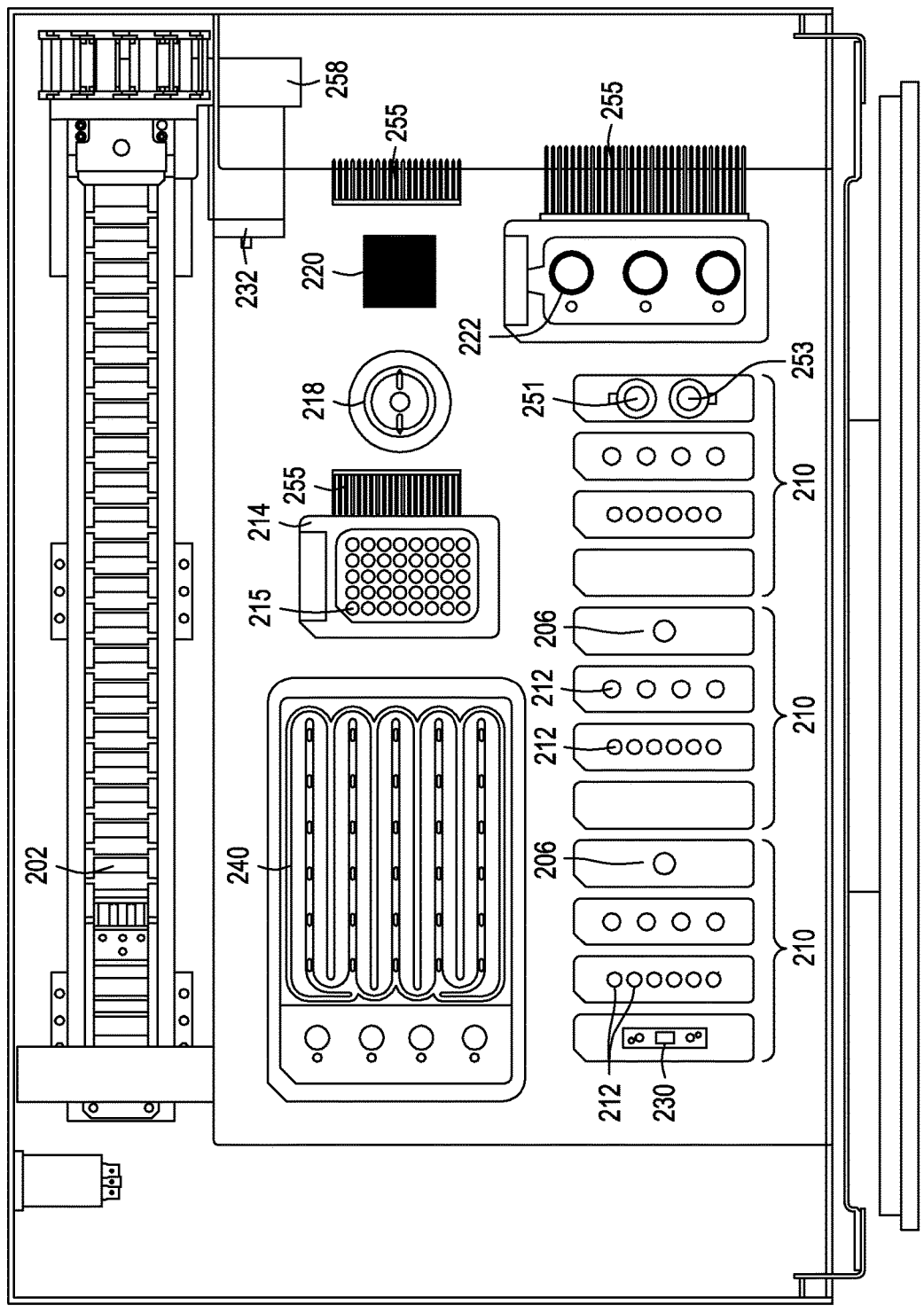
FIGS. 2A-2C depict three different views of an exemplary automated multi-module cell processing instrument for performing nucleic acid-guided nuclease editing.

Automated Cell Editing Instruments and Modules to Perform Nucleic Acid-Guided Nuclease Editing including Curing Automated Cell Editing Instruments FIG. 2A depicts an exemplary automated multi-module cell processing instrument 200 to, e.g., perform one of the exemplary recursive workflows for targeted gene editing of live yeast cells. The instrument 200, for example, may be and preferably is designed as a stand-alone desktop instrument for use within a laboratory environment. The instrument 200 may incorporate a mixture of reusable and disposable components for performing the various integrated processes in conducting automated genome cleavage and/or editing in cells without human intervention. Illustrated is a gantry 202, providing an automated mechanical motion system (actuator) (not shown) that supplies XYZ axis motion control to, e.g., an automated (i.e., robotic) liquid handling system 258 including, e.g., an air displacement pipettor 232 which allows for cell processing among multiple modules without human intervention. In some automated multi-module cell processing instruments, the air displacement pipettor 232 is moved by gantry 202 and the various modules and reagent cartridges remain stationary; however, in other embodiments, the liquid handling system 258 may stay stationary while the various modules and reagent cartridges are moved.

Figure 5A:
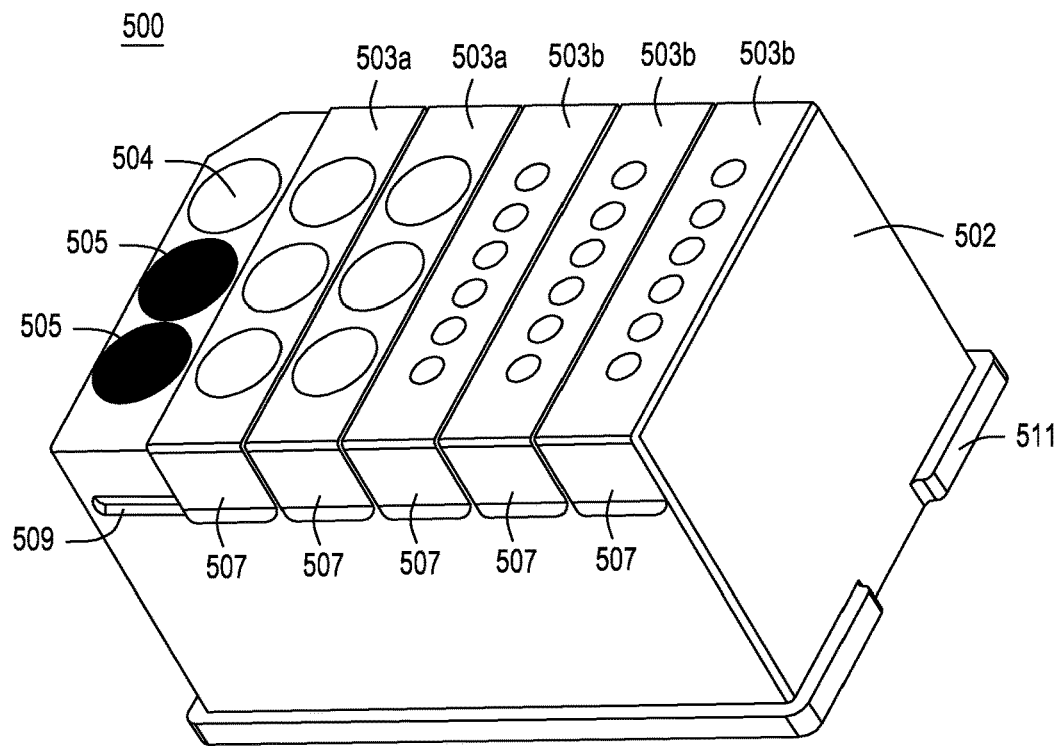
FIGS. 5A and 5B depict the structure and components of an embodiment of a reagent cartridge.
Figure 5B:
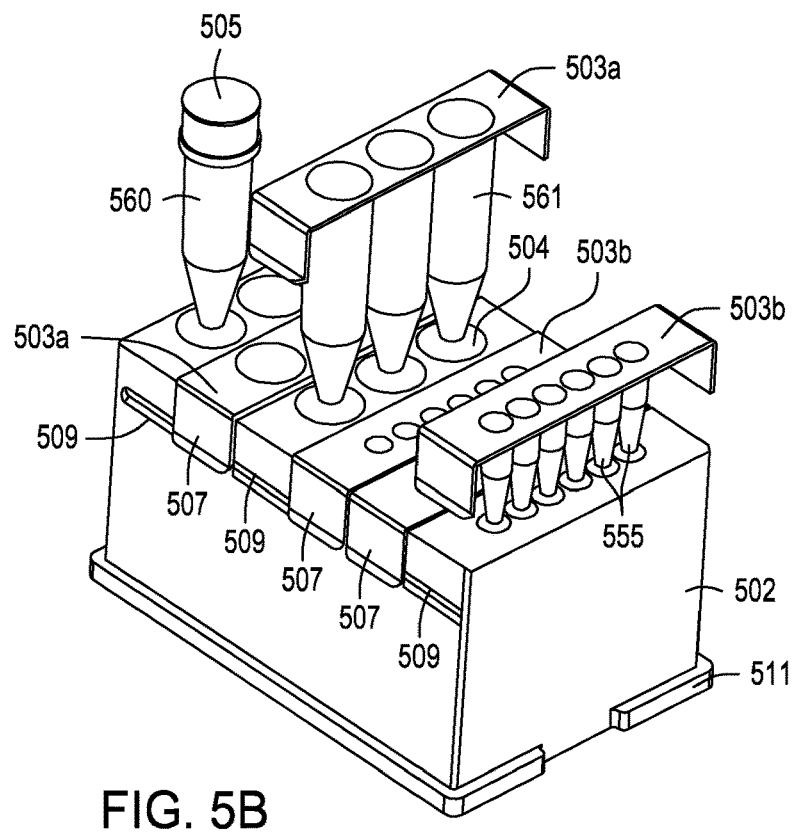

Also included in the automated multi-module cell processing instrument 200 are reagent cartridges 210 comprising reservoirs 212 and transformation module 230 (e.g., a flow-through electroporation device as described in detail in relation to FIGS. 5C-5G and an exemplary reagent cartridge is described in relation to FIGS. 5A and 5B), as well as wash reservoirs 206, cell input reservoir 251 and cell output reservoir 253. The wash reservoirs 206 may be configured to accommodate large tubes, for example, wash solutions, or solutions that are used often throughout an iterative process. Although two of the reagent cartridges 210 comprise a wash reservoir 206 in FIG. 2A, the wash reservoirs instead could be included in a wash cartridge where the reagent and wash cartridges are separate cartridges. In such a case, the reagent cartridge 210 and wash reservoir 206 may be identical except for the consumables (reagents or other components contained within the various inserts) inserted therein.

In some implementations, the reagent cartridges 210 are disposable kits comprising reagents and cells for use in the automated multi-module cell processing/editing instrument 200. For example, a user may open and position each of the reagent cartridges 210 comprising various desired inserts and reagents within the chassis of the automated multi-module cell editing instrument 200 prior to activating cell processing. Further, each of the reagent cartridges 210 may be inserted into receptacles in the chassis having different temperature zones appropriate for the reagents contained therein.

Also illustrated in FIG. 2A is the robotic liquid handling system 258 including the gantry 202 and air displacement pipettor 232. In some examples, the robotic handling system 258 may include an automated liquid handling system such as those manufactured by Tecan Group Ltd. of Mannedorf, Switzerland, Hamilton Company of Reno, Nev. (see, e.g., WO2018015544A1), or Beckman Coulter, Inc. of Fort Collins, Colo. (see, e.g., US20160018427A1). Pipette tips 215 may be provided in a pipette transfer tip supply 214 for use with the air displacement pipettor 232.

Inserts or components of the reagent cartridges 210, in some implementations, are marked with machine-readable indicia (not shown), such as bar codes, for recognition by the robotic handling system 258. For example, the robotic liquid handling system 258 may scan one or more inserts within each of the reagent cartridges 210 to confirm contents. In other implementations, machine-readable indicia may be marked upon each reagent cartridge 210, and a processing system (not shown, but see element 237 of FIG. 2B) of the automated multi-module cell editing instrument 200 may identify a stored materials map based upon the machine-readable indicia. In the embodiment illustrated in FIG. 2A, a cell growth module comprises a cell growth vial 218 (described in greater detail below in relation to FIGS. 3A-3D). Additionally seen is the TFF module 222 (described above in detail in relation to FIGS. 4A-4E). Also illustrated as part of the automated multi-module cell processing instrument 200 of FIG. 2A is a singulation module 240 (e.g., a solid wall isolation, incubation and normalization device (SWIIN device) is shown here) described herein in relation to FIGS. 6B-6E, served by, e.g., robotic liquid handing system 258 and air displacement pipettor 232. Additionally seen is a selection module 220. Also note the placement of three heatsinks 255.

Figure 2B:
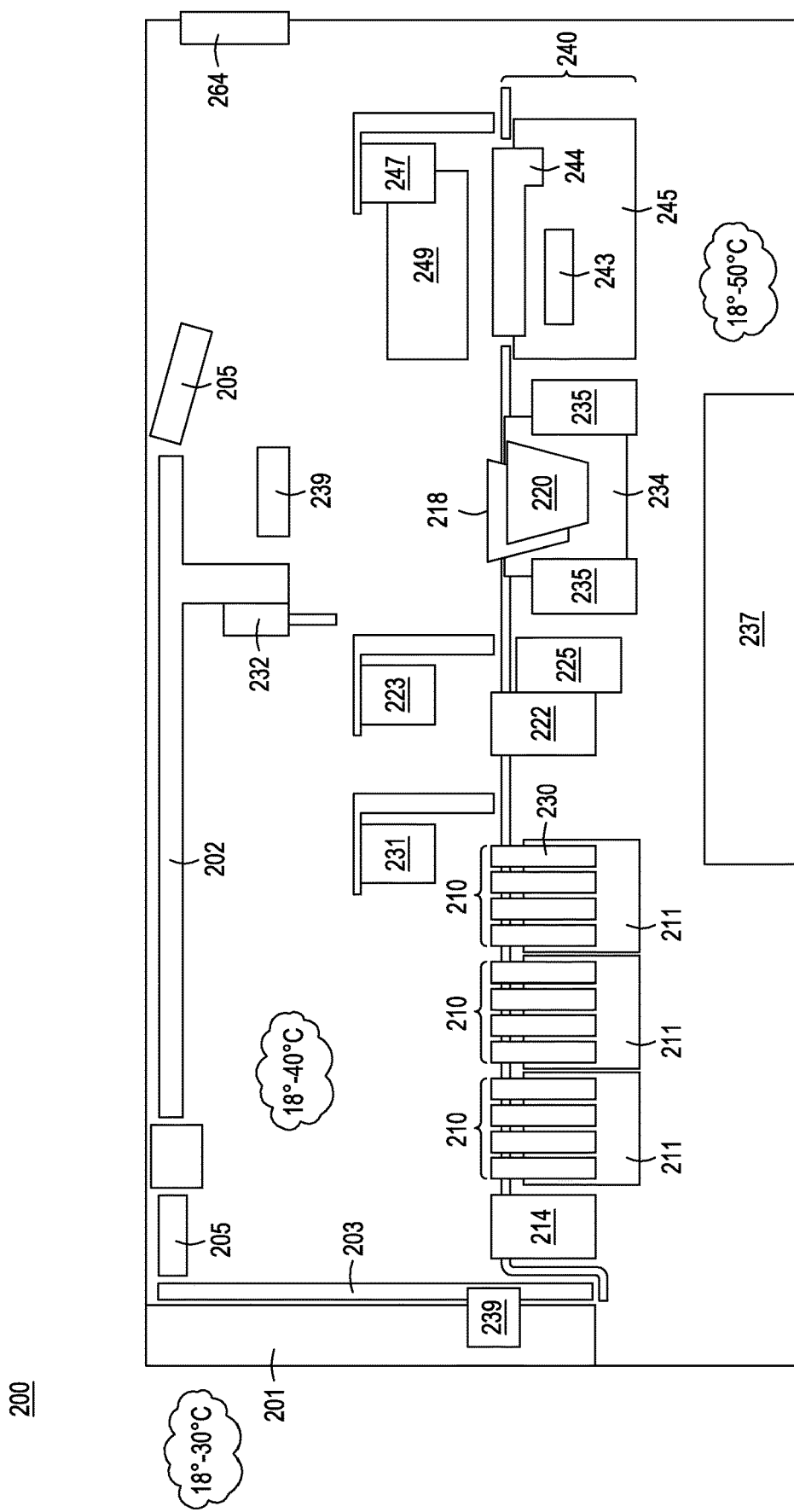

FIG. 2B is a simplified representation of the contents of the exemplary multi-module cell processing instrument 200 depicted in FIG. 2A. Cartridge-based source materials (such as in reagent cartridges 210), for example, may be positioned in designated areas on a deck of the instrument 200 for access by an air displacement pipettor 232 moved by gantry 202 with pipette tips supplied by pipette transfer tip supply 214. The deck of the multi-module cell processing instrument 200 may include a protection sink such that contaminants spilling, dripping, or overflowing from any of the modules of the instrument 200 are contained within a lip of the protection sink. Also seen are reagent cartridges 210, which are shown disposed with thermal assemblies 211 which can create temperature zones appropriate for different regions. Note that one of the reagent cartridges also comprises a flow-through electroporation device 230 (FTEP), served by FTEP interface (e.g., manifold arm) and actuator 231. Also seen is TFF module 222 with adjacent thermal assembly 225, where the TFF module is served by TFF interface (e.g., manifold arm) and actuator 223. Thermal assemblies 225, 235, and 245 encompass thermal electric devices such as Peltier devices, as well as heatsinks, fans and coolers. The rotating growth vial 218 is within a growth module 234, where the growth module is served by two thermal assemblies 235. Selection module is seen at 220. Also seen is the SWIIN module 240, comprising a SWIIN cartridge (not shown), where the SWIIN module also comprises a thermal assembly 245, illumination 243 (in this embodiment, backlighting), evaporation and condensation control 249, SWIIN cover 244, and where the SWIIN module is served by SWIIN interface (e.g., manifold arm) and actuator 247. Also seen in this view is touch screen display 201, display actuator 203, illumination 205 (one on either side of multi-module cell processing instrument 200), cooling grate 264, and cameras 239 (one illumination device on either side of multi-module cell processing instrument 200). Finally, element 237 comprises electronics, such as circuit control boards, high-voltage amplifiers, power supplies, and power entry; as well as pneumatics, such as pumps, valves and sensors.

Figure 2C:
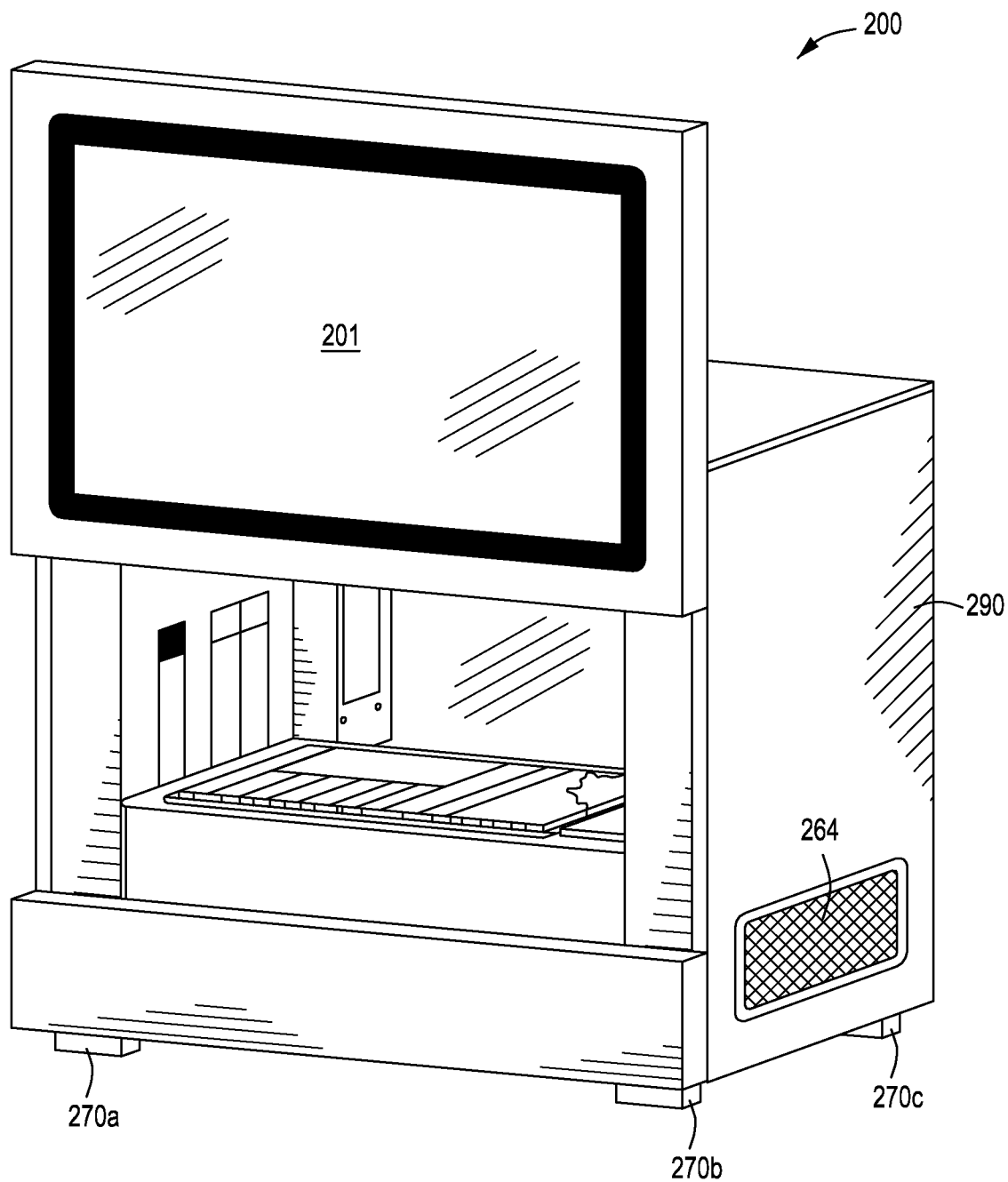

FIG. 2C illustrates a front perspective view of multi-module cell processing instrument 200 for use in as a desktop version of the automated multi-module cell editing instrument 200. For example, a chassis 290 may have a width of about 24-48 inches, a height of about 24-48 inches and a depth of about 24-48 inches. Chassis 290 may be and preferably is designed to hold all modules and disposable supplies used in automated cell processing and to perform all processes required without human intervention; that is, chassis 290 is configured to provide an integrated, stand-alone automated multi-module cell processing instrument. As illustrated in FIG. 2C, chassis 290 includes touch screen display 201, cooling grate 264, which allows for air flow via an internal fan (not shown). The touch screen display provides information to a user regarding the processing status of the automated multi-module cell editing instrument 200 and accepts inputs from the user for conducting the cell processing. In this embodiment, the chassis 290 is lifted by adjustable feet 270a, 270b, 270c and 270d (feet 270a-270c are shown in this FIG. 2C). Adjustable feet 270a-270d, for example, allow for additional air flow beneath the chassis 290.

Inside the chassis 290, in some implementations, will be most or all of the components described in relation to FIGS. 2A and 2B, including the robotic liquid handling system disposed along a gantry, reagent cartridges 210 including a flow-through electroporation device (not shown in this FIG. 2C), a rotating growth vial 218 in a cell growth module 234 (not shown in this FIG. 2C), a tangential flow filtration module 222 (not shown in this FIG. 2C), a SWIIN module 240 as well as interfaces and actuators for the various modules (not shown in this FIG. 2C). In addition, chassis 290 houses control circuitry, liquid handling tubes, air pump controls, valves, sensors, thermal assemblies (e.g., heating and cooling units) and other control mechanisms (not shown in this FIG. 2C). For examples of multi-module cell editing instruments, see U.S. Pat. Nos. 10,253,316; 10,329,559; 10,323,242; 10,421,959; 10,465,185; 10,519,437; 10,584,333; and 10,584,334 and U.S. Ser. Nos. 16/750,369, filed 23 Jan. 2020; 16/822,249, filed 18 Mar. 2020; and 16/837,985, filed 1 Apr. 2020, all of which are herein incorporated by reference in their entirety.

The Rotating Cell Growth Module

Figure 3A:
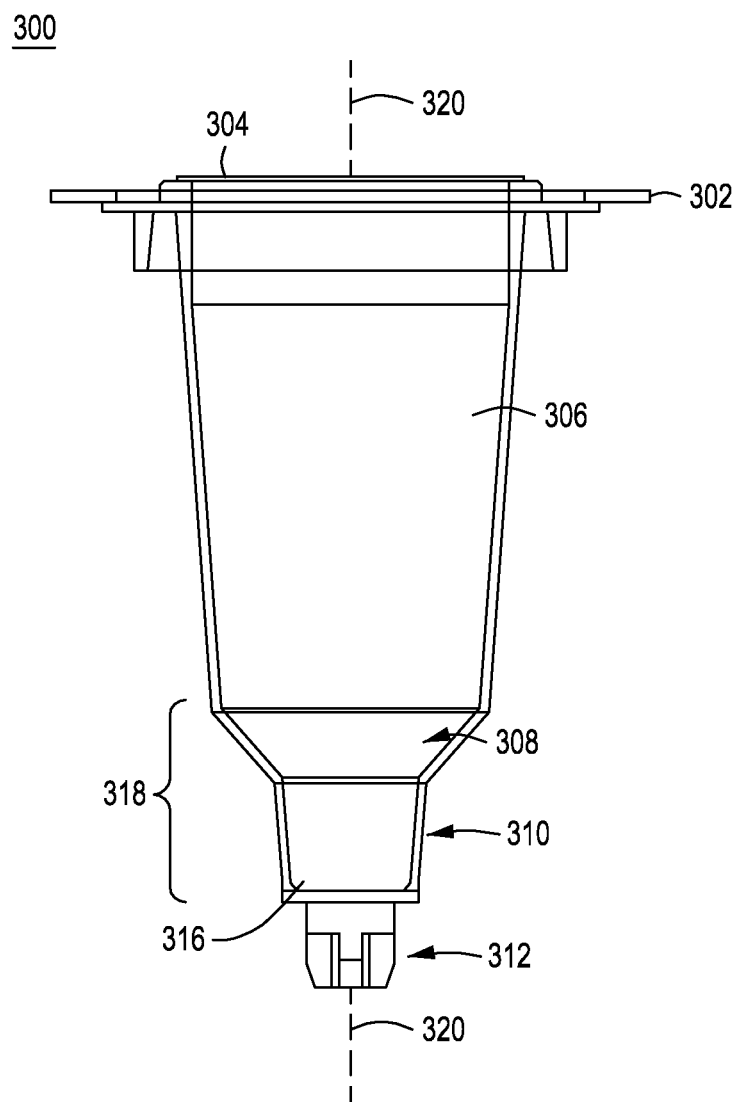
FIG. 3A depicts one embodiment of a rotating growth vial for use with the cell growth module described herein and in relation to FIGS. 3B-3D.

FIG. 3A shows one embodiment of a rotating growth vial 300 for use with the cell growth device and in the automated multi-module cell processing instruments described herein. The rotating growth vial 300 is an optically-transparent container having an open end 304 for receiving liquid media and cells, a central vial region 306 that defines the primary container for growing cells, a tapered-to-constricted region 318 defining at least one light path 310, a closed end 316, and a drive engagement mechanism 312. The rotating growth vial 300 has a central longitudinal axis 320 around which the vial rotates, and the light path 310 is generally perpendicular to the longitudinal axis of the vial. The first light path 310 is positioned in the lower constricted portion of the tapered-to-constricted region 318. Optionally, some embodiments of the rotating growth vial 300 have a second light path 308 in the tapered region of the tapered-to-constricted region 318. Both light paths in this embodiment are positioned in a region of the rotating growth vial that is constantly filled with the cell culture (cells+growth media) and are not affected by the rotational speed of the growth vial. The first light path 310 is shorter than the second light path 308 allowing for sensitive measurement of OD values when the OD values of the cell culture in the vial are at a high level (e.g., later in the cell growth process), whereas the second light path 308 allows for sensitive measurement of OD values when the OD values of the cell culture in the vial are at a lower level (e.g., earlier in the cell growth process).

The drive engagement mechanism 312 engages with a motor (not shown) to rotate the vial. In some embodiments, the motor drives the drive engagement mechanism 312 such that the rotating growth vial 300 is rotated in one direction only, and in other embodiments, the rotating growth vial 300 is rotated in a first direction for a first amount of time or periodicity, rotated in a second direction (i.e., the opposite direction) for a second amount of time or periodicity, and this process may be repeated so that the rotating growth vial 300 (and the cell culture contents) are subjected to an oscillating motion. Further, the choice of whether the culture is subjected to oscillation and the periodicity therefor may be selected by the user. The first amount of time and the second amount of time may be the same or may be different. The amount of time may be 1, 2, 3, 4, 5, or more seconds, or may be 1, 2, 3, 4 or more minutes. In another embodiment, in an early stage of cell growth the rotating growth vial 300 may be oscillated at a first periodicity (e.g., every 60 seconds), and then a later stage of cell growth the rotating growth vial 300 may be oscillated at a second periodicity (e.g., every one second) different from the first periodicity.

The rotating growth vial 300 may be reusable or, preferably, the rotating growth vial is consumable. In some embodiments, the rotating growth vial is consumable and is presented to the user pre-filled with growth medium, where the vial is hermetically sealed at the open end 304 with a foil seal. A medium-filled rotating growth vial packaged in such a manner may be part of a kit for use with a stand-alone cell growth device or with a cell growth module that is part of an automated multi-module cell processing system. To introduce cells into the vial, a user need only pipette up a desired volume of cells and use the pipette tip to punch through the foil seal of the vial. Open end 304 may optionally include an extended lip 302 to overlap and engage with the cell growth device. In automated systems, the rotating growth vial 300 may be tagged with a barcode or other identifying means that can be read by a scanner or camera (not shown) that is part of the automated system.

The volume of the rotating growth vial 300 and the volume of the cell culture (including growth medium) may vary greatly, but the volume of the rotating growth vial 300 must be large enough to generate a specified total number of cells. In practice, the volume of the rotating growth vial 300 may range from 1-250 mL, 2-100 mL, from 5-80 mL, 10-50 mL, or from 12-35 mL. Likewise, the volume of the cell culture (cells+growth media) should be appropriate to allow proper aeration and mixing in the rotating growth vial 300. Proper aeration promotes uniform cellular respiration within the growth media. Thus, the volume of the cell culture should be approximately 5-85% of the volume of the growth vial or from 20-60% of the volume of the growth vial. For example, for a 30 mL growth vial, the volume of the cell culture would be from about 1.5 mL to about 26 mL, or from 6 mL to about 18 mL.

The rotating growth vial 300 preferably is fabricated from a bio-compatible optically transparent material—or at least the portion of the vial comprising the light path(s) is transparent. Additionally, material from which the rotating growth vial is fabricated should be able to be cooled to about 4° C. or lower and heated to about 55° C. or higher to accommodate both temperature-based cell assays and long-term storage at low temperatures. Further, the material that is used to fabricate the vial must be able to withstand temperatures up to 55° C. without deformation while spinning. Suitable materials include cyclic olefin copolymer (COC), glass, polyvinyl chloride, polyethylene, polyamide, polypropylene, polycarbonate, poly(methyl methacrylate (PMMA), polysulfone, polyurethane, and co-polymers of these and other polymers. Preferred materials include polypropylene, polycarbonate, or polystyrene. In some embodiments, the rotating growth vial is inexpensively fabricated by, e.g., injection molding or extrusion.

Figure 3B:
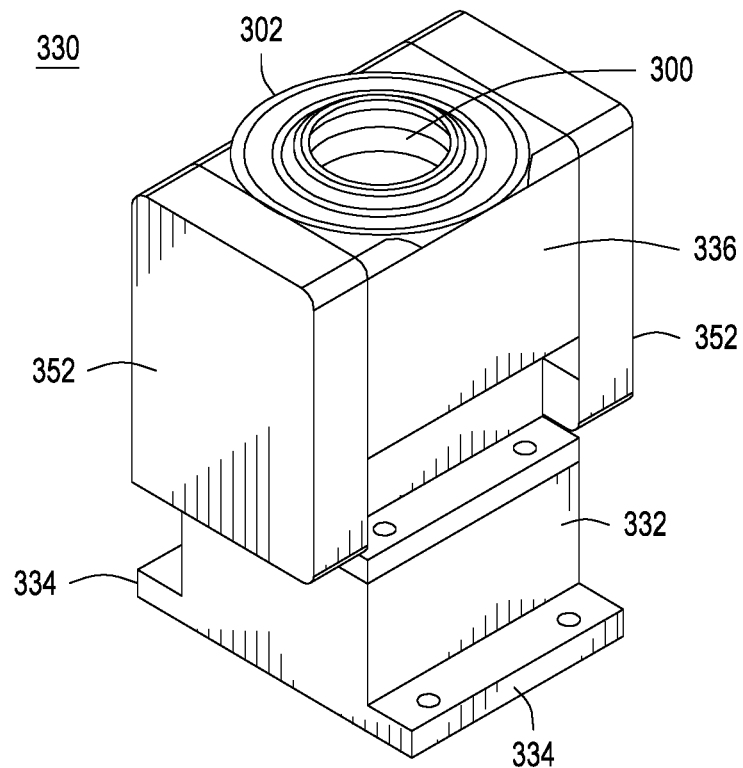
FIG. 3B illustrates a perspective view of one embodiment of a rotating growth vial in a cell growth module housing.
Figure 3C:
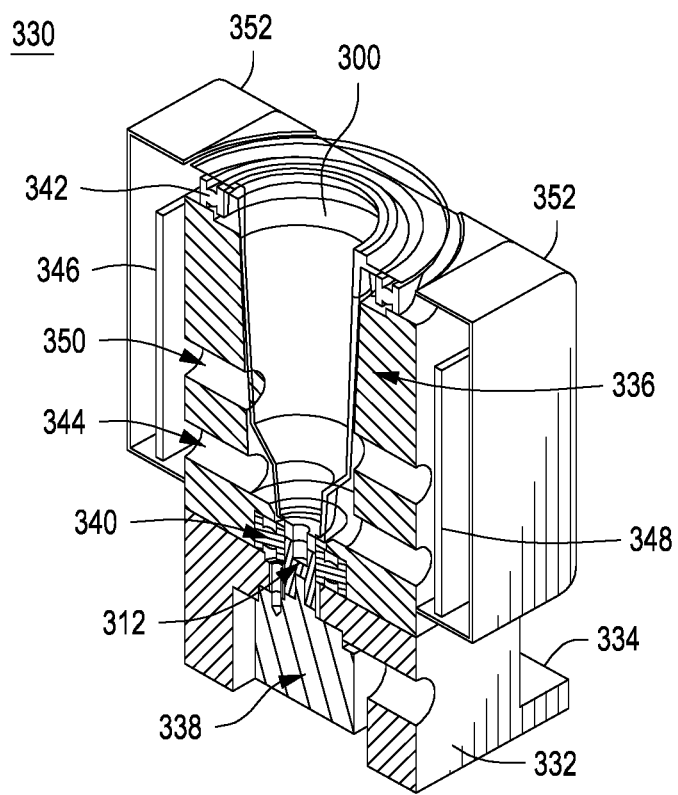
FIG. 3C depicts a cut-away view of the cell growth module from FIG. 3B.

FIG. 3B is a perspective view of one embodiment of a cell growth device 330. FIG. 3C depicts a cut-away view of the cell growth device 330 from FIG. 3B. In both figures, the rotating growth vial 300 is seen positioned inside a main housing 336 with the extended lip 302 of the rotating growth vial 300 extending above the main housing 336. Additionally, end housings 352, a lower housing 332 and flanges 334 are indicated in both figures. Flanges 334 are used to attach the cell growth device 330 to heating/cooling means or other structure (not shown). FIG. 3C depicts additional detail. In FIG. 3C, upper bearing 342 and lower bearing 340 are shown positioned within main housing 336. Upper bearing 342 and lower bearing 340 support the vertical load of rotating growth vial 300. Lower housing 332 contains the drive motor 338. The cell growth device 330 of FIG. 3C comprises two light paths: a primary light path 344, and a secondary light path 350. Light path 344 corresponds to light path 310 positioned in the constricted portion of the tapered-to-constricted portion of the rotating growth vial 300, and light path 350 corresponds to light path 308 in the tapered portion of the tapered-to-constricted portion of the rotating growth via 316. Light paths 310 and 308 are not shown in FIG. 3C but may be seen in FIG. 3A. In addition to light paths 344 and 340, there is an emission board 348 to illuminate the light path(s), and detector board 346 to detect the light after the light travels through the cell culture liquid in the rotating growth vial 300.

The motor 338 engages with drive mechanism 312 and is used to rotate the rotating growth vial 300. In some embodiments, motor 338 is a brushless DC type drive motor with built-in drive controls that can be set to hold a constant revolution per minute (RPM) between 0 and about 3000 RPM. Alternatively, other motor types such as a stepper, servo, brushed DC, and the like can be used. Optionally, the motor 338 may also have direction control to allow reversing of the rotational direction, and a tachometer to sense and report actual RPM. The motor is controlled by a processor (not shown) according to, e.g., standard protocols programmed into the processor and/or user input, and the motor may be configured to vary RPM to cause axial precession of the cell culture thereby enhancing mixing, e.g., to prevent cell aggregation, increase aeration, and optimize cellular respiration.

Main housing 336, end housings 352 and lower housing 332 of the cell growth device 330 may be fabricated from any suitable, robust material including aluminum, stainless steel, and other thermally conductive materials, including plastics. These structures or portions thereof can be created through various techniques, e.g., metal fabrication, injection molding, creation of structural layers that are fused, etc. Whereas the rotating growth vial 300 is envisioned in some embodiments to be reusable, but preferably is consumable, the other components of the cell growth device 330 are preferably reusable and function as a stand-alone benchtop device or as a module in a multi-module cell processing system.

The processor (not shown) of the cell growth device 330 may be programmed with information to be used as a "blank" or control for the growing cell culture. A "blank" or control is a vessel containing cell growth medium only, which yields 100% transmittance and 0 OD, while the cell sample will deflect light rays and will have a lower percent transmittance and higher OD. As the cells grow in the media and become denser, transmittance will decrease and OD will increase. The processor (not shown) of the cell growth device 330—may be programmed to use wavelength values for blanks commensurate with the growth media typically used in cell culture (whether, e.g., mammalian cells, bacterial cells, animal cells, yeast cells, etc.). Alternatively, a second spectrophotometer and vessel may be included in the cell growth device 330, where the second spectrophotometer is used to read a blank at designated intervals.

Figure 3D:
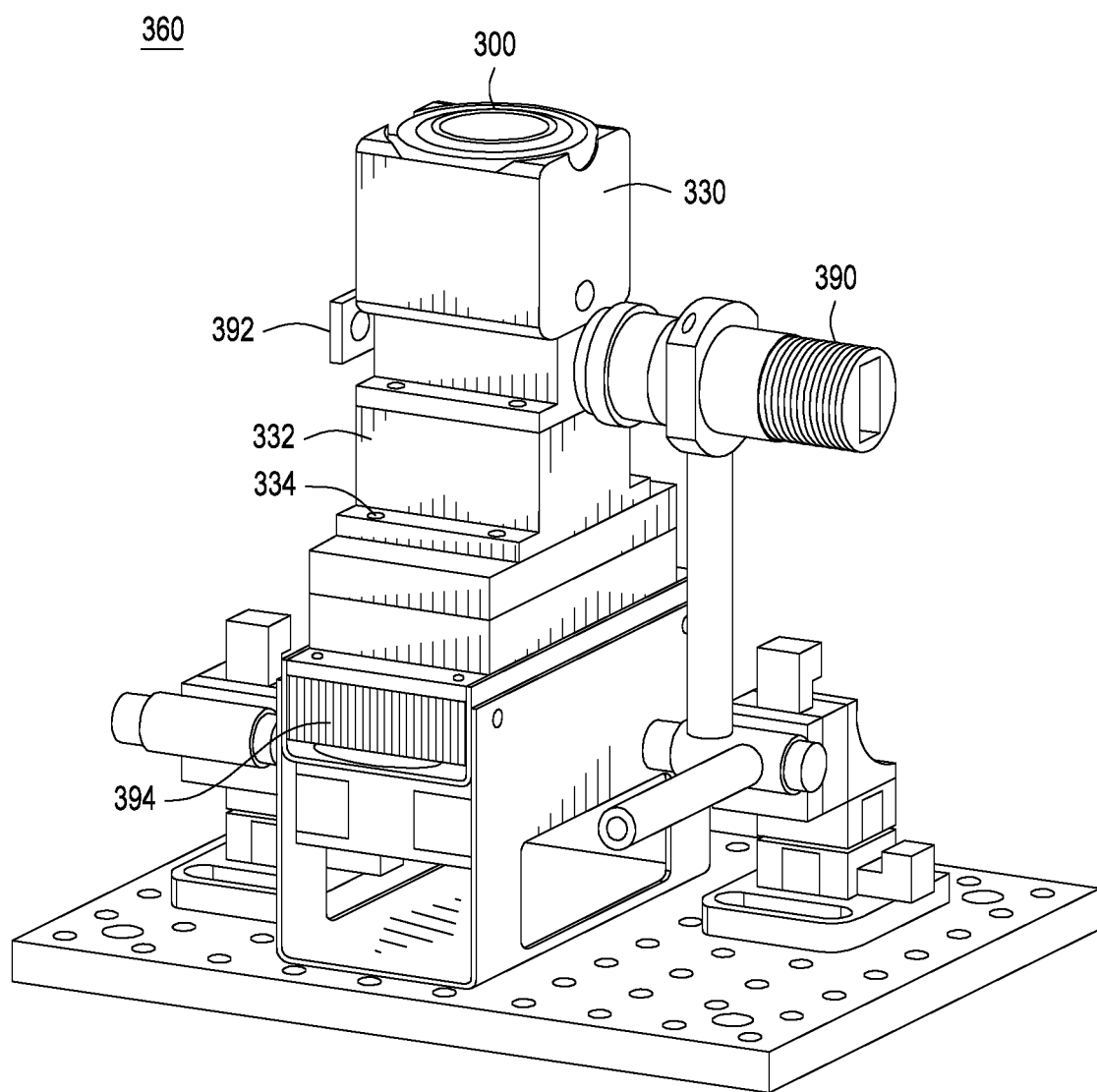
FIG. 3D illustrates the cell growth module of FIG. 3B coupled to LED, detector, and temperature regulating components.

FIG. 3D illustrates a cell growth device 330 as part of an assembly 360 comprising the cell growth device 330 of FIG. 3B coupled to light source 390, detector 392, and thermal components 394. The rotating growth vial 300 is inserted into the cell growth device. Components of the light source 390 and detector 392 (e.g., such as a photodiode with gain control to cover 5-log) are coupled to the main housing of the cell growth device. The lower housing 332 that houses the motor that rotates the rotating growth vial 300 is illustrated, as is one of the flanges 334 that secures the cell growth device 330 to the assembly. Also, the thermal components 394 illustrated are a Peltier device or thermoelectric cooler. In this embodiment, thermal control is accomplished by attachment and electrical integration of the cell growth device 330 to the thermal components 394 via the flange 334 on the base of the lower housing 332. Thermoelectric coolers are capable of "pumping" heat to either side of a junction, either cooling a surface or heating a surface depending on the direction of current flow. In one embodiment, a thermistor is used to measure the temperature of the main housing and then, through a standard electronic proportional-integral-derivative (PID) controller loop, the rotating growth vial 300 is controlled to approximately +/− 0.5° C.

In use, cells are inoculated (cells can be pipetted, e.g., from an automated liquid handling system or by a user) into pre-filled growth media of a rotating growth vial 300 by piercing though the foil seal or film. The programmed software of the cell growth device 330 sets the control temperature for growth, typically 30° C., then slowly starts the rotation of the rotating growth vial 300. The cell/growth media mixture slowly moves vertically up the wall due to centrifugal force allowing the rotating growth vial 300 to expose a large surface area of the mixture to a normal oxygen environment. The growth monitoring system takes either continuous readings of the OD or OD measurements at pre-set or pre-programmed time intervals. These measurements are stored in internal memory and if requested the software plots the measurements versus time to display a growth curve. If enhanced mixing is required, e.g., to optimize growth conditions, the speed of the vial rotation can be varied to cause an axial precession of the liquid, and/or a complete directional change can be performed at programmed intervals. The growth monitoring can be programmed to automatically terminate the growth stage at a pre-determined OD, and then quickly cool the mixture to a lower temperature to inhibit further growth.

One application for the cell growth device 330 is to constantly measure the optical density of a growing cell culture. One advantage of the described cell growth device is that optical density can be measured continuously (kinetic monitoring) or at specific time intervals; e.g., every 5, 10, 15, 20, 30 45, or 60 seconds, or every 1, 2, 3, 4, 5, 6, 7, 8, 9, or 10 minutes. While the cell growth device 330 has been described in the context of measuring the optical density (OD) of a growing cell culture, it should, however, be understood by a skilled artisan given the teachings of the present specification that other cell growth parameters can be measured in addition to or instead of cell culture OD. As with optional measure of cell growth in relation to the solid wall device or module described supra, spectroscopy using visible, UV, or near infrared (NIR) light allows monitoring the concentration of nutrients and/or wastes in the cell culture and other spectroscopic measurements may be made; that is, other spectral properties can be measured via, e.g., dielectric impedance spectroscopy, visible fluorescence, fluorescence polarization, or luminescence. Additionally, the cell growth device 330 may include additional sensors for measuring, e.g., dissolved oxygen, carbon dioxide, pH, conductivity, and the like. For additional details regarding rotating growth vials and cell growth devices see U.S. Pat. Nos. 10,435,662; 10,443,031; 10,590,375 and U.S. Ser. No. 16/780,640, filed 3 Feb. 2020.

The Cell Concentration Module

As described above in relation to the rotating growth vial and cell growth module, in order to obtain an adequate number of cells for transformation or transfection, cells typically are grown to a specific optical density in medium appropriate for the growth of the cells of interest; however, for effective transformation or transfection, it is desirable to decrease the volume of the cells as well as render the cells competent via buffer or medium exchange. Thus, one subcomponent or module that is desired in cell processing systems for the processes listed above is a module or component that can grow, perform buffer exchange, and/or concentrate cells and render them competent so that they may be transformed or transfected with the nucleic acids needed for engineering or editing the cell's genome.

Figure 4A:
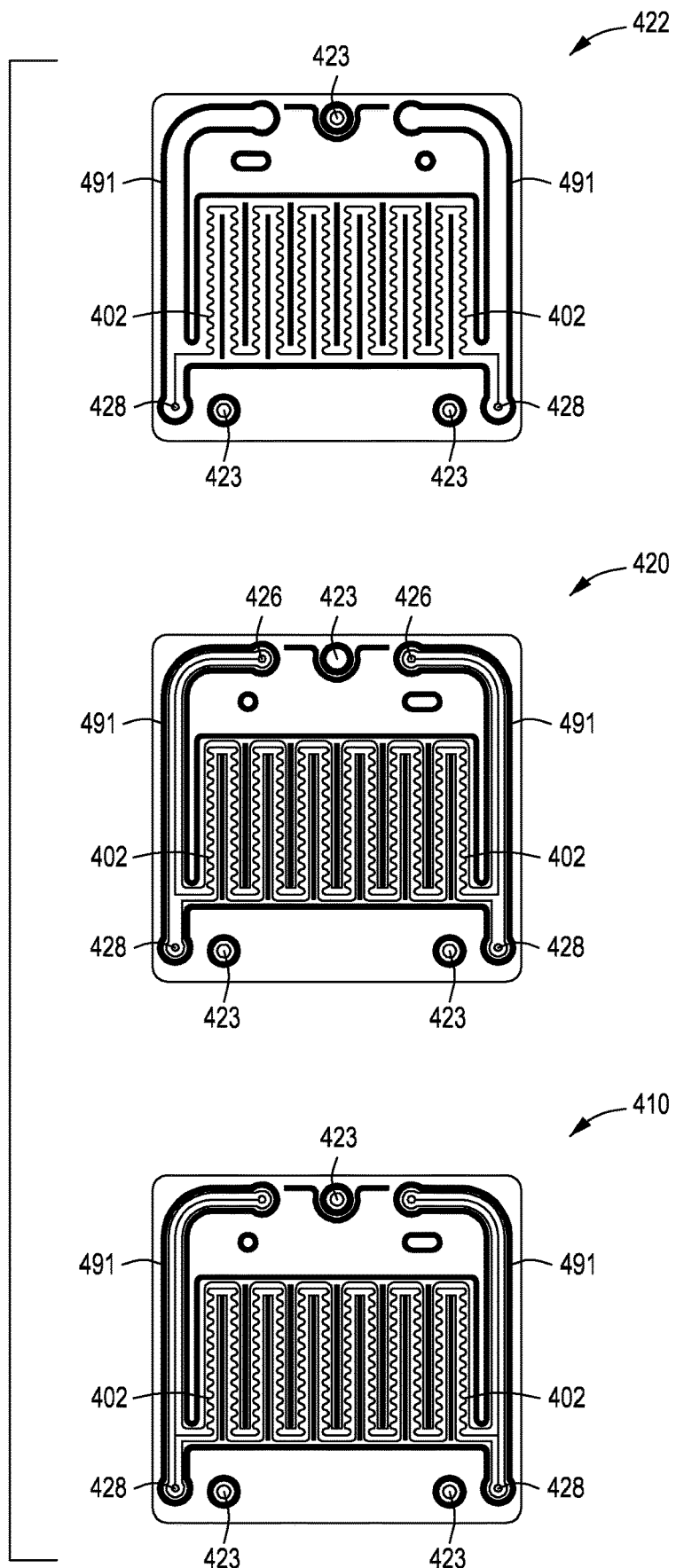
FIG. 4A depicts retentate (top) and permeate (middle) members for use in a tangential flow filtration module (e.g., cell growth and/or concentration module), as well as the retentate and permeate members assembled into a tangential flow assembly (bottom).

FIG. 4A shows a retentate member 422 (top), permeate member 420 (middle) and a tangential flow assembly 410 (bottom) comprising the retentate member 422, membrane 424 (not seen in FIG. 4A), and permeate member 420 (also not seen). In FIG. 4A, retentate member 422 comprises a tangential flow channel 402, which has a serpentine configuration that initiates at one lower corner of retentate member 422—specifically at retentate port 428—traverses across and up then down and across retentate member 422, ending in the other lower corner of retentate member 422 at a second retentate port 428. Also seen on retentate member 422 are energy directors 491, which circumscribe the region where a membrane or filter (not seen in this FIG. 4A) is seated, as well as interdigitate between areas of channel 402. Energy directors 491 in this embodiment mate with and serve to facilitate ultrasonic welding or bonding of retentate member 422 with permeate/filtrate member 420 via the energy director component 491 on permeate/filtrate member 420 (at right). Additionally, countersinks 423 can be seen, two on the bottom one at the top middle of retentate member 422. Countersinks 423 are used to couple and tangential flow assembly 410 to a reservoir assembly (not seen in this FIG. 4A but see FIG. 4B).

Permeate/filtrate member 420 is seen in the middle of FIG. 4A and comprises, in addition to energy director 491, through-holes for retentate ports 428 at each bottom corner (which mate with the through-holes for retentate ports 428 at the bottom corners of retentate member 422), as well as a tangential flow channel 402 and two permeate/filtrate ports 426 positioned at the top and center of permeate member 420. The tangential flow channel 402 structure in this embodiment has a serpentine configuration and an undulating geometry, although other geometries may be used. Permeate member 420 also comprises countersinks 423, coincident with the countersinks 423 on retentate member 420.

At bottom of FIG. 4A is a tangential flow assembly 410 comprising the retentate member 422 and permeate member 420 seen in this FIG. 4A. In this view, retentate member 422 is "on top" of the view, a membrane (not seen in this view of the assembly) would be adjacent and under retentate member 422 and permeate member 420 (also not seen in this view of the assembly) is adjacent to and beneath the membrane. Again countersinks 423 are seen, where the countersinks in the retentate member 422 and the permeate member 420 are coincident and configured to mate with threads or mating elements for the countersinks disposed on a reservoir assembly (not seen in FIG. 4A but see FIG. 4B).

A membrane or filter is disposed between the retentate and permeate members, where fluids can flow through the membrane but cells cannot and are thus retained in the flow channel disposed in the retentate member. Filters or membranes appropriate for use in the TFF device/module are those that are solvent resistant, are contamination free during filtration, and are able to retain the types and sizes of cells of interest. For example, in order to retain small cell types such as bacterial cells, pore sizes can be as low as 0.2 µm, however for other cell types, the pore sizes can be as high as 20 µm. Indeed, the pore sizes useful in the TFF device/module include filters with sizes from 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters may be fabricated from any suitable non-reactive material including cellulose mixed ester (cellulose nitrate and acetate) (CME), polycarbonate (PC), polyvinylidene fluoride (PVDF), polyethersulfone (PES), polytetrafluoroethylene (PTFE), nylon, glass fiber, or metal substrates as in the case of laser or electrochemical etching.

The length of the channel structure 402 may vary depending on the type and volume of the cell culture to be grown and the optical density of the cell culture to be concentrated. The length of the channel structure typically is from 60 mm to 300 mm, or from 70 mm to 200 mm, or from 80 mm to 100 mm. The cross-section configuration of the flow channel 402 may be round, elliptical, oval, square, rectangular, trapezoidal, or irregular. If square, rectangular, or another shape with generally straight sides, the cross section may be from about 10 µm to 1000 µm wide, or from 200 µm to 800 µm wide, or from 300 µm to 700 µm wide, or from 400 µm to 600 µm wide; and from about 10 µm to 1000 µm high, or from 200 µm to 800 µm high, or from 300 µm to 700 µm high, or from 400 µm to 600 µm high. If the cross section of the flow channel 402 is generally round, oval or elliptical, the radius of the channel may be from about 50 µm to 1000 µm in hydraulic radius, or from 5µm to 800 µm in hydraulic radius, or from 200 µm to 700 µm in hydraulic radius, or from 300 µm to 600 µm wide in hydraulic radius, or from about 200 to 500 µm in hydraulic radius. Moreover, the volume of the channel in the retentate 422 and permeate 420 members may be different depending on the depth of the channel in each member.

Figure 4B:
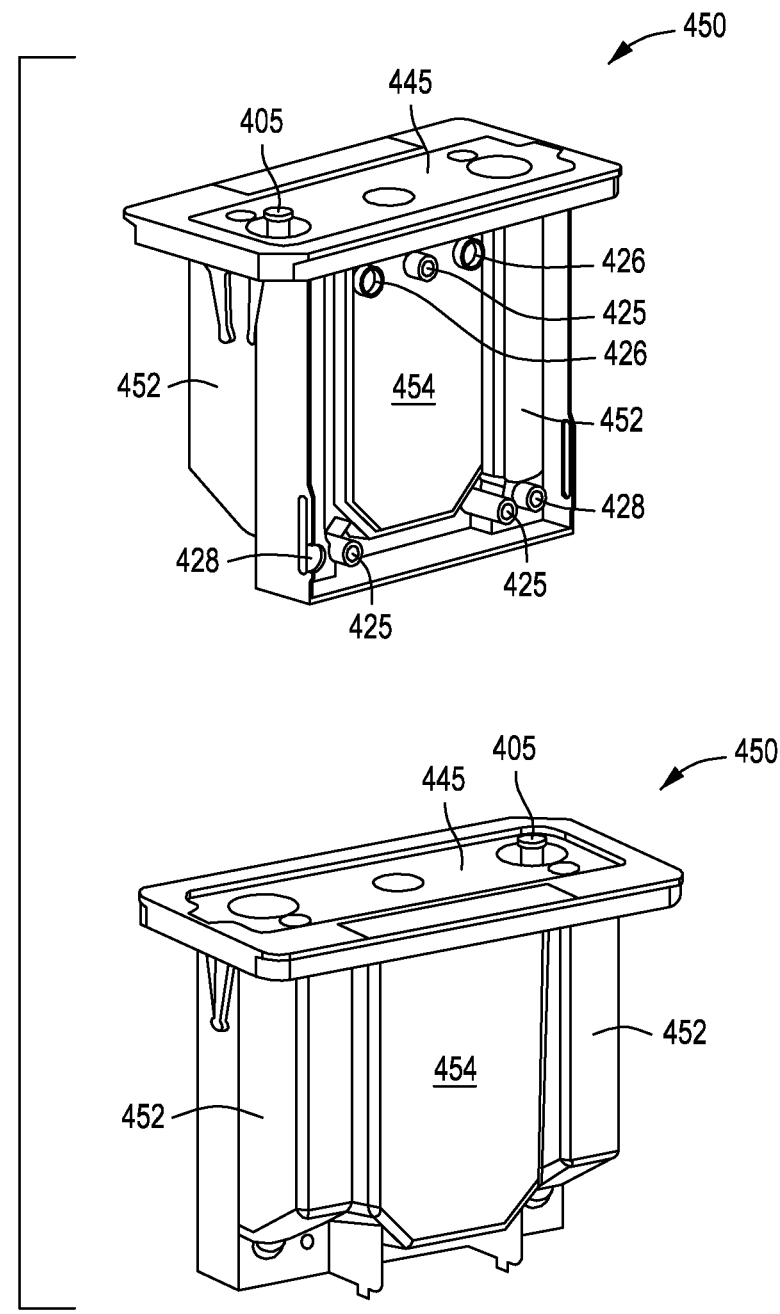
FIG. 4B depicts two side perspective views of a reservoir assembly of a tangential flow filtration module.

FIG. 4B shows front perspective (top) and rear perspective (bottom) views of a reservoir assembly 450 configured to be used with the tangential flow assembly 410 seen in FIG. 4A. Seen in the front perspective view (e.g., "front" being the side of reservoir assembly 450 that is coupled to the tangential flow assembly 410 seen in FIG. 4A) are retentate reservoirs 452 on either side of permeate reservoir 454. Also seen are permeate ports 426, retentate ports 428, and three threads or mating elements 425 for countersinks 423 (countersinks 423 not seen in this FIG. 4B). Threads or mating elements 425 for countersinks 423 are configured to mate or couple the tangential flow assembly 410 (seen in FIG. 4A) to reservoir assembly 450. Alternatively or in addition, fasteners, sonic welding or heat stakes may be used to mate or couple the tangential flow assembly 410 to reservoir assembly 450. In addition is seen gasket 445 covering the top of reservoir assembly 450, with pipette tip 405 shown inserted into the left-most retentate reservoir. Gasket 445 is described in detail in relation to FIG. 4E. At left in FIG. 4B is a rear perspective view of reservoir assembly 450, where "rear" is the side of reservoir assembly 450 that is not coupled to the tangential flow assembly. Seen are retentate reservoirs 452, permeate reservoir 454, gasket 445, with pipette tip 405 shown inserted into the right-most retentate reservoir.

The TFF device may be fabricated from any robust material in which channels (and channel branches) may be milled including stainless steel, silicon, glass, aluminum, or plastics including cyclic-olefin copolymer (COC), cyclo-olefin polymer (COP), polystyrene, polyvinyl chloride, polyethylene, polyamide, polyethylene, polypropylene, acrylonitrile butadiene, polycarbonate, polyetheretheketone (PEEK), poly(methyl methylacrylate) (PMMA), polysulfone, and polyurethane, and co-polymers of these and other polymers. If the TFF device/module is disposable, preferably it is made of plastic. In some embodiments, the material used to fabricate the TFF device/module is thermally-conductive so that the cell culture may be heated or cooled to a desired temperature. In certain embodiments, the TFF device is formed by precision mechanical machining, laser machining, electro discharge machining (for metal devices); wet or dry etching (for silicon devices); dry or wet etching, powder or sandblasting, photostructuring (for glass devices); or thermoforming, injection molding, hot embossing, or laser machining (for plastic devices) using the materials mentioned above that are amenable to this mass production techniques.

Figure 4C:
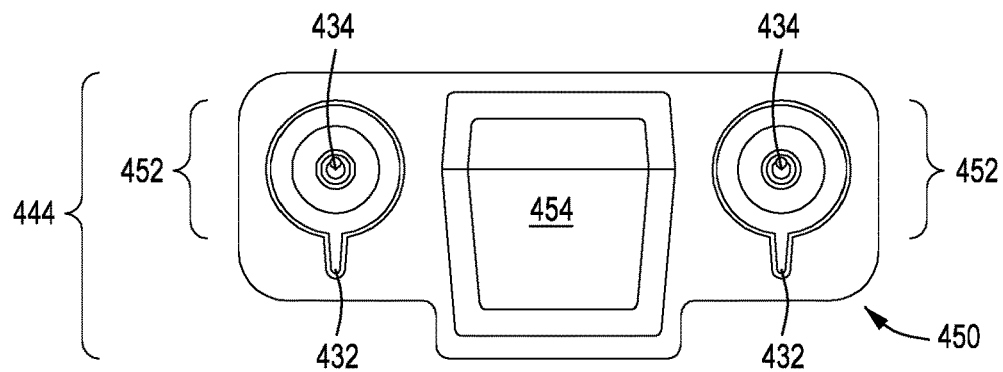
FIGS. 4C-4E depict an exemplary top, with fluidic and pneumatic ports and gasket suitable for the reservoir assemblies shown in FIG. 4B.
Figure 4D:
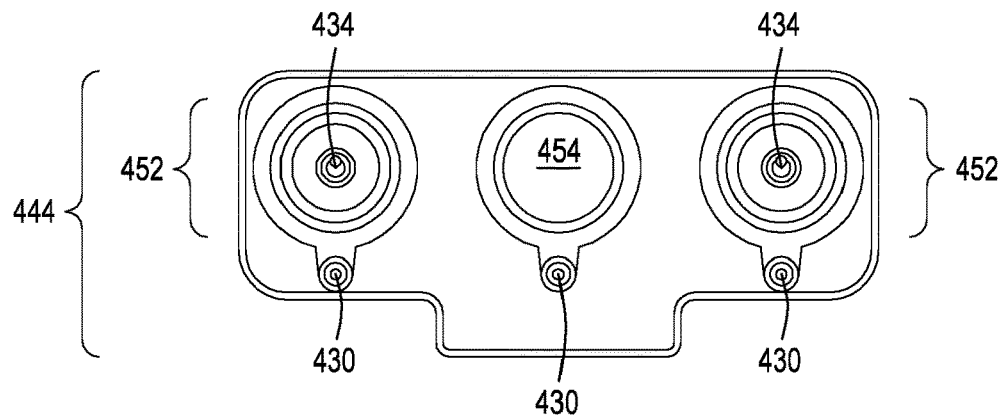
Figure 4E:
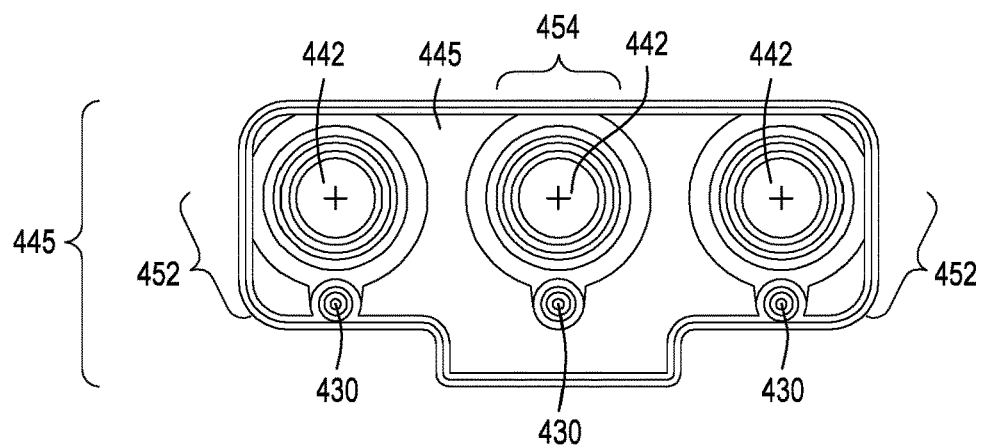

FIG. 4C depicts a top-down view of the reservoir assemblies 450 shown in FIG. 4B. FIG. 4D depicts a cover 444 for reservoir assembly 450 shown in FIG. 4B and 4E depicts a gasket 445 that in operation is disposed on cover 444 of reservoir assemblies 450 shown in FIG. 4B. FIG. 4C is a top-down view of reservoir assembly 450, showing the tops of the two retentate reservoirs 452, one on either side of permeate reservoir 454. Also seen are grooves 432 that will mate with a pneumatic port (not shown), and fluid channels 434 that reside at the bottom of retentate reservoirs 452, which fluidically couple the retentate reservoirs 452 with the retentate ports 428 (not shown), via the through-holes for the retentate ports in permeate member 420 and membrane 424 (also not shown). FIG. 4D depicts a cover 444 that is configured to be disposed upon the top of reservoir assembly 450. Cover 444 has round cut-outs at the top of retentate reservoirs 452 and permeate/filtrate reservoir 454. Again at the bottom of retentate reservoirs 452 fluid channels 434 can be seen, where fluid channels 434 fluidically couple retentate reservoirs 452 with the retentate ports 428 (not shown). Also shown are three pneumatic ports 430 for each retentate reservoir 452 and permeate/filtrate reservoir 454. FIG. 4E depicts a gasket 445 that is configured to be disposed upon the cover 444 of reservoir assembly 450. Seen are three fluid transfer ports 442 for each retentate reservoir 452 and for permeate/filtrate reservoir 454. Again, three pneumatic ports 430, for each retentate reservoir 452 and for permeate/filtrate reservoir 454, are shown.

The overall work flow for cell growth comprises loading a cell culture to be grown into a first retentate reservoir, optionally bubbling air or an appropriate gas through the cell culture, passing or flowing the cell culture through the first retentate port then tangentially through the TFF channel structure while collecting medium or buffer through one or both of the permeate ports 426, collecting the cell culture through a second retentate port 428 into a second retentate reservoir, optionally adding additional or different medium to the cell culture and optionally bubbling air or gas through the cell culture, then repeating the process, all while measuring, e.g., the optical density of the cell culture in the retentate reservoirs continuously or at desired intervals. Measurements of optical densities (OD) at programmed time intervals are accomplished using a 600 nm Light Emitting Diode (LED) that has been columnated through an optic into the retentate reservoir(s) containing the growing cells. The light continues through a collection optic to the detection system which consists of a (digital) gain-controlled silicone photodiode. Generally, optical density is shown as the absolute value of the logarithm with base 10 of the power transmission factors of an optical attenuator: OD=−log 10 (Power out/Power in). Since OD is the measure of optical attenuation—that is, the sum of absorption, scattering, and reflection—the TFF device OD measurement records the overall power transmission, so as the cells grow and become denser in population, the OD (the loss of signal) increases. The OD system is pre-calibrated against OD standards with these values stored in an on-board memory accessible by the measurement program.

In the channel structure, the membrane bifurcating the flow channels retains the cells on one side of the membrane (the retentate side 422) and allows unwanted medium or buffer to flow across the membrane into a filtrate or permeate side (e.g., permeate member 420) of the device. Bubbling air or other appropriate gas through the cell culture both aerates and mixes the culture to enhance cell growth. During the process, medium that is removed during the flow through the channel structure is removed through the permeate/filtrate ports 406. Alternatively, cells can be grown in one reservoir with bubbling or agitation without passing the cells through the TFF channel from one reservoir to the other.

The overall work flow for cell concentration using the TFF device/module involves flowing a cell culture or cell sample tangentially through the channel structure. As with the cell growth process, the membrane bifurcating the flow channels retains the cells on one side of the membrane and allows unwanted medium or buffer to flow across the membrane into a permeate/filtrate side (e.g., permeate member 420) of the device. In this process, a fixed volume of cells in medium or buffer is driven through the device until the cell sample is collected into one of the retentate ports 428, and the medium/buffer that has passed through the membrane is collected through one or both of the permeate/filtrate ports 426. All types of prokaryotic and eukaryotic cells—both adherent and non-adherent cells—can be grown in the TFF device. Adherent cells may be grown on beads or other cell scaffolds suspended in medium that flow through the TFF device.

The medium or buffer used to suspend the cells in the cell concentration device/module may be any suitable medium or buffer for the type of cells being transformed or transfected, such as LB, SOC, TPD, YPG, YPAD, MEM, DMEM, IMDM, RPMI, Hanks', PBS and Ringer's solution, where the media may be provided in a reagent cartridge as part of a kit.

In both the cell growth and concentration processes, passing the cell sample through the TFF device and collecting the cells in one of the retentate ports 404 while collecting the medium in one of the permeate/filtrate ports 406 is considered "one pass" of the cell sample. The transfer between retentate reservoirs "flips" the culture. The retentate and permeatee ports collecting the cells and medium, respectively, for a given pass reside on the same end of TFF device/module with fluidic connections arranged so that there are two distinct flow layers for the retentate and permeate/filtrate sides, but if the retentate port 404 resides on the retentate member of device/module (that is, the cells are driven through the channel above the membrane and the filtrate (medium) passes to the portion of the channel below the membrane), the permeate/filtrate port 406 will reside on the permeate member of device/module and vice versa (that is, if the cell sample is driven through the channel below the membrane, the filtrate (medium) passes to the portion of the channel above the membrane). Due to the high pressures used to transfer the cell culture and fluids through the flow channel of the TFF device, the effect of gravity is negligible.

At the conclusion of a "pass" in either of the growth and concentration processes, the cell sample is collected by passing through the retentate port 428 and into the retentate reservoir (not shown). To initiate another "pass", the cell sample is passed again through the TFF device, this time in a flow direction that is reversed from the first pass. The cell sample is collected by passing through the retentate port 428 and into retentate reservoir (not shown) on the opposite end of the device/module from the retentate port 428 that was used to collect cells during the first pass. Likewise, the medium/buffer that passes through the membrane on the second pass is collected through the permeate port 426 on the opposite end of the device/module from the permeate port 426 that was used to collect the filtrate during the first pass, or through both ports. This alternating process of passing the retentate (the concentrated cell sample) through the device/module is repeated until the cells have been grown to a desired optical density, and/or concentrated to a desired volume, and both permeate ports (i.e., if there are more than one) can be open during the passes to reduce operating time. In addition, buffer exchange may be effected by adding a desired buffer (or fresh medium) to the cell sample in the retentate reservoir, before initiating another "pass", and repeating this process until the old medium or buffer is diluted and filtered out and the cells reside in fresh medium or buffer. Note that buffer exchange and cell growth may (and typically do) take place simultaneously, and buffer exchange and cell concentration may (and typically do) take place simultaneously. For further information and alternative embodiments on TFFs see, e.g., U.S. Ser. No. 16/798,302, filed 22 Feb. 2020.

Nucleic Acid Assembly Module

Certain embodiments of the automated multi-module cell editing instruments of the present disclosure optionally include a nucleic acid assembly module. The nucleic acid assembly module is configured to accept and assemble the nucleic acids necessary to facilitate the desired genome editing events. In general, the term "vector" refers to a nucleic acid molecule capable of transporting a desired nucleic acid to which it has been linked into a cell. Vectors include, but are not limited to, nucleic acid molecules that are single-stranded, double-stranded, or partially double-stranded; nucleic acid molecules that include one or more free ends, no free ends (e.g., circular); nucleic acid molecules that include DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, where virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors" or "editing vectors." Common expression vectors of utility in recombinant DNA techniques are often in the form of plasmids. Additional vectors include fosmids, phagemids, and synthetic chromosomes.

Recombinant expression vectors can include a nucleic acid in a form suitable for transcription, and for some nucleic acid sequences, translation and expression of the nucleic acid in a host cell, which means that the recombinant expression vectors include one or more regulatory elements—which may be selected on the basis of the host cells to be used for expression—that are operatively-linked to the nucleic acid sequence to be expressed. Within a recombinant expression vector, "operably linked" is intended to mean that the nucleotide sequence of interest is linked to the regulatory element(s) in a manner that allows for transcription, and for some nucleic acid sequences, translation and expression of the nucleotide sequence (e.g. in an in vitro transcription/translation system or in a host cell when the vector is introduced into the host cell). Appropriate recombination and cloning methods are disclosed in US Pub. No. 2004/0171156, the contents of which are herein incorporated by reference in their entirety for all purposes.

Regulatory elements are operably linked to one or more elements of a targetable nuclease system so as to drive transcription, and for some nucleic acid sequences, translation and expression of the one or more components of the targetable nuclease system.

In addition, the polynucleotide sequence encoding the nucleic acid-guided nuclease can be codon optimized for expression in particular cells, such as prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammal including non-human primate. In addition or alternatively, a vector may include a regulatory element operably liked to a polynucleotide sequence, which, when transcribed, forms a guide RNA.

The nucleic acid assembly module can be configured to perform a wide variety of different nucleic acid assembly techniques in an automated fashion. Nucleic acid assembly techniques that can be performed in the nucleic acid assembly module of the disclosed automated multi-module cell editing instruments include, but are not limited to, those assembly methods that use restriction endonucleases, including PCR, BioBrick assembly (U.S. Pat. No. 9,361,427), Type IIS cloning (e.g., GoldenGate assembly, European Patent Application Publication EP 2 395 087 A1), and Ligase Cycling Reaction (de Kok, ACS Synth Biol., 3(2): 97-106 (2014); Engler, et al., PLoS One, 3(11):e3647 (2008); and U.S. Pat. No. 6,143,527). In other embodiments, the nucleic acid assembly techniques performed by the disclosed automated multi-module cell editing instruments are based on overlaps between adjacent parts of the nucleic acids, such as Gibson Assembly®, CPEC, SLIC, Ligase Cycling etc. Additional assembly methods include gap repair in yeast (Bessa, Yeast, 29(10):419-23 (2012)), gateway cloning (Ohtsuka, Curr Pharm Biotechnol, 10(2):244-51 (2009)); U.S. Pat. Nos. 5,888,732; and 6,277,608), and topoisomerase-mediated cloning (Udo, PLoS One, 10(9): e0139349 (2015); and U.S. Pat. No. 6,916,632). These and other nucleic acid assembly techniques are described, e.g., in Sands and Brent, Curr Protoc Mol Biol., 113:3.26.1-3.26.20 (2016).

The nucleic acid assembly module is temperature controlled depending upon the type of nucleic acid assembly used in the automated multi-module cell editing instrument. For example, when PCR is utilized in the nucleic acid assembly module, the module includes a thermocycling capability allowing the temperatures to cycle between denaturation, annealing and extension steps. When single temperature assembly methods (e.g., isothermal assembly methods) are utilized in the nucleic acid assembly module, the module provides the ability to reach and hold at the temperature that optimizes the specific assembly process being performed. These temperatures and the duration for maintaining these temperatures can be determined by a preprogrammed set of parameters executed by a script, or manually controlled by the user using the processing system of the automated multi-module cell editing instrument.

In one embodiment, the nucleic acid assembly module is a module to perform assembly using a single, isothermal reaction. Certain isothermal assembly methods can combine simultaneously up to 15 nucleic acid fragments based on sequence identity. The assembly method provides, in some embodiments, nucleic acids to be assembled which include an approximate 20-40 base overlap with adjacent nucleic acid fragments. The fragments are mixed with a cocktail of three enzymes—an exonuclease, a polymerase, and a ligase-along with buffer components. Because the process is isothermal and can be performed in a 1-step or 2-step method using a single reaction vessel, isothermal assembly reactions are ideal for use in an automated multi-module cell editing instrument. The 1-step method allows for the assembly of up to five different fragments using a single step isothermal process. The fragments and the master mix of enzymes are combined and incubated at 50° C. for up to one hour. For the creation of more complex constructs with up to fifteen fragments or for incorporating fragments from 100 bp up to 10 kb, typically the 2-step is used, where the 2-step reaction requires two separate additions of master mix; one for the exonuclease and annealing step and a second for the polymerase and ligation steps.

The Cell Transformation Module

FIGS. 5A and 5B depict the structure and components of an embodiment of an exemplary reagent cartridge useful in the automated multi-module instrument described therein. In FIG. 5A, reagent cartridge 500 comprises a body 502, which has reservoirs 504. One reservoir 504 is shown empty, and two of the reservoirs have individual tubes (not shown) inserted therein, with individual tube covers 505. Additionally shown are rows of reservoirs into which have been inserted co-joined rows of large tubes 503a, and co-joined rows of small tubes 503b. The co-joined rows of tubes are presented in a strip, with outer flanges 507 that mate on the backside of the outer flange (not shown) with an indentation 509 in the body 502, so as to secure the co-joined rows of tubes (503a and 503b) to the reagent cartridge 500. Shown also is a base 511 of reagent cartridge body 502. Note that the reservoirs 504 in body 502 are shaped generally like the tubes in the co-joined tubes that are inserted into these reservoirs 504.

FIG. 5B depicts the reagent cartridge 500 in FIG. 5A with a row of co-joined large tubes 503a, a row of co-joined small tubes 503b, and one large tube 560 with a cover 505 removed from (i.e., depicted above) the reservoirs 504 of the reagent cartridge 500. Again, the co-joined rows of tubes are presented in a strip, with individual large tubes 561 shown, and individual small tubes 555 shown. Again, each strip of co-joined tubes comprises outer flanges 507 that mate on the backside (not shown) of the outer flange with an indentation 509 in the body 502, to secure the co-joined rows of tubes (503a and 503b) to the reagent cartridge 500. As in FIG. 5A, reagent cartridge body 502 comprises a base 511. Reagent cartridge 500 may be made from any suitable material, including stainless steel, aluminum, or plastics including polyvinyl chloride, cyclic olefin copolymer (COC), polyethylene, polyamide, polypropylene, acrylonitrile butadiene, polycarbonate, polyetheretheketone (PEEK), poly(methyl methylacrylate) (PMMA), polysulfone, and polyurethane, and co-polymers of these and other polymers. Again, if reagent cartridge 500 is disposable, it preferably is made of plastic. In addition, in many embodiments the material used to fabricate the cartridge is thermally-conductive, as reagent cartridge 500 may contact a thermal device (not shown) that heats or cools reagents in the reagent reservoirs 504, including reagents in co-joined tubes. In some embodiments, the thermal device is a Peltier device or thermoelectric cooler.

Figure 5C:
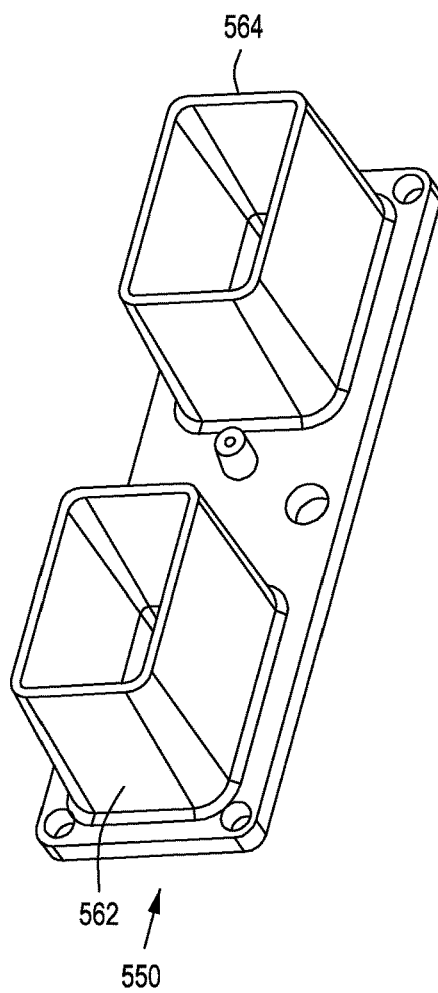
FIG. 5C is a top perspective view of one embodiment of an exemplary flow-through electroporation device that may be part of a reagent cartridge.
Figure 5D:
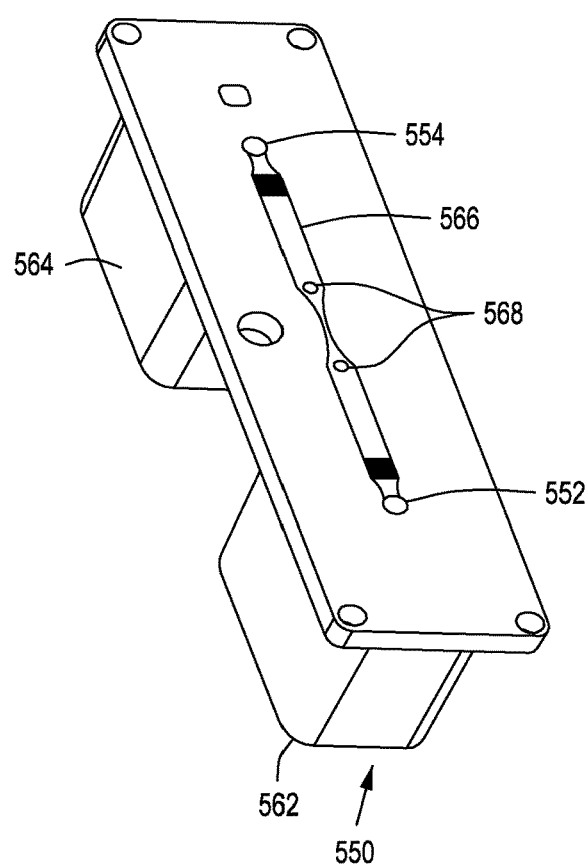
FIG. 5D depicts a bottom perspective view of one embodiment of an exemplary flow-through electroporation device that may be part of a reagent cartridge.

FIGS. 5C and 5D are top perspective and bottom perspective views, respectively, of an exemplary FTEP device 550 that may be part of (e.g., a component in) reagent cartridge 500 in FIGS. 5A and 5B or may be a stand-alone module; that is, not a part of a reagent cartridge or other module. FIG. 5C depicts an FTEP device 550. The FTEP device 550 has wells that define cell sample inlets 552 and cell sample outlets 554. FIG. 5D is a bottom perspective view of the FTEP device 550 of FIG. 5C. An inlet well 552 and an outlet well 554 can be seen in this view. Also seen in FIG. 5D are the bottom of an inlet 562 corresponding to well 552, the bottom of an outlet 564 corresponding to the outlet well 554, the bottom of a defined flow channel 566 and the bottom of two electrodes 568 on either side of flow channel 566. The FTEP devices may comprise push-pull pneumatic means to allow multi-pass electroporation procedures; that is, cells to electroporated may be "pulled" from the inlet toward the outlet for one pass of electroporation, then be "pushed" from the outlet end of the FTEP device toward the inlet end to pass between the electrodes again for another pass of electroporation. Further, this process may be repeated one to many times. For additional information regarding FTEP devices, see, e.g., U.S. Pat. Nos. 10,435, 713; 10,443,074; 10,323,258; and 10,508,288. Further, other embodiments of the reagent cartridge may provide or accommodate electroporation devices that are not configured as FTEP devices, such as those described in U.S. Ser. No. 16/109,156, filed 22 Aug. 2018. For reagent cartridges useful in the present automated multi-module cell processing instruments, see, e.g., U.S. Pat. Nos. 10,376,889; 10,406, 525; 10,576,474; and U.S. Ser. Nos. 16/749,757, filed 22 Jan. 2020; and 16/827,222, filed 23 Mar. 2020.

Figure 5E:
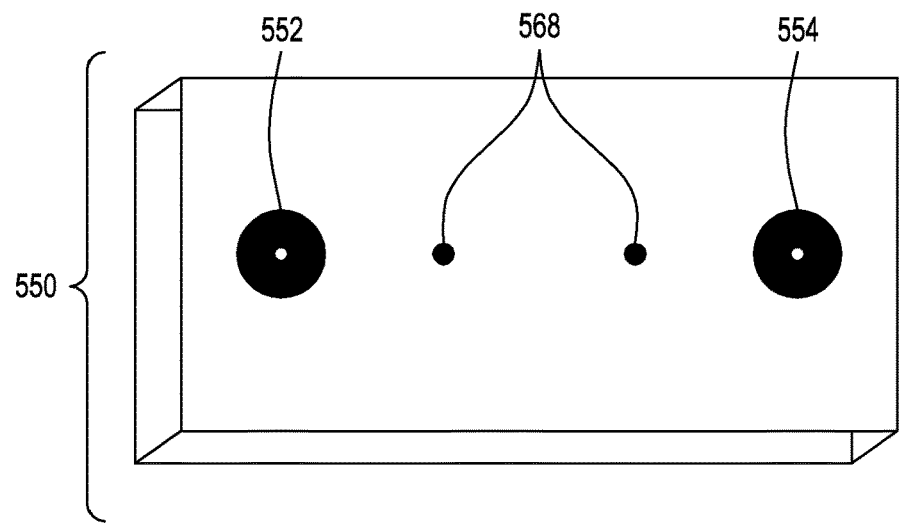
FIGS. 5E-5G depict a top perspective view, a top view of a cross section, and a side perspective view of a cross section of an FTEP device useful in a multi-module automated cell processing instrument such as that shown in FIGS. 2A-2C.
Figure 5F:
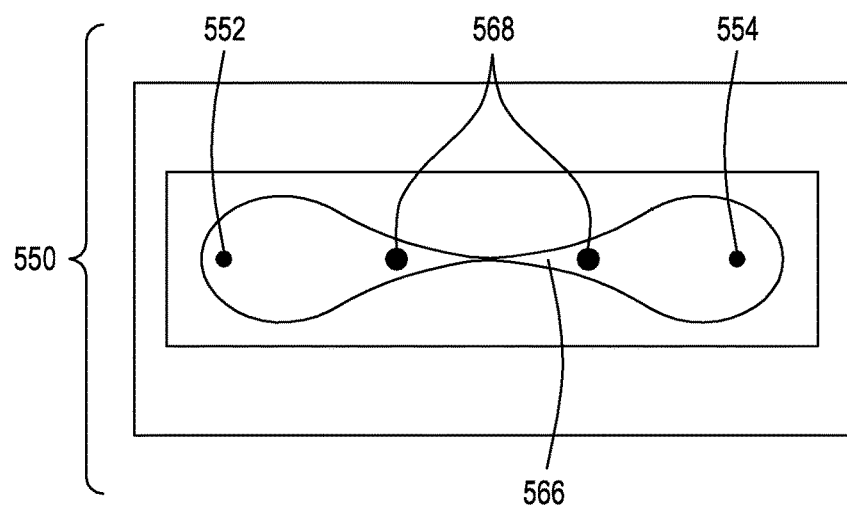
Figure 5G:
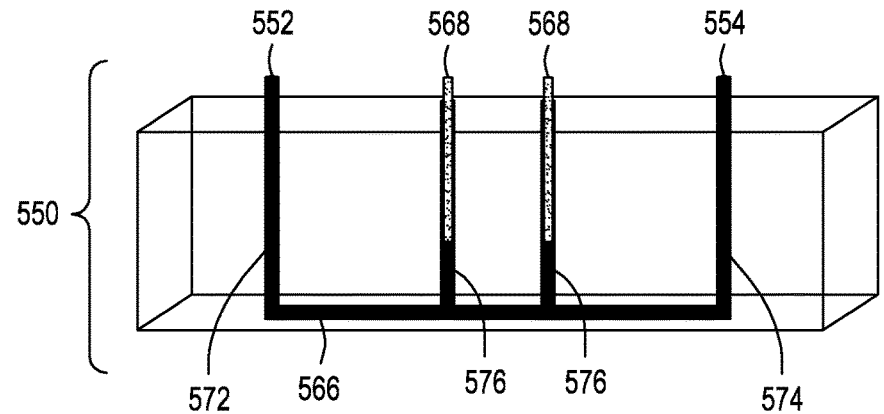

Additional details of the FTEP devices are illustrated in FIGS. 5E-5G. Note that in the FTEP devices in FIGS. 5E-5G the electrodes are placed such that a first electrode is placed between an inlet and a narrowed region of the flow channel, and the second electrode is placed between the narrowed region of the flow channel and an outlet. FIG. 5E shows a top planar view of an FTEP device 550 having an inlet 552 for introducing a fluid containing cells and exogenous material into FTEP device 550 and an outlet 554 for removing the transformed cells from the FTEP following electroporation. The electrodes 568 are introduced through channels (not shown) in the device.

FIG. 5F shows a cutaway view from the top of the FTEP device 550, with the inlet 552, outlet 554, and electrodes 568 positioned with respect to a flow channel 566. FIG. 5G shows a side cutaway view of FTEP device 550 with the inlet 552 and inlet channel 572, and outlet 554 and outlet channel 574. The electrodes 568 are positioned in electrode channels 576 so that they are in fluid communication with the flow channel 566, but not directly in the path of the cells traveling through the flow channel 566. Note that the first electrode is placed between the inlet and the narrowed region of the flow channel, and the second electrode is placed between the narrowed region of the flow channel and the outlet. The electrodes 568 in this aspect of the device are positioned in the electrode channels 576 which are generally perpendicular to the flow channel 566 such that the fluid containing the cells and exogenous material flows from the inlet channel 572 through the flow channel 566 to the outlet channel 574, and in the process fluid flows into the electrode channels 576 to be in contact with the electrodes 568. In this aspect, the inlet channel, outlet channel and electrode channels all originate from the same planar side of the device. In certain aspects, however, the electrodes may be introduced from a different planar side of the FTEP device than the inlet and outlet channels.

In the FTEP devices of the disclosure, the toxicity level of the transformation results in greater than 30% viable cells after electroporation, preferably greater than 35%, 40%, 45%, 50%, 55%, 60%, 70%, 75%, 80%, 85%, 90%, 95% or even 99% viable cells following transformation, depending on the cell type and the nucleic acids being introduced into the cells.

The housing of the FTEP device can be made from many materials depending on whether the FTEP device is to be reused, autoclaved, or is disposable, including stainless steel, silicon, glass, resin, polyvinyl chloride, polyethylene, polyamide, polystyrene, polyethylene, polypropylene, acrylonitrile butadiene, polycarbonate, polyetheretheketone (PEEK), polysulfone and polyurethane, co-polymers of these and other polymers. Similarly, the walls of the channels in the device can be made of any suitable material including silicone, resin, glass, glass fiber, polyvinyl chloride, polyethylene, polyamide, polyethylene, polypropylene, acrylonitrile butadiene, polycarbonate, polyetheretheketone (PEEK), polysulfone and polyurethane, co-polymers of these and other polymers. Preferred materials include crystal styrene, cyclo-olefin polymer (COP) and cyclic olephin co-polymers (COC), which allow the device to be formed entirely by injection molding in one piece with the exception of the electrodes and, e.g., a bottom sealing film if present.

The FTEP devices described herein (or portions of the FTEP devices) can be created or fabricated via various techniques, e.g., as entire devices or by creation of structural layers that are fused or otherwise coupled. For example, for metal FTEP devices, fabrication may include precision mechanical machining or laser machining; for silicon FTEP devices, fabrication may include dry or wet etching; for glass FTEP devices, fabrication may include dry or wet etching, powderblasting, sandblasting, or photostructuring; and for plastic FTEP devices fabrication may include thermoforming, injection molding, hot embossing, or laser machining.

The components of the FTEP devices may be manufactured separately and then assembled, or certain components of the FTEP devices (or even the entire FTEP device except for the electrodes) may be manufactured (e.g., using 3D printing) or molded (e.g., using injection molding) as a single entity, with other components added after molding. For example, housing and channels may be manufactured or molded as a single entity, with the electrodes later added to form the FTEP unit. Alternatively, the FTEP device may also be formed in two or more parallel layers, e.g., a layer with the horizontal channel and filter, a layer with the vertical channels, and a layer with the inlet and outlet ports, which are manufactured and/or molded individually and assembled following manufacture.

In specific aspects, the FTEP device can be manufactured using a circuit board as a base, with the electrodes, filter and/or the flow channel formed in the desired configuration on the circuit board, and the remaining housing of the device containing, e.g., the one or more inlet and outlet channels and/or the flow channel formed as a separate layer that is then sealed onto the circuit board. The sealing of the top of the housing onto the circuit board provides the desired configuration of the different elements of the FTEP devices of the disclosure. Also, two to many FTEP devices may be manufactured on a single substrate, then separated from one another thereafter or used in parallel. In certain embodiments, the FTEP devices are reusable and, in some embodiments, the FTEP devices are disposable. In additional embodiments, the FTEP devices may be autoclavable.

The electrodes 508 can be formed from any suitable metal, such as copper, stainless steel, titanium, aluminum, brass, silver, rhodium, gold or platinum, or graphite. One preferred electrode material is alloy 303 (UNS330300) austenitic stainless steel. An applied electric field can destroy electrodes made from of metals like aluminum. If a multiple-use (i.e., non-disposable) flow-through FTEP device is desired—as opposed to a disposable, one-use flow-through FTEP device—the electrode plates can be coated with metals resistant to electrochemical corrosion. Conductive coatings like noble metals, e.g., gold, can be used to protect the electrode plates.

As mentioned, the FTEP devices may comprise push-pull pneumatic means to allow multi-pass electroporation procedures; that is, cells to be electroporated may be "pulled" from the inlet toward the outlet for one pass of electroporation, then be "pushed" from the outlet end of the flow-through FTEP device toward the inlet end to pass between the electrodes again for another pass of electroporation. This process may be repeated one to many times.

Depending on the type of cells to be electroporated (e.g., bacterial, yeast, mammalian) and the configuration of the electrodes, the distance between the electrodes in the flow channel can vary widely. For example, where the flow channel decreases in width, the flow channel may narrow to between 10 μm and 5 mm, or between 25 μm and 3 mm, or between 50 μm and 2 mm, or between 75 μm and 1 mm. The distance between the electrodes in the flow channel may be between 1 mm and 10 mm, or between 2 mm and 8 mm, or between 3 mm and 7 mm, or between 4 mm and 6 mm. The overall size of the FTEP device may be from 3 cm to 15 cm in length, or 4 cm to 12 cm in length, or 4.5 cm to 10 cm in length. The overall width of the FTEP device may be from 0.5 cm to 5 cm, or from 0.75 cm to 3 cm, or from 1 cm to 2.5 cm, or from 1 cm to 1.5 cm.

The region of the flow channel that is narrowed is wide enough so that at least two cells can fit in the narrowed portion side-by-side. For example, a typical bacterial cell is 1 μm in diameter; thus, the narrowed portion of the flow channel of the FTEP device used to transform such bacterial cells will be at least 2 μm wide. In another example, if a mammalian cell is approximately 50 μm in diameter, the narrowed portion of the flow channel of the FTEP device used to transform such mammalian cells will be at least 100 μm wide. That is, the narrowed portion of the FTEP device will not physically contort or "squeeze" the cells being transformed.

In embodiments of the FTEP device where reservoirs are used to introduce cells and exogenous material into the FTEP device, the reservoirs range in volume from 100 μL to 10 mL, or from 500 μL to 75 mL, or from 1 mL to 5 mL. The flow rate in the FTEP ranges from 0.1 mL to 5 mL per minute, or from 0.5 mL to 3 mL per minute, or from 1.0 mL to 2.5 mL per minute. The pressure in the FTEP device ranges from 1-30 psi, or from 2-10 psi, or from 3-5 psi.

To avoid different field intensities between the electrodes, the electrodes should be arranged in parallel. Furthermore, the surface of the electrodes should be as smooth as possible without pin holes or peaks. Electrodes having a roughness Rz of 1 to 10 μm are preferred. In another embodiment of the invention, the flow-through electroporation device comprises at least one additional electrode which applies a ground potential to the FTEP device. Flow-through electroporation devices (either as a stand-alone instrument or as a module in an automated multi-module system) are described in, e.g., U.S. Pat. Nos. 10,435,713; 10,443,074; 10,323,258; and 10,508,288.

Cell Singulation and Enrichment Device

FIG. 6A depicts a solid wall device 6050 and a workflow for singulating cells in microwells in the solid wall device. At the top left of the figure (i), there is depicted solid wall device 6050 with microwells 6052. A section 6054 of substrate 6050 is shown at (ii), also depicting microwells 6052. At (iii), a side cross-section of solid wall device 6050 is shown, and microwells 6052 have been loaded, where, in this embodiment, Poisson or substantial Poisson loading has taken place; that is, each microwell has few, one or no cells. At (iv), workflow 6040 is illustrated where substrate 6050 having microwells 6052 shows microwells 6056 with one cell per microwell, microwells 6057 with no cells in the microwells, and one microwell 6060 with two cells in the microwell. In step 6051, the cells in the microwells are allowed to double approximately 2-150 times to form clonal colonies (v), then editing is allowed to occur 6053.

After editing 6053, many cells in the colonies of cells that have been edited die as a result of the double-strand cuts caused by active editing and there is a lag in growth for the edited cells that do survive but must repair and recover following editing (microwells 6058), where cells that do not undergo editing thrive (microwells 6059) (vi). All cells are allowed to continue grow to establish colonies and normalize 6055, where the colonies of edited cells in microwells 6058 catch up in size and/or cell number with the cells in microwells 6059 that do not undergo editing (vii). Once the cell colonies are normalized, either pooling 6062 of all cells in the microwells can take place, in which case the cells are enriched for edited cells by eliminating the bias from non-editing cells and fitness effects from editing; alternatively, colony growth in the microwells is monitored after editing, and slow growing colonies (e.g., the cells in microwells 6058) are identified and selected 6061 (e.g., "cherry picked") resulting in even greater enrichment of edited cells.

In growing the cells, the medium used will depend, of course, on the type of cells being edited—e.g., bacterial, yeast or mammalian. For example, medium for yeast cell growth includes LB, SOC, TPD, YPG, YPAD, MEM and DMEM.

Figure 6B:
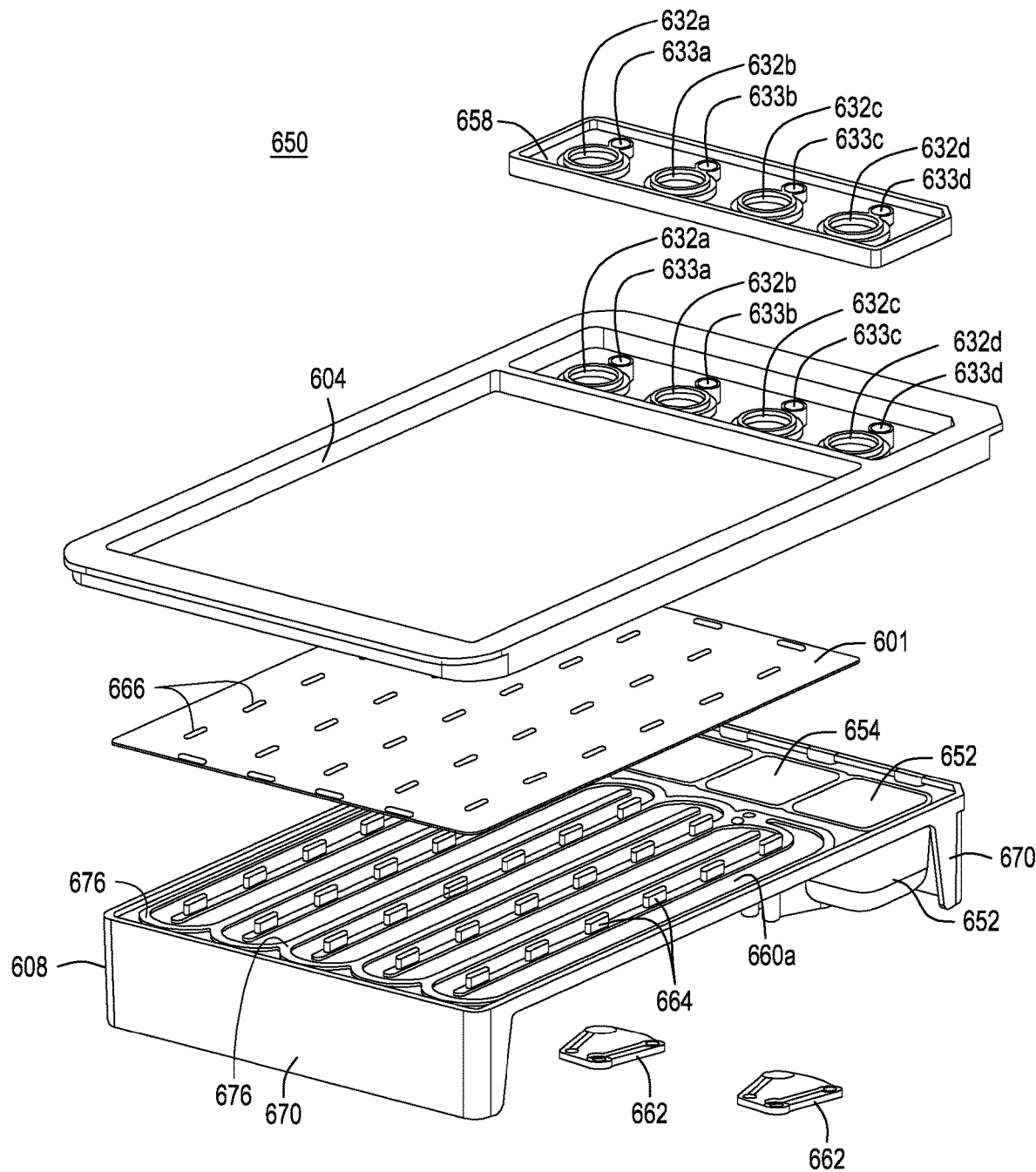

A module useful for performing the methods depicted in FIG. 6A is a solid wall isolation, incubation, and normalization (SWIIN) module. FIG. 6B depicts an embodiment of a SWIIN module 650 from an exploded top perspective view. In SWIIN module 650 the retentate member is formed on the bottom of a top of a SWIIN module component and the permeate member is formed on the top of the bottom of a SWIIN module component.

The SWIIN module 650 in FIG. 6B comprises from the top down, a reservoir gasket or cover 658, a retentate member 604 (where a retentate flow channel cannot be seen in this FIG. 6B), a perforated member 601 swaged with a filter (filter not seen in FIG. 6B), a permeate member 608 comprising integrated reservoirs (permeate reservoirs 652 and retentate reservoirs 654), and two reservoir seals 662, which seal the bottom of permeate reservoirs 652 and retentate reservoirs 654. A permeate channel 660a can be seen disposed on the top of permeate member 608, defined by a raised portion 676 of serpentine channel 660a, and ultrasonic tabs 664 can be seen disposed on the top of permeate member 608 as well. The perforations that form the wells on perforated member 601 are not seen in this FIG. 6B; however, through-holes 666 to accommodate the ultrasonic tabs 664 are seen. In addition, supports 670 are disposed at either end of SWIIN module 650 to support SWIIN module 650 and to elevate permeate member 608 and retentate member 604 above reservoirs 652 and 654 to minimize bubbles or air entering the fluid path from the permeate reservoir to serpentine channel 660a or the fluid path from the retentate reservoir to serpentine channel 660b (neither fluid path is seen in this FIG. 6B). Also seen is a gasket 658, which covers the permeate and retentate reservoir access apertures 632a, 632b, 632c, and 632d, as well as pneumatic ports 633a, 633b, 633c and 633d.

In this FIG. 6B, it can be seen that the serpentine channel 660a that is disposed on the top of permeate member 608 traverses permeate member 608 for most of the length of permeate member 608 except for the portion of permeate member 608 that comprises permeate reservoirs 652 and retentate reservoirs 654 and for most of the width of permeate member 608. As used herein with respect to the distribution channels in the retentate member or permeate member, "most of the length" means about 95% of the length of the retentate member or permeate member, or about 90%, 85%, 80%, 75%, or 70% of the length of the retentate member or permeate member. As used herein with respect to the distribution channels in the retentate member or permeate member, "most of the width" means about 95% of the width of the retentate member or permeate member, or about 90%, 85%, 80%, 75%, or 70% of the width of the retentate member or permeate member.

In this embodiment of a SWIIN module, the perforated member includes through-holes to accommodate ultrasonic tabs disposed on the permeate member. Thus, in this embodiment the perforated member is fabricated from 316 stainless steel, and the perforations form the walls of microwells while a filter or membrane is used to form the bottom of the microwells. Typically, the perforations (microwells) are approximately 150 µm-200 µm in diameter, and the perforated member is approximately 125 µm deep, resulting in microwells having a volume of approximately 2.5 nl, with a total of approximately 200,000 microwells. The distance between the microwells is approximately 279 µm center-to-center. Though here the microwells have a volume of approximately 2.5 nl, the volume of the microwells may be from 1 to 25 nl, or preferably from 2 to 10 nl, and even more preferably from 2 to 4 nl. As for the filter or membrane, like the filter described previously, filters appropriate for use are solvent resistant, contamination free during filtration, and are able to retain the types and sizes of cells of interest. For example, in order to retain small cell types such as bacterial cells, pore sizes can be as low as 0.10 µm, however for other cell types (e.g., such as for mammalian cells), the pore sizes can be as high as 10.0 µm-20.0 µm or more. Indeed, the pore sizes useful in the cell concentration device/module include filters with sizes from 0.10 µm, 0.11 µm, 0.12 µm, 0.13 µm, 0.14 µm, 0.15 µm, 0.16 µm, 0.17 µm, 0.18 µm, 0.19 µm, 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters may be fabricated from any suitable material including cellulose mixed ester (cellulose nitrate and acetate) (CME), polycarbonate (PC), polyvinylidene fluoride (PVDF), polyethersulfone (PES), polytetrafluoroethylene (PTFE), nylon, or glass fiber.

The cross-section configuration of the mated serpentine channel may be round, elliptical, oval, square, rectangular, trapezoidal, or irregular. If square, rectangular, or another shape with generally straight sides, the cross section may be from about 2 mm to 15 mm wide, or from 3 mm to 12 mm wide, or from 5 mm to 10 mm wide. If the cross section of the mated serpentine channel is generally round, oval or elliptical, the radius of the channel may be from about 3 mm to 20 mm in hydraulic radius, or from 5 mm to 15 mm in hydraulic radius, or from 8 mm to 12 mm in hydraulic radius.

Serpentine channels 660a and 660b can have approximately the same volume or a different volume. For example, each "side" or portion 660a, 660b of the serpentine channel may have a volume of, e.g., 2 mL, or serpentine channel 660a of permeate member 608 may have a volume of 2 mL, and the serpentine channel 660b of retentate member 604 may have a volume of, e.g., 3 mL. The volume of fluid in the serpentine channel may range from about 2 mL to about 80 mL, or about 4 mL to 60 mL, or from 5 mL to 40 mL, or from 6 mL to 20 mL (note these volumes apply to a SWIIN module comprising a, e.g., 50-500K perforation member). The volume of the reservoirs may range from 5 mL to 50 mL, or from 7 mL to 40 mL, or from 8 mL to 30 mL or from 10 mL to 20 mL, and the volumes of all reservoirs may be the same or the volumes of the reservoirs may differ (e.g., the volume of the permeate reservoirs is greater than that of the retentate reservoirs).

The serpentine channel portions 660a and 660b of the permeate member 608 and retentate member 604, respectively, are approximately 200 mm long, 130 mm wide, and 4 mm thick, though in other embodiments, the retentate and permeate members can be from 75 mm to 400 mm in length, or from 100 mm to 300 mm in length, or from 150 mm to 250 mm in length; from 50 mm to 250 mm in width, or from 75 mm to 200 mm in width, or from 100 mm to 150 mm in width; and from 2 mm to 15 mm in thickness, or from 4 mm to 10 mm in thickness, or from 5 mm to 8 mm in thickness. Embodiments the retentate (and permeate) members may be fabricated from PMMA (poly(methyl methacrylate) or other materials may be used, including polycarbonate, cyclic olefin co-polymer (COC), glass, polyvinyl chloride, polyethylene, polyamide, polypropylene, polysulfone, polyurethane, and co-polymers of these and other polymers. Preferably at least the retentate member is fabricated from a transparent material so that the cells can be visualized (see, e.g., FIG. 6E and the description thereof). For example, a video camera may be used to monitor cell growth by, e.g., density change measurements based on an image of an empty well, with phase contrast, or if, e.g., a chromogenic marker, such as a chromogenic protein, is used to add a distinguishable color to the cells. Chromogenic markers such as blitzen blue, dreidel teal, virginia violet, vixen purple, prancer purple, tinsel purple, maccabee purple, donner magenta, cupid pink, seraphina pink, scrooge orange, and leor orange (the Chromogenic Protein Paintbox, all available from ATUM (Newark, Calif.)) obviate the need to use fluorescence, although fluorescent cell markers, fluorescent proteins, and chemiluminescent cell markers may also be used.

Because the retentate member preferably is transparent, colony growth in the SWIIN module can be monitored by automated devices such as those sold by JoVE (ScanLag™ system, Cambridge, Mass.) (also see Levin-Reisman, et al., Nature Methods, 7:737-39 (2010)). Automated colony pickers may be employed, such as those sold by, e.g., TECAN (Pickolo™ system, Mannedorf, Switzerland); Hudson Inc. (RapidPick™ Springfield, N.J.); Molecular Devices (QPix 400™ system, San Jose, Calif.); and Singer Instruments (PIXL™ system, Somerset, UK).

Due to the heating and cooling of the SWIIN module, condensation may accumulate on the retentate member which may interfere with accurate visualization of the growing cell colonies. Condensation of the SWIIN module 650 may be controlled by, e.g., moving heated air over the top of (e.g., retentate member) of the SWIIN module 650, or by applying a transparent heated lid over at least the serpentine channel portion 660*b* of the retentate member 604. See, e.g., FIG. 6E and the description thereof infra.

In SWIIN module 650 cells and medium—at a dilution appropriate for Poisson or substantial Poisson distribution of the cells in the microwells of the perforated member—are flowed into serpentine channel 660*b* from ports in retentate member 604, and the cells settle in the microwells while the medium passes through the filter into serpentine channel 660*a* in permeate member 608. The cells are retained in the microwells of perforated member 601 as the cells cannot travel through filter 603. Appropriate medium may be introduced into permeate member 608 through permeate ports 611. The medium flows upward through filter 603 to nourish the cells in the microwells (perforations) of perforated member 601. Additionally, buffer exchange can be effected by cycling medium through the retentate and permeate members. In operation, the cells are deposited into the microwells, are grown for an initial, e.g., 2-100 doublings, editing may be induced by, e.g., raising the temperature of the SWIIN to 42° C. to induce a temperature-inducible promoter or by removing growth medium from the permeate member and replacing the growth medium with a medium comprising a chemical component that induces an inducible promoter.

Once editing has taken place, the temperature of the SWIIN may be decreased, or the inducing medium may be removed and replaced with fresh medium lacking the chemical component thereby de-activating the inducible promoter. The cells then continue to grow in the SWIIN module 650 until the growth of the cell colonies in the microwells is normalized. For the normalization protocol, once the colonies are normalized, the colonies are flushed from the microwells by applying fluid or air pressure (or both) to the permeate member serpentine channel 660*a* and thus to filter 603 and pooled. Alternatively, if cherry picking is desired, the growth of the cell colonies in the microwells is monitored, and slow-growing colonies are directly selected; or, fast-growing colonies are eliminated.

FIG. 6C is a top perspective view of a SWIIN module with the retentate and perforated members in partial cross section. In this FIG. 6C, it can be seen that serpentine channel 660*a* is disposed on the top of permeate member 608 is defined by raised portions 676 and traverses permeate member 608 for most of the length and width of permeate member 608 except for the portion of permeate member 608 that comprises the permeate and retentate reservoirs (note only one retentate reservoir 652 can be seen). Moving from left to right, reservoir gasket 658 is disposed upon the integrated reservoir cover 678 (cover not seen in this FIG. 6C) of retentate member 604. Gasket 658 comprises reservoir access apertures 632*a*, 632*b*, 632*c*, and 632*d*, as well as pneumatic ports 633*a*, 633*b*, 633*c* and 633*d*. Also at the far left end is support 670. Disposed under permeate reservoir 652 can be seen one of two reservoir seals 662. In addition to the retentate member being in cross section, the perforated member 601 and filter 603 (filter 603 is not seen in this FIG. 6C) are in cross section. Note that there are a number of ultrasonic tabs 664 disposed at the right end of SWIIN module 650 and on raised portion 676 which defines the channel turns of serpentine channel 660*a*, including ultrasonic tabs 664 extending through through-holes 666 (not seen in this FIG. 6C but see FIG. 6B) of perforated member 601. There is also a support 670 at the end distal reservoirs 652, 654 of permeate member 608.

Figure 6D:
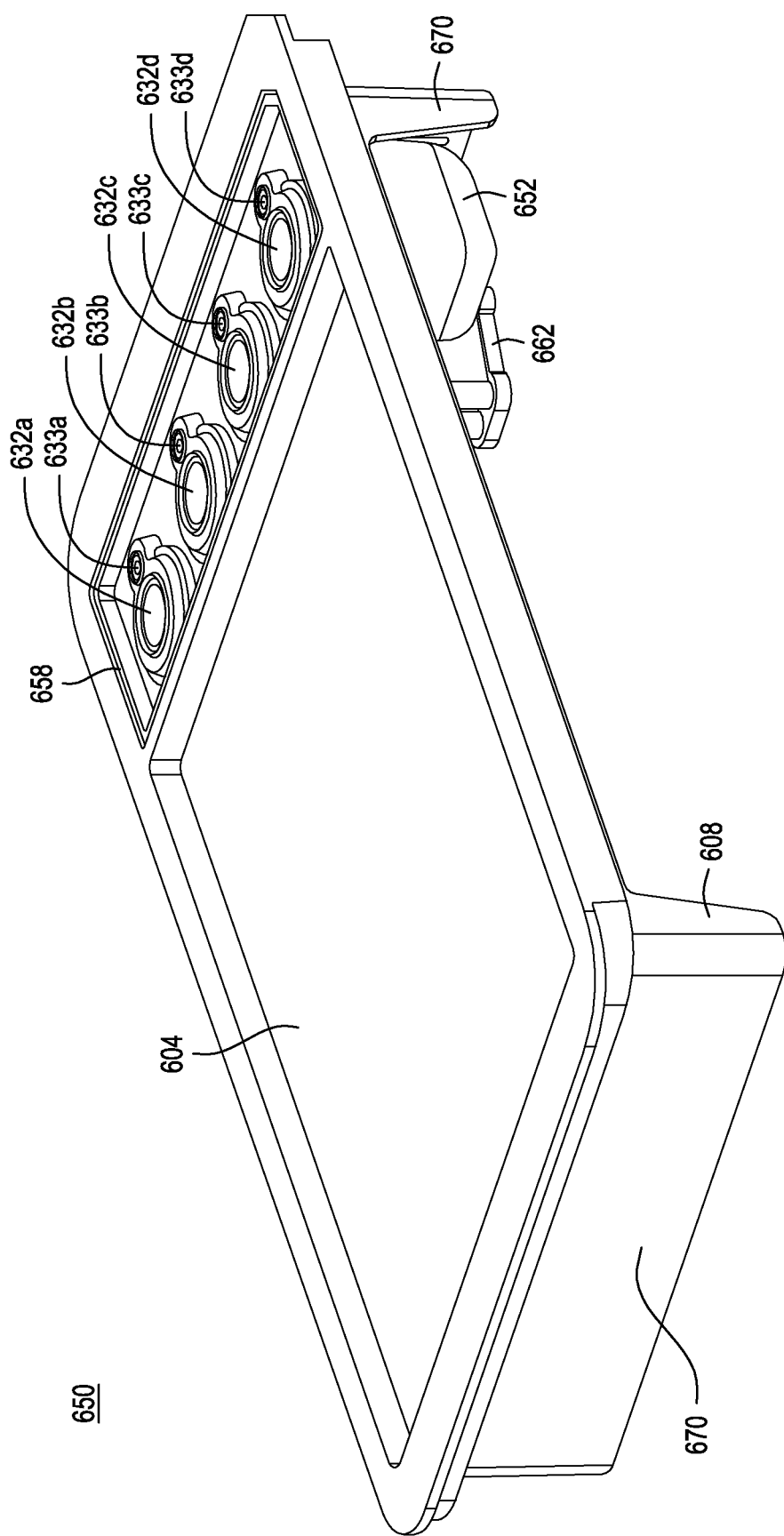

FIG. 6D is a side perspective view of an assembled SWIIN module 650, including, from right to left, reservoir gasket 658 disposed upon integrated reservoir cover 678 (not seen) of retentate member 604. Gasket 658 may be fabricated from rubber, silicone, nitrile rubber, polytetrafluoroethylene, a plastic polymer such as polychlorotrifluoroethylene, or other flexible, compressible material. Gasket 658 comprises reservoir access apertures 632*a*, 632*b*, 632*c*, and 632*d*, as well as pneumatic ports 633*a*, 633*b*, 633*c* and 633*d*. Also at the far-left end is support 670 of permeate member 608. In addition, permeate reservoir 652 can be seen, as well as one reservoir seal 662. At the far-right end is a second support 670.

Imaging of cell colonies growing in the wells of the SWIIN is desired in most implementations for, e.g., monitoring both cell growth and device performance and imaging is necessary for cherry-picking implementations. Real-time monitoring of cell growth in the SWIIN requires backlighting, retentate plate (top plate) condensation management and a system-level approach to temperature control, air flow, and thermal management. In some implementations, imaging employs a camera or CCD device with sufficient resolution to be able to image individual wells. For example, in some configurations a camera with a 9-pixel pitch is used (that is, there are 9 pixels center-to-center for each well). Processing the images may, in some implementations, utilize reading the images in grayscale, rating each pixel from low to high, where wells with no cells will be brightest (due to full or nearly-full light transmission from the backlight) and wells with cells will be dim (due to cells blocking light transmission from the backlight). After processing the images, thresholding is performed to determine which pixels will be called "bright" or "dim", spot finding is performed to find bright pixels and arrange them into blocks, and then the spots are arranged on a hexagonal grid of pixels that correspond to the spots. Once arranged, the measure of intensity of each well is extracted, by, e.g., looking at one or more pixels in the middle of the spot, looking at several to many pixels at random or pre-set positions, or averaging X number of pixels in the spot. In addition, background intensity may be subtracted. Thresholding is again used to call each well positive (e.g., containing cells) or negative (e.g., no cells in the well). The imaging information may be used in several ways, including taking images at time points for monitoring cell growth. Monitoring cell growth can be used to, e.g., remove the "muffin tops" of fast-growing cells followed by removal of all cells or removal of cells in "rounds" as described above, or recover cells from specific wells (e.g., slow-growing cell colonies); alternatively, wells containing fast-growing cells can be identified and areas of UV light covering the fast-growing cell colonies can be projected (or rastered with shutters) onto the SWIIN to irradiate or inhibit growth of those cells. Imaging may also be used to assure proper fluid flow in the serpentine channel 660.

Figure 6E:
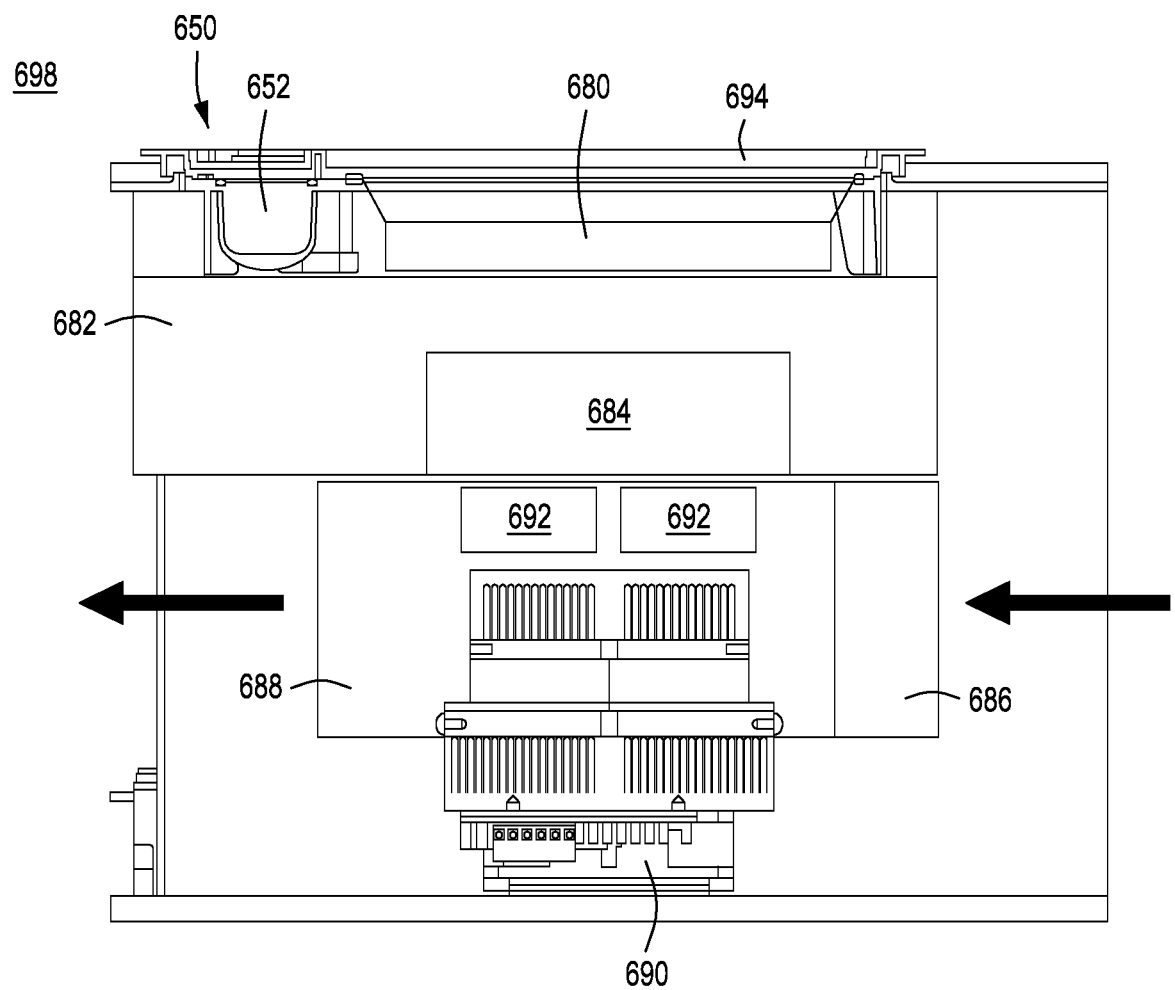
FIG. 6E depicts the embodiment of the SWIIN module in FIGS. 6B-6D further comprising a heater and a heated cover.

FIG. 6E depicts the embodiment of the SWIIN module in FIGS. 6B-6D further comprising a heat management system including a heater and a heated cover. The heated cover facilitates the condensation management that is required for imaging. Assembly 698 comprises a SWIIN module 650 seen lengthwise in cross section, where one permeate reservoir 652 is seen. Disposed immediately upon SWIIN module 650 is cover 694 and disposed immediately below SWIIN module 650 is backlight 680, which allows for imaging. Beneath and adjacent to the backlight and SWIIN module is insulation 682, which is disposed over a heatsink 684. In this FIG. 6E, the fins of the heatsink would be in-out of the page. In addition there is also axial fan 686 and heat sink 688, as well as two thermoelectric coolers 692, and a controller 690 to control the pneumatics, thermoelectric coolers, fan, solenoid valves, etc. The arrows denote cool air coming into the unit and hot air being removed from the unit. It should be noted that control of heating allows for growth of many different types of cells as well as strains of cells that are, e.g., temperature sensitive, etc., and allows use of temperature-sensitive promoters. Temperature control allows for protocols to be adjusted to account for differences in transformation efficiency, cell growth and viability. For more details regarding solid wall isolation incubation and normalization devices see U.S. Pat. Nos. 10,533,152; 10,550,363; 10,532,324; 10,625,212; 10,633,626; and 10,633,627; and U.S. Ser. Nos. 16/693,630, filed 25 November 2019; 16/823,269, filed 18 March 2020; 16/820,292, filed 16 Mar. 2020; 16/820,324, filed 16 Mar. 2020; and 16/686,066, filed 15 Nov. 2019.

Use of the Automated Multi-Module Yeast Cell Processing Instrument

Figure 7:
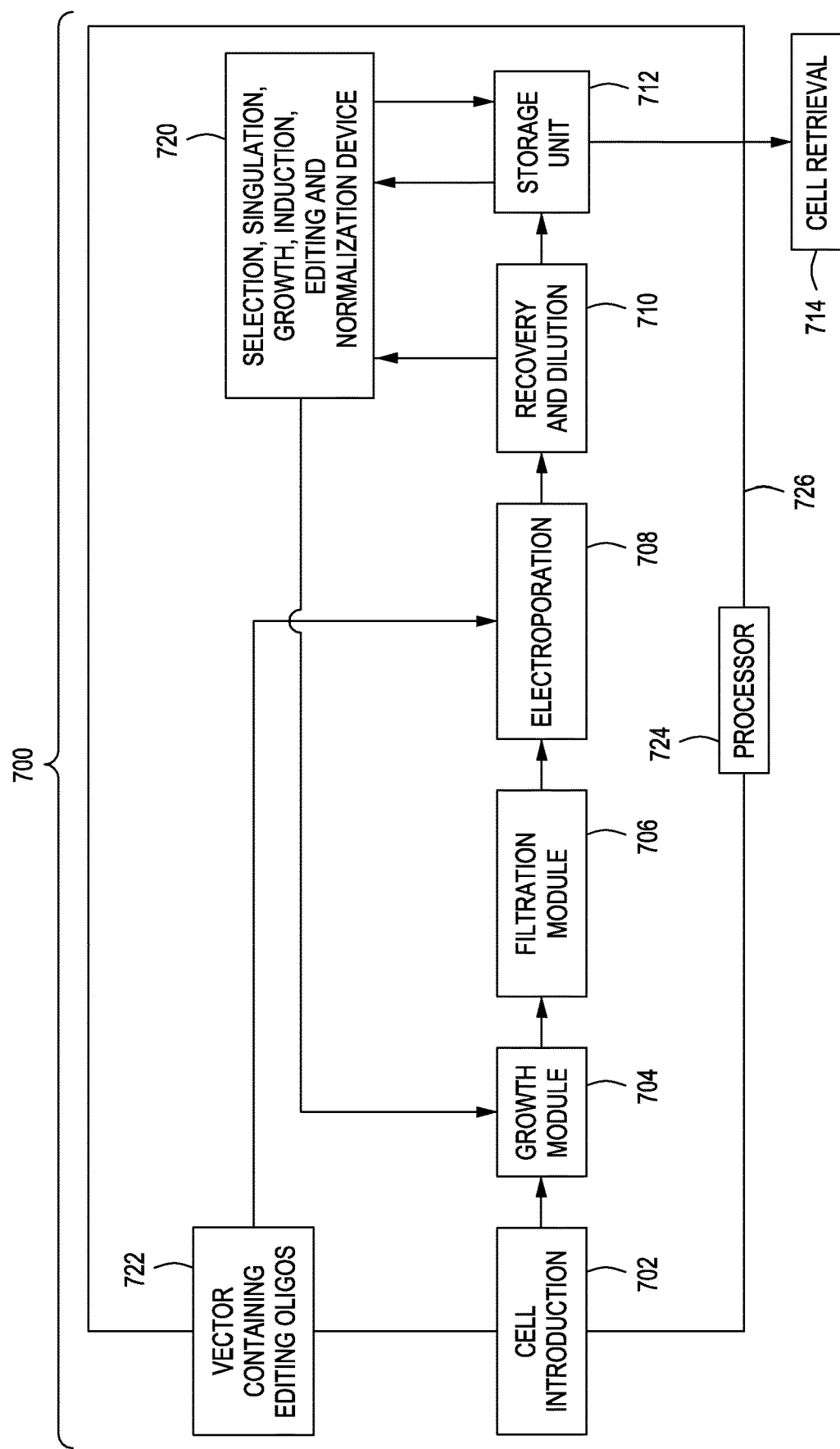
FIG. 7 is a simplified block diagram of an embodiment of an exemplary automated multi-module cell processing instrument comprising a solid wall singulation/growth/editing/normalization module for recursive cell editing.

FIG. 7 illustrates an embodiment of a multi-module cell processing instrument. This embodiment depicts an exemplary system that performs recursive gene editing on a cell population. The cell processing instrument 700 may include a housing 726, a reservoir for storing cells to be transformed or transfected 702, and a cell growth module (comprising, e.g., a rotating growth vial) 704. The cells to be transformed are transferred from a reservoir to the cell growth module to be cultured until the cells hit a target OD. Once the cells hit the target OD, the growth module may cool or freeze the cells for later processing or transfer the cells to a cell concentration module 706 where the cells are subjected to buffer exchange and rendered electrocompetent, and the volume of the cells may be reduced substantially. Once the cells have been concentrated to an appropriate volume, the cells are transferred to electroporation device 708. In addition to the reservoir for storing cells 702, the multi-module cell processing instrument includes a reservoir for storing the vector pre-assembled with editing oligonucleotide cassettes 722. The pre-assembled nucleic acid vectors are transferred to the electroporation device 708, which already contains the cell culture grown to a target OD. In the electroporation device 708, the nucleic acids are electroporated into the cells. Following electroporation, the cells are transferred into an optional recovery module 710, where the cells recover briefly post-transformation.

After recovery, the cells may be transferred to a storage module 712, where the cells can be stored at, e.g., 4° C. for later processing 714, or the cells may be diluted and transferred to a selection/singulation/growth/induction/editing/normalization (SWIIN) module 720. In the SWIIN 720, the cells are arrayed such that there is an average of one cell per microwell. The arrayed cells may be in selection medium to select for cells that have been transformed or transfected with the editing vector(s). Once singulated, the cells grow through 2-50 doublings and establish colonies. Once colonies are established, editing is induced by providing conditions (e.g., temperature, addition of an inducing or repressing chemical) to induce editing. Once editing is initiated and allowed to proceed, the cells are allowed to grow to terminal size (e.g., normalization of the colonies) in the microwells and then the cells are treated to conditions that cure the editing vector from this round. Once cured, the cells can be flushed out of the microwells and pooled, then transferred to the storage (or recovery) unit 712 or can be transferred back to the growth module 704 for another round of editing. In between pooling and transfer to a growth module, there typically is one or more additional steps, such as cell recovery, medium exchange (rendering the cells electrocompetent), cell concentration (typically concurrently with medium exchange by, e.g., filtration. Note that the selection/singulation/growth/induction/editing/normalization and editing modules may be the same module, where all processes are performed in, e.g., a solid wall device, or selection and/or dilution may take place in a separate vessel before the cells are transferred to the solid wall singulation/growth/induction/editing/normalization/editing module (solid wall device). Similarly, the cells may be pooled after normalization, transferred to a separate vessel, and cured in the separate vessel. As an alternative to singulation in, e.g., a solid wall device, the transformed cells may be grown in—and editing can be induced in—bulk liquid as described above in relation to FIGS. 1G and 1H above. Once the putatively-edited cells are pooled, they may be subjected to another round of editing, beginning with growth, cell concentration and treatment to render electrocompetent, and transformation by yet another donor nucleic acid in another editing cassette via the electroporation module 708.

In electroporation device 708, the cells selected from the first round of editing are transformed by a second set of editing oligos (or other type of oligos) and the cycle is repeated until the cells have been transformed and edited by a desired number of, e.g., editing cassettes. The multi-module cell processing instrument exemplified in FIG. 7 is controlled by a processor 724 configured to operate the instrument based on user input or is controlled by one or more scripts including at least one script associated with the reagent cartridge. The processor 724 may control the timing, duration, and temperature of various processes, the dispensing of reagents, and other operations of the various modules of the instrument 700. For example, a script or the processor may control the dispensing of cells, reagents, vectors, and editing oligonucleotides; which editing oligonucleotides are used for cell editing and in what order; the time, temperature and other conditions used in the recovery and expression module, the wavelength at which OD is read in the cell growth module, the target OD to which the cells are grown, and the target time at which the cells will reach the target OD. In addition, the processor may be programmed to notify a user (e.g., via an application) as to the progress of the cells in the automated multi-module cell processing instrument.

It should be apparent to one of ordinary skill in the art given the present disclosure that the process described may be recursive and multiplexed; that is, cells may go through the workflow described in relation to FIG. 7, then the resulting edited culture may go through another (or several or many) rounds of additional editing (e.g., recursive editing) with different editing vectors. For example, the cells from round 1 of editing may be diluted and an aliquot of the edited cells edited by editing vector A may be combined with editing vector B, an aliquot of the edited cells edited by editing vector A may be combined with editing vector C, an aliquot of the edited cells edited by editing vector A may be combined with editing vector D, and so on for a second round of editing. After round two, an aliquot of each of the double-edited cells may be subjected to a third round of editing, where, e.g., aliquots of each of the AB-, AC-, AD-edited cells are combined with additional editing vectors, such as editing vectors X, Y, and Z. That is that double-edited cells AB may be combined with and edited by vectors X, Y, and Z to produce triple-edited edited cells ABX, ABY, and ABZ; double-edited cells AC may be combined with and edited by vectors X, Y, and Z to produce triple-edited cells ACX, ACY, and ACZ; and double-edited cells AD may be combined with and edited by vectors X, Y, and Z to produce triple-edited cells ADX, ADY, and ADZ, and so on. In this process, many permutations and combinations of edits can be executed, leading to very diverse cell populations and cell libraries.

In any recursive process, it is advantageous to "cure" the previous engine and editing vectors (or single engine +editing vector in a single vector system). "Curing" is the process in which one or more vectors used in the prior round of editing is eliminated from the transformed cells as described in detail above in relation to FIGS. 1A-1I. Curing can be accomplished by, e.g., cleaving the vector(s) using a curing plasmid thereby rendering the editing and/or engine vector (or single, combined vector) nonfunctional; diluting the vector(s) in the cell population via cell growth (that is, the more growth cycles the cells go through, the fewer daughter cells will retain the editing or engine vector(s)), or by, e.g., utilizing a heat-sensitive origin of replication on the editing or engine vector (or combined engine +editing vector). The conditions for curing will depend on the mechanism used for curing; that is, in this example, how the curing plasmid cleaves the editing and/or engine vector.

Figure 8:
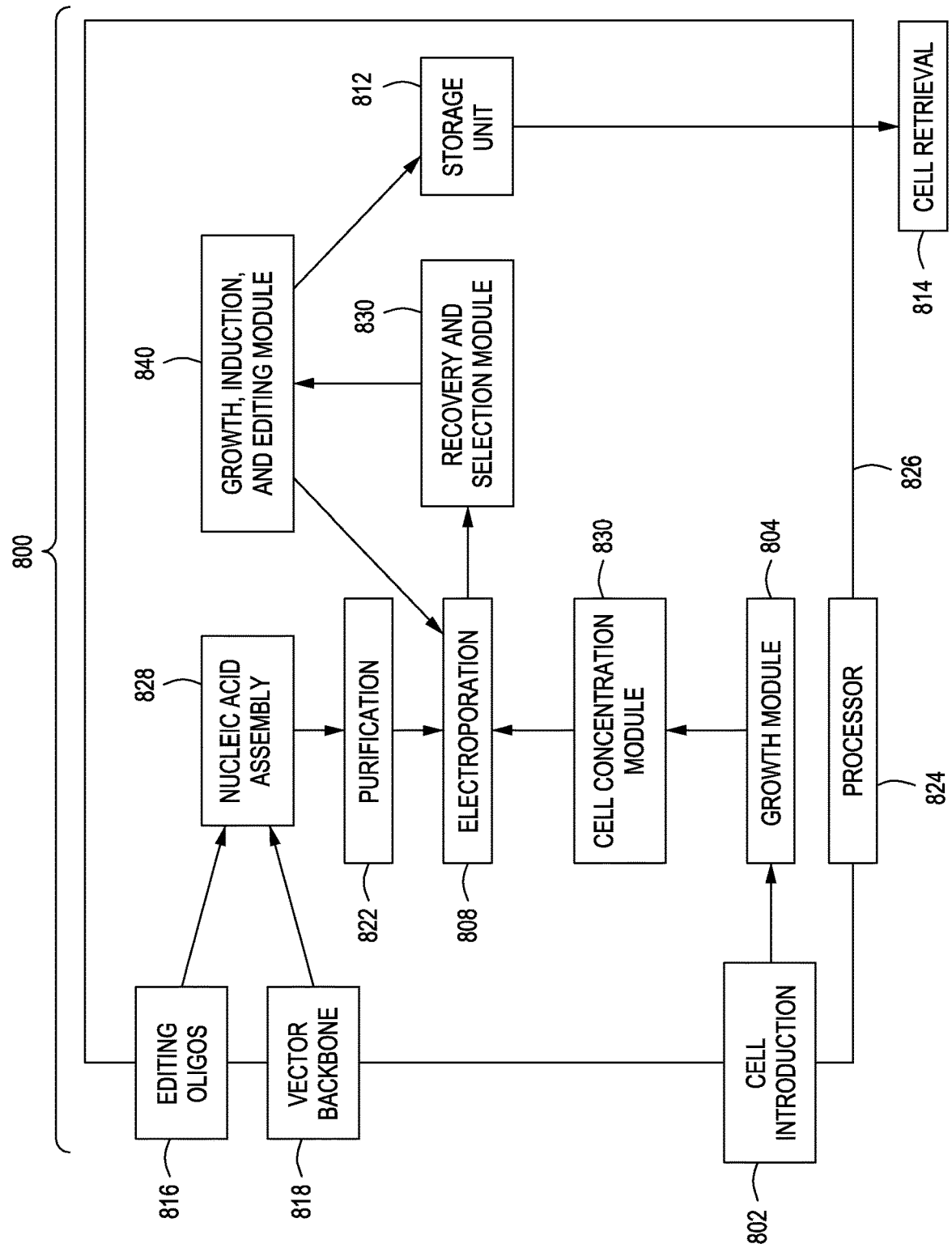
FIG. 8 is a simplified process diagram of an alternative embodiment of an exemplary automated multi-module cell processing instrument useful for recursive cell editing.

FIG. 8 is a simplified block diagram of an embodiment of an exemplary automated multi-module cell processing instrument comprising a bulk liquid growth module for induced editing and enrichment for edited cells as described above in relation to FIGS. 1G and 1H. The cell processing instrument 800 may include a housing 826, a reservoir of cells to be transformed or transfected 802, and a growth module (a cell growth device) 804. The cells to be transformed are transferred from a reservoir to the growth module to be cultured until the cells hit a target OD. Once the cells hit the target OD, the growth module may cool or freeze the cells for later processing, or the cells may be transferred to a cell concentration module 830 where the cells are rendered electrocompetent and concentrated to a volume optimal for cell transformation. Once concentrated, the cells are then transferred to an electroporation device 808 (e.g., transformation/transfection module). Exemplary electroporation devices of use in the automated multi-module cell processing instruments for use in the multi-module cell processing instrument include flow-through electroporation devices.

In addition to the reservoir for storing the cells, the system 800 may include a reservoir for storing editing cassettes 816 and a reservoir for storing an expression vector backbone 818. Both the editing oligonucleotide cassettes and the expression vector backbone are transferred from the reagent cartridge to a nucleic acid assembly module 828, where the editing oligonucleotide cassettes are inserted into the expression vector backbone. The assembled nucleic acids may be transferred into an optional purification module 822 for desalting and/or other purification and/or concentration procedures needed to prepare the assembled nucleic acids for transformation. Alternatively, pre-assembled nucleic acids, e.g., an editing vector, may be stored within reservoir 816 or 818. Once the processes carried out by the purification module 822 are complete, the assembled nucleic acids are transferred to, e.g., an electroporation device 808, which already contains the cell culture grown to a target OD and rendered electrocompetent via an optional filtration module (not shown). In electroporation device 808, the assembled nucleic acids are introduced into the cells. Following electroporation, the cells are transferred into a combined recovery/selection module 830. For examples of multi-module cell editing instruments, see U.S. Pat. Nos. 10,253,316; 10,329,559; 10,323,242; 10,421,959; 10,465,185; 10,519,437; 10,584,333; 10,584,334; and U.S. Ser. Nos. 16/412,195, filed 14 May 2019; 16/750,369, 23 Jan. 2020; 16/822,249, filed 18 Mar. 2020; and 16/837,985, filed 1 Apr. 2020, both of which are herein incorporated by reference in their entirety.

Following recovery, and, optionally, selection, the cells are transferred to a growth, induction, and editing module (bulk liquid culture) 840. The cells are allowed to grow until the cells reach the stationary growth phase (or nearly so), then editing is induced by induction of transcription of one or both of the nuclease and gRNA. In some embodiments, editing is induced by transcription of one or both of the nuclease and the gRNA being under the control of an inducible promoter. In some embodiments, the inducible promoter is a pL promoter where the promoter is activated by a rise in temperature and "deactivated" by lowering the temperature.

The recovery, selection, growth, induction, editing and storage modules may all be separate, may be arranged and combined as shown in FIG. 8, or may be arranged or combined in other configurations. In certain embodiments, recovery and selection are performed in one module, and growth, editing, and re-growth are performed in a separate module. Alternatively, recovery, selection, growth, editing, and re-growth are performed in a single module.

Once the cells are edited and re-grown (e.g., recovered from editing), the cells may be stored, e.g., in a storage module 812, where the cells can be kept at, e.g., 4° C. until the cells are used in another round of editing or retrieved 814. The multi-module cell processing instrument is controlled by a processor 824 configured to operate the instrument based on user input, as directed by one or more scripts, or as a combination of user input or a script. The processor 824 may control the timing, duration, temperature, and operations of the various modules of the system 800 and the dispensing of reagents. For example, the processor 824 may cool the cells post-transformation until editing is desired, upon which time the temperature may be raised to a temperature conducive of genome editing and cell growth. The processor may be programmed with standard protocol parameters from which a user may select, a user may specify one or more parameters manually or one or more scripts associated with the reagent cartridge may specify one or more operations and/or reaction parameters. In addition, the processor may notify the user (e.g., via an application to a smart phone or other device) that the cells have reached the target OD as well as update the user as to the progress of the cells in the various modules in the multi-module system.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example I: Growth in the Cell Growth Module

One embodiment of the cell growth device as described herein was tested against a conventional cell shaker shaking a 5 ml tube and an orbital shaker shaking a 125 ml baffled flask to evaluate cell growth in bacterial and yeast cells. Additionally, growth of a bacterial cell culture and a yeast cell culture was monitored in real time using an embodiment of the cell growth device described herein in relation to FIGS. 3A-3D.

Figure 9:
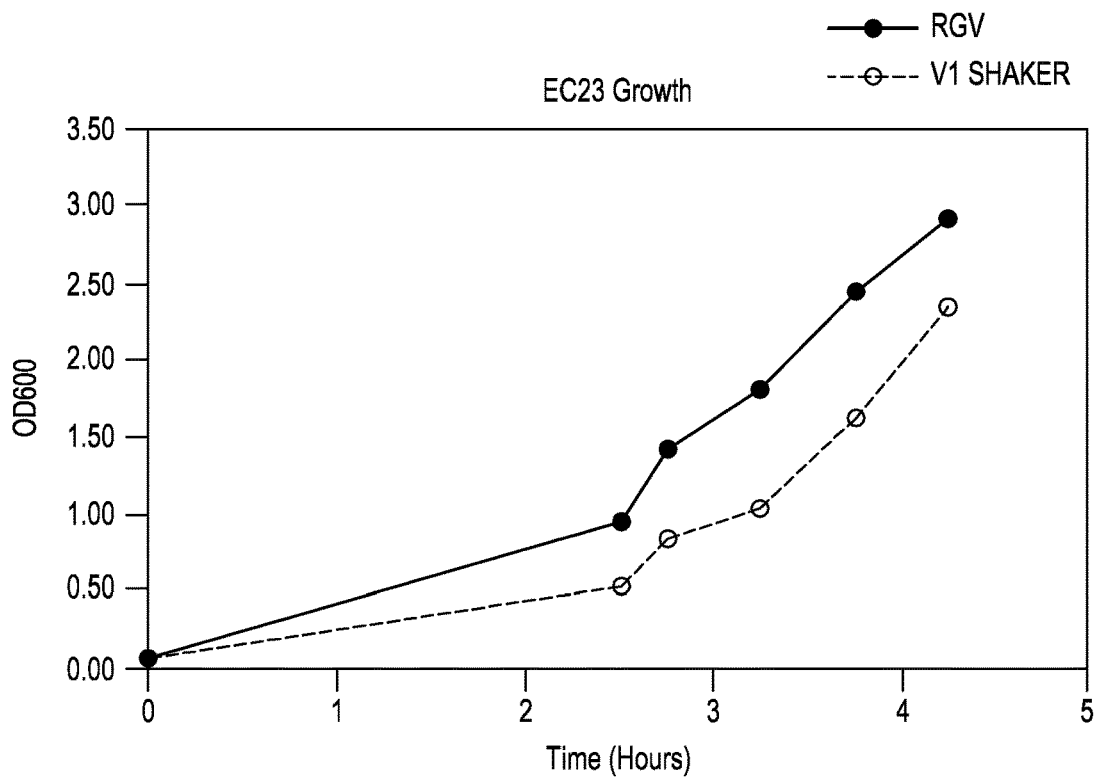
FIG. 9 is a graph demonstrating the effectiveness of a 2-paddle rotating growth vial and cell growth device as described herein for growing an EC23 cell culture vs. a conventional cell shaker.
Figure 10:
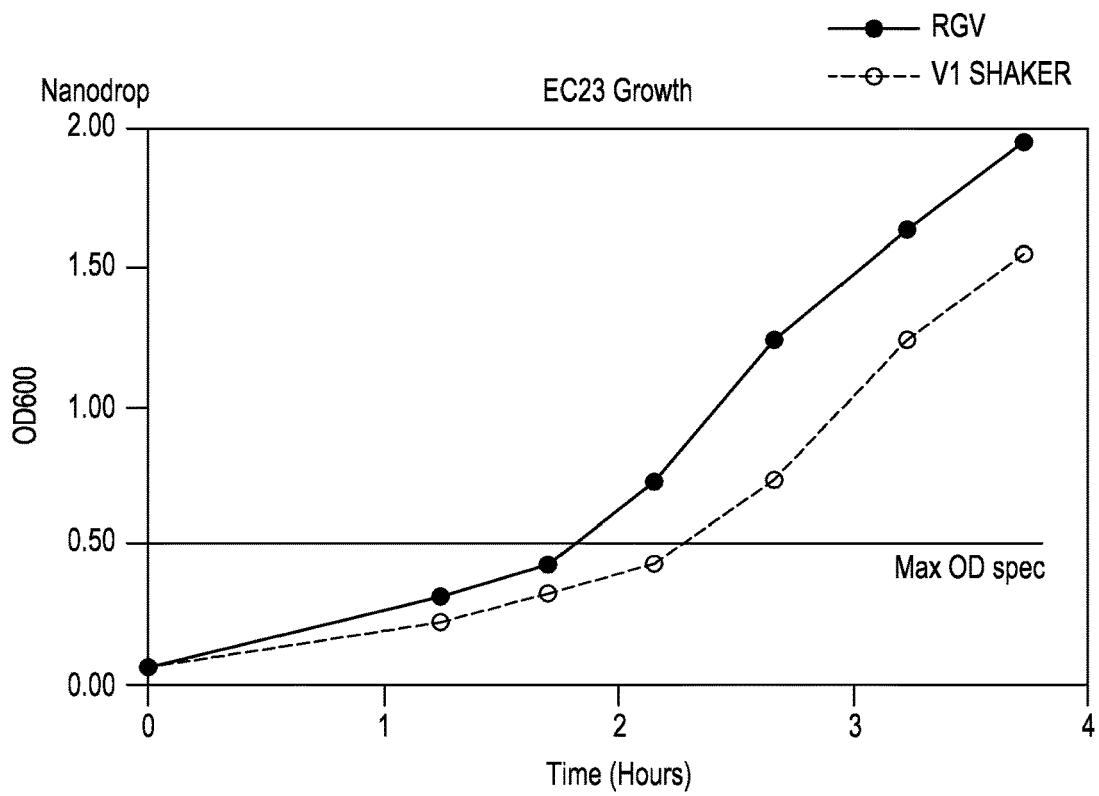
FIG. 10 is a graph demonstrating the effectiveness of a 3-paddle rotating growth vial and cell growth device as described herein for growing an EC23 cell culture vs. a conventional cell shaker.

In a first example, 20 ml EC23 cells (*E. coli* cells) in LB were grown in a 35 ml rotating growth vial with a 2-paddle configuration at 30° C. using the cell growth device as described herein. The rotating growth vial was spun at 600 rpm and oscillated (i.e., the rotation direction was changed) every 1 second. In parallel, 5 ml EC23 cells in LB were grown in a 5 ml tube at 30° C. and were shaken at 750 rpm. $OD_{600}$ was measured at intervals using a NanoDrop™ spectrophotometer (Thermo Fisher Scientific). The results are shown in FIG. 9. The rotating growth vial/cell growth device performed better than the cell shaker in growing the cells to $OD_{600}$ 2.6 in slightly over 4 hours. Another experiment was performed with the same conditions (volumes, cells, oscillation) the only difference being a 3-paddle rotating growth vial was employed with the cell growth device, and the results are shown in FIG. 10. Again, the rotating growth vial/cell growth device performed better than the cell shaker in growing the cells to $OD_{600}$ 1.9.

Figure 11:
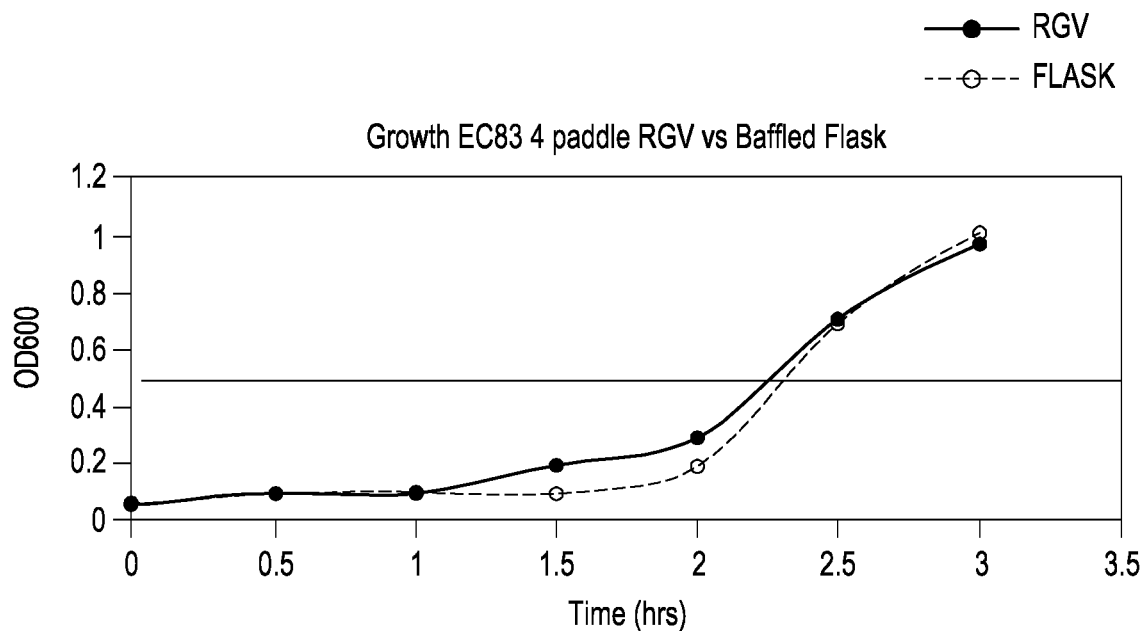
FIG. 11 is a graph demonstrating the effectiveness of a 4-paddle rotating growth vial and cell growth device as described herein for growing an EC138 cell culture vs. a conventional orbital cell shaker.
Figure 12:
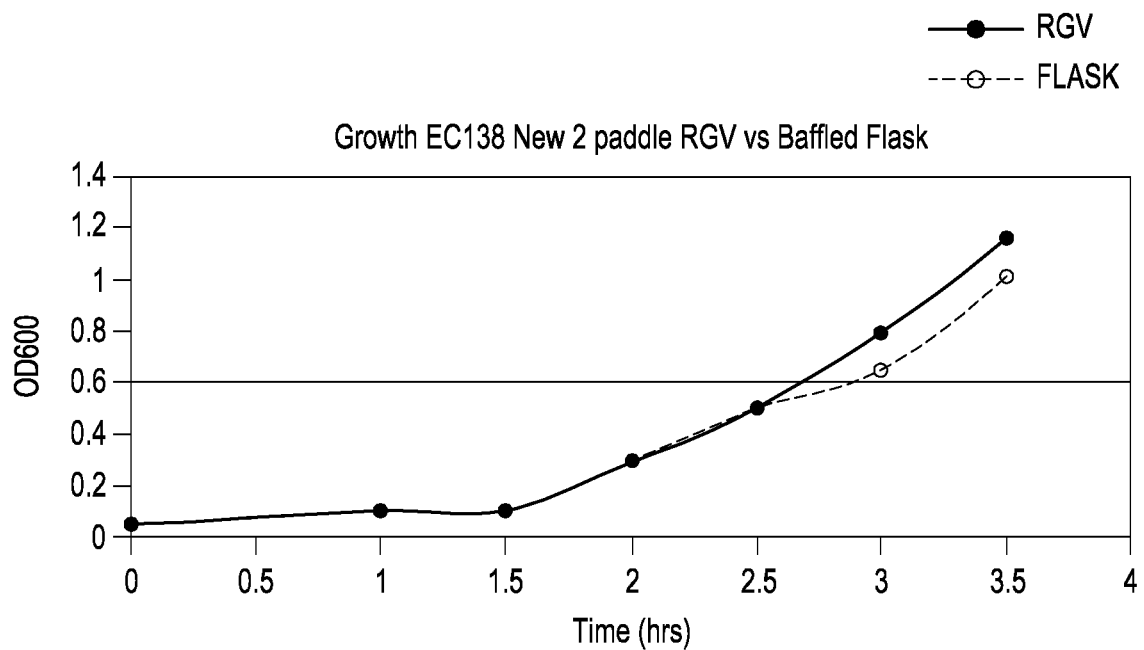
FIG. 12 is a graph demonstrating the effectiveness of a 2-paddle rotating growth vial and cell growth device as described herein for growing an EC138 cell culture vs. a conventional orbital cell shaker.

Two additional experiments were performed, this time comparing the rotating growth vial/cell growth device to a baffled flask and an orbital shaker. In one experiment, 20 ml EC138 cells (*E. coli* cells) in LB were grown in a 35 ml rotating growth vial with a 4-paddle configuration at 30° C. The rotating growth vial was spun at 600 rpm and oscillated (i.e., the rotation direction was changed) every 1 second. In parallel, 20 ml EC138 cells in LB were grown in a 125 ml baffled flask at 30° C. using an orbital shaker. $OD_{600}$ was measured at intervals using a NanoDrop™ spectrophotometer (Thermo Fisher Scientific). The results are shown in FIG. 11, demonstrating that the rotating growth vial/cell growth device performed as well as the orbital shaker in growing the cells to $OD_{600}$ 1.0. In a second experiment 20 ml EC138 cells (*E. coli* cells) in LB were grown in a 35 ml rotating growth vial with a 2-paddle configuration at 30° C. using the cell growth device as described herein. The rotating growth vial was spun at 600 rpm and oscillated (i.e., the rotation direction was changed) every 1 second. In parallel, 20 ml EC138 cells in LB were grown in a 125 ml baffled flask at 30° C. using an orbital shaker. $OD_{600}$ was measured at intervals using a NanoDrop™ spectrophotometer (Thermo Fisher Scientific). The results are shown in FIG. 12, demonstrating that the rotating growth vial/cell growth device performed as well—or better—as the orbital shaker in growing the cells to $OD_{600}$ 1.2.

Figure 13:
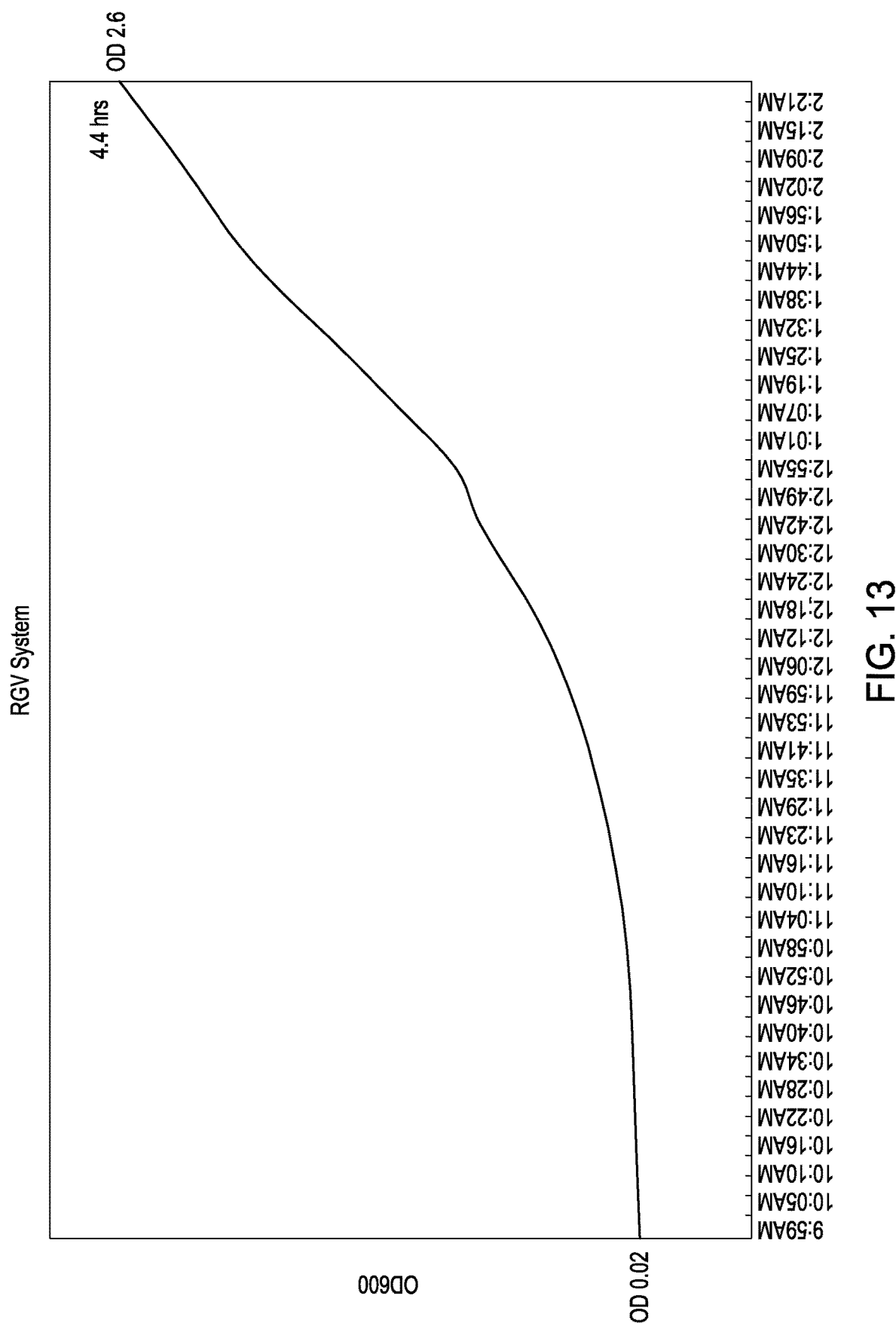
FIG. 13 is a graph demonstrating real-time monitoring of growth of an EC138 cell culture to $OD_{600}$ employing the cell growth device as described herein where a 2-paddle rotating growth vial was used.

In yet another experiment, the rotating growth vial/cell growth device was used to measure $OD_{600}$ in real time. FIG. 13 is a graph showing the results of real time measurement of growth of an EC138 cell culture at 30° C. using oscillating rotation and employing a 2-paddle rotating growth vial. Note that $OD_{600}$ 2.6 was reached in 4.4 hours.

Figure 14:
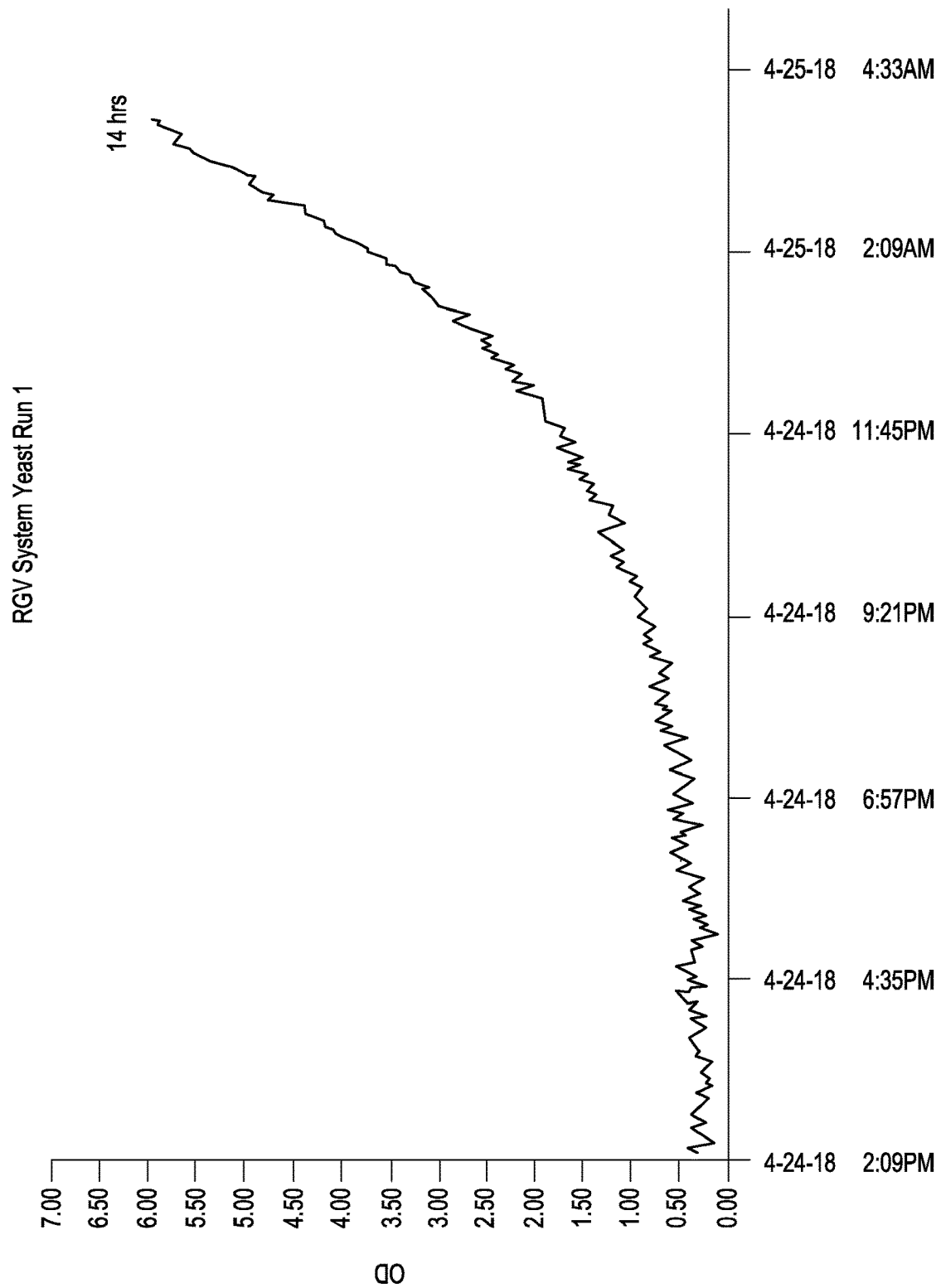
FIG. 14 is a graph demonstrating real-time monitoring of growth of s288c yeast cell culture $OD_{600}$ employing the cell growth device as described herein where a 2-paddle rotating growth vial was used.

In another experiment, the rotating growth vial/cell growth device was used to measure $OD_{600}$ in real time of yeast s288c cells in YPAD. The cells were grown at 30° C. using oscillating rotation and employing a 2-paddle rotating growth vial. FIG. 14 is a graph showing the results. Note that $OD_{600}$ 6.0 was reached in 14 hours.

Example II: Cell Concentration

The TFF module as described above in relation to FIGS. 4A-4E has been used successfully to process and perform buffer exchange on both *E. coli* and yeast cultures. In concentrating an *E. coli* culture, the following steps were performed:

First, a 20 ml culture of *E. coli* in LB grown to OD 0.5-0.62 was passed through the TFF device in one direction, then passed through the TFF device in the opposite direction. At this point the cells were concentrated to a volume of approximately 5 ml. Next, 50 ml of 10% glycerol was added to the concentrated cells, and the cells were passed through the TFF device in one direction, in the opposite direction, and back in the first direction for a total of three passes. Again the cells were concentrated to a volume of approximately 5 ml. Again, 50 ml of 10% glycerol was added to the 5 ml of cells and the cells were passed through the TFF device for three passes. This process was repeated; that is, again 50 ml 10% glycerol was added to cells concentrated to 5 ml, and the cells were passed three times through the TFF device. At the end of the third pass of the three 50 ml 10% glycerol washes, the cells were again concentrated to approximately 5 ml of 10% glycerol. The cells were then passed in alternating directions through the TFF device three more times, wherein the cells were concentrated into a volume of approximately 400 µl.

Figure 15A:
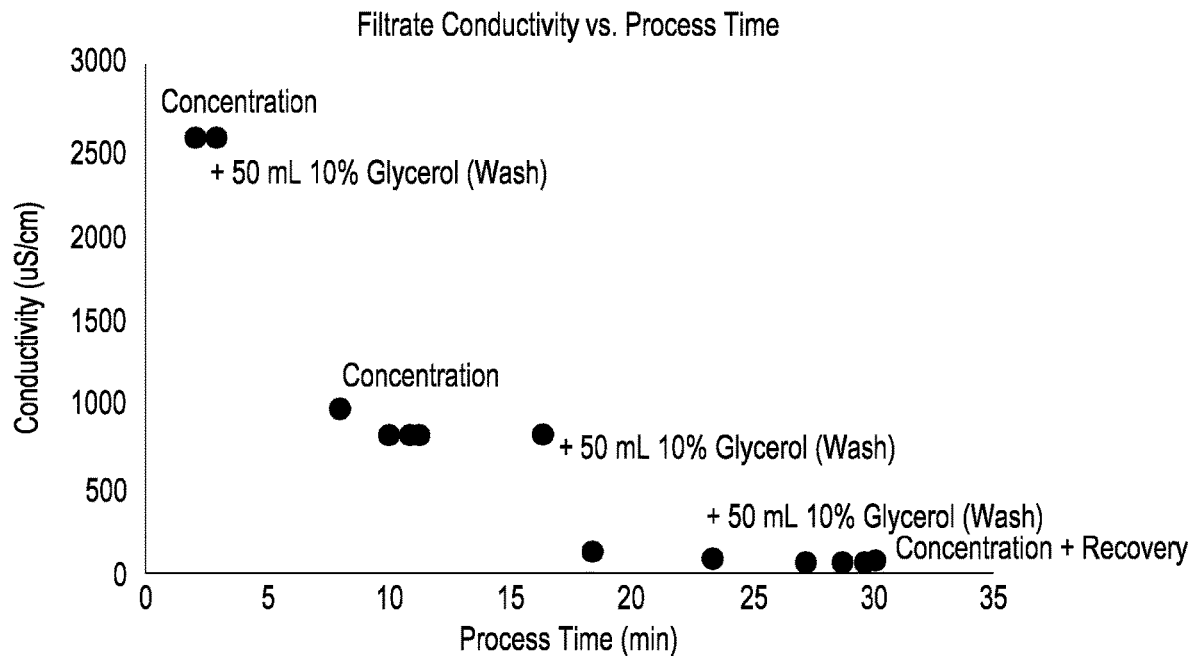
FIG. 15A is a graph plotting filtrate conductivity against filter processing time for an E. coli culture processed in the cell concentration device/module described herein.

Filtrate conductivity and filter processing time was measured for *E. coli* with the results shown in FIG. 15A. Filter performance was quantified by measuring the time and number of filter passes required to obtain a target solution electrical conductivity. Cell retention was determined by comparing the optical density (OD600) of the cell culture both before and after filtration. Filter health was monitored by measuring the transmembrane flow rate during each filter pass. Target conductivity (~16 µS/cm) was achieved in approximately 30 minutes utilizing three 50 ml 10% glycerol washes and three passes of the cells through the device for each wash. The volume of the cells was reduced from 20 ml to 400 and recovery of approximately 90% of the cells has been achieved.

Figure 15B:
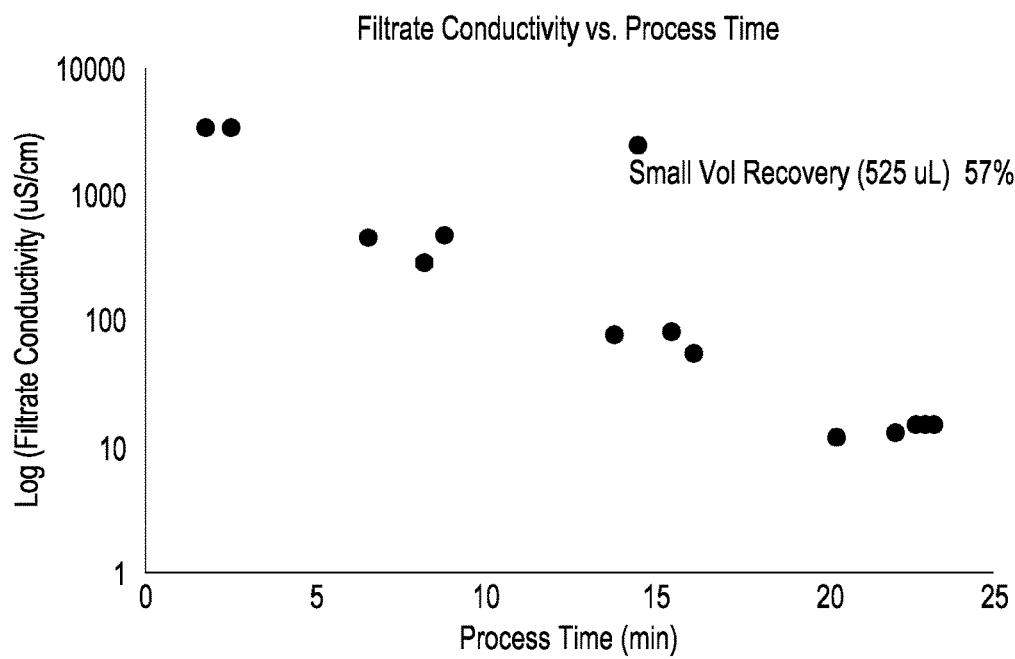
FIG. 15B is a graph plotting filtrate conductivity against filter processing time for a yeast culture processed in the cell concentration device/module described herein.

The same process was repeated with yeast cell cultures. A yeast culture was initially concentrated to approximately 5 ml using two passes through the TFF device in opposite directions. The cells were washed with 50 ml of 1M sorbitol three times, with three passes through the TFF device after each wash. After the third pass of the cells following the last wash with 1M sorbitol, the cells were passed through the TFF device two times, wherein the yeast cell culture was concentrated to approximately 525 µl. FIG. 15B presents the filter buffer exchange performance for yeast cells determined by measuring filtrate conductivity and filter processing time. Target conductivity (~10 µS/cm) was achieved in approximately 23 minutes utilizing three 50 ml 1M sorbitol washes and three passes through the TFF device for each wash. The volume of the cells was reduced from 20 ml to 525 µl. Recovery of approximately 90% of the cells has been achieved.

Example III: Production and Transformation of Electrocompetent E. coli and S. Cerevisiae For testing transformation of the FTEP device, electrocompetent E. coli cells were created. To create a starter culture, 6 ml volumes of LB chlor-25 (LB with 25 µg/ml chloramphenicol) were transferred to 14 ml culture tubes. A 25 µl aliquot of E. coli was used to inoculate the LB chlor-25 tubes. Following inoculation, the tubes were placed at a 45° angle in the shaking incubator set to 250 RPM and 30° C. for overnight growth, between 12-16 hrs. The OD600 value should be between 2.0 and 4.0. A 1:100 inoculum volume of the 250 ml LB chlor-25 tubes were transferred to four sterile 500 ml baffled shake flasks, i.e., 2.5 ml per 250 ml volume shake flask. The flasks were placed in a shaking incubator set to 250 RPM and 30° C. The growth was monitored by measuring OD600 every 1 to 2 hr. When the OD600 of the culture was between 0.5-0.6 (approx. 3-4 hrs), the flasks were removed from the incubator. The cells were centrifuged at 4300 RPM, 10 min, 4° C. The supernatant was removed, and 100 ml of ice-cold 10% glycerol was transferred to each sample. The cells were gently resuspended, and the wash procedure performed three times, each time with the cells resuspended in 10% glycerol. After the fourth centrifugation, the cell resuspension was transferred to a 50 ml conical Falcon tube and additional ice-cold 10% glycerol added to bring the volume up to 30 ml. The cells were again centrifuged at 4300 RPM, 10 min, 4° C., the supernatant removed, and the cell pellet resuspended in 10 ml ice-cold glycerol. The cells were aliquoted in 1:100 dilutions of cell suspension and ice-cold glycerol.

The comparative electroporation experiment was performed to determine the efficiency of transformation of the electrocompetent E. coli using the FTEP device described. The flow rate was controlled with a pressure control system. The suspension of cells with DNA was loaded into the FTEP inlet reservoir. The transformed cells flowed directly from the inlet and inlet channel, through the flow channel, through the outlet channel, and into the outlet containing recovery medium. The cells were transferred into a tube containing additional recovery medium, placed in an incubator shaker at 30° C. shaking at 250 rpm for 3 hours. The cells were plated to determine the colony forming units (CFUs) that survived electroporation and failed to take up a plasmid and the CFUs that survived electroporation and took up a plasmid. Plates were incubated at 30° C.; E. coli colonies were counted after 24 hrs.

Figure 16A:
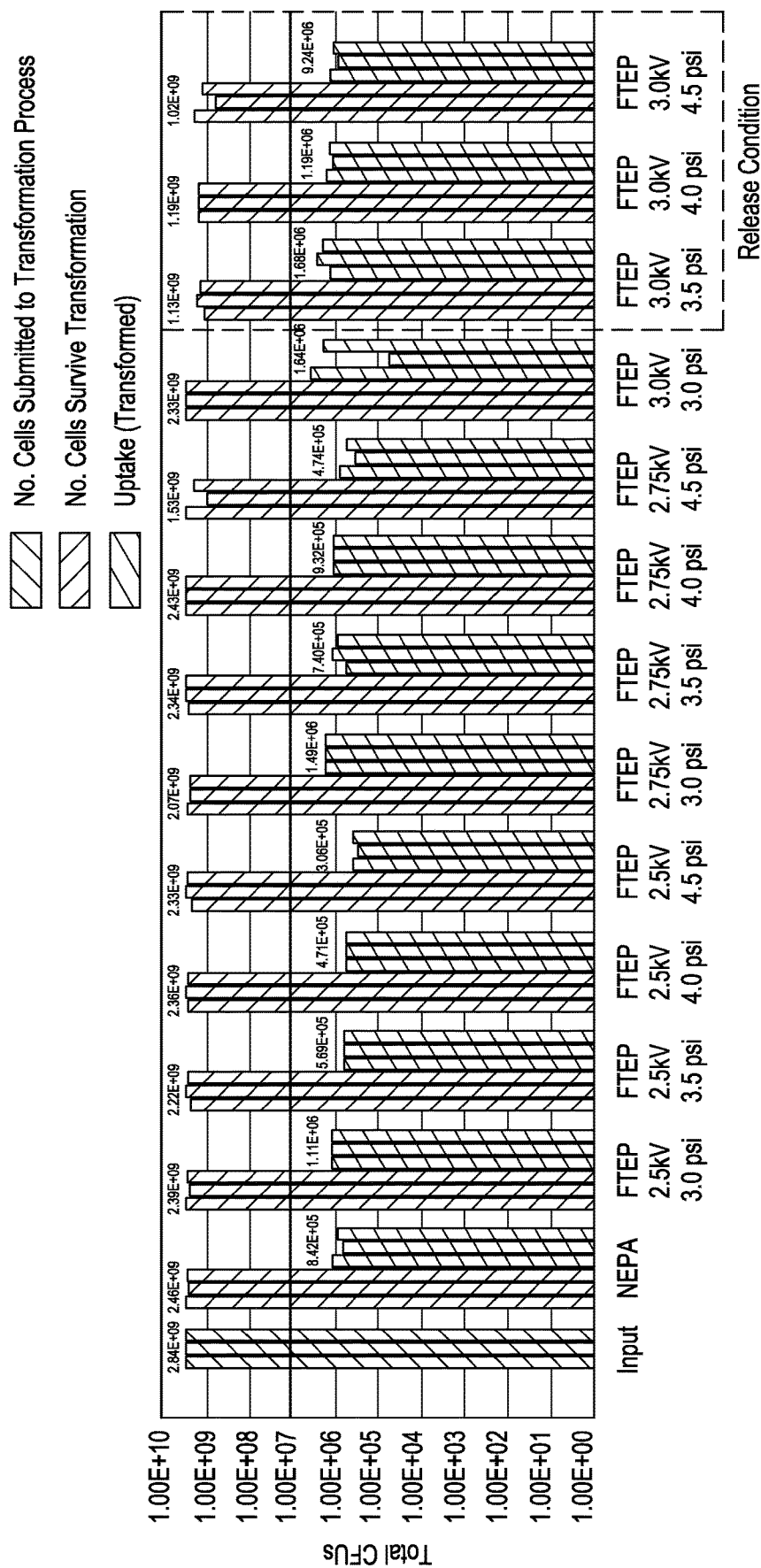
FIG. 16A is a bar graph showing the results of electroporation of E. coli using a device of the disclosure and a comparator electroporation device.

The flow-through electroporation experiments were benchmarked against 2 mm electroporation cuvettes (Bull dog Bio) using an in vitro high voltage electroporator (NEPAGENE™ ELEPO21). Stock tubes of cell suspensions with DNA were prepared and used for side-to-side experiments with the NEPAGENE™ and the flow-through electroporation. The results are shown in FIG. 16A. In FIG. 16A, the left-most bars hatched /// denote cell input, the bars to the left bars hatched \\\ denote the number of cells that survived transformation, and the right bars hatched /// denote the number of cells that were actually transformed. The FTEP device showed equivalent transformation of electrocompetent E. coli cells at various voltages as compared to the NEPAGENE™ electroporator. As can be seen, the transformation survival rate is at least 90% and in some embodiments is at least 95%, 96%, 97%, 98%, or 99%. The recovery ratio (the fraction of introduced cells which are successfully transformed and recovered) is in certain embodiments at least 0.001 and preferably between 0.00001 and 0.01. In FIG. 16A the recovery ratio is approximately 0.0001.

Figure 16B:
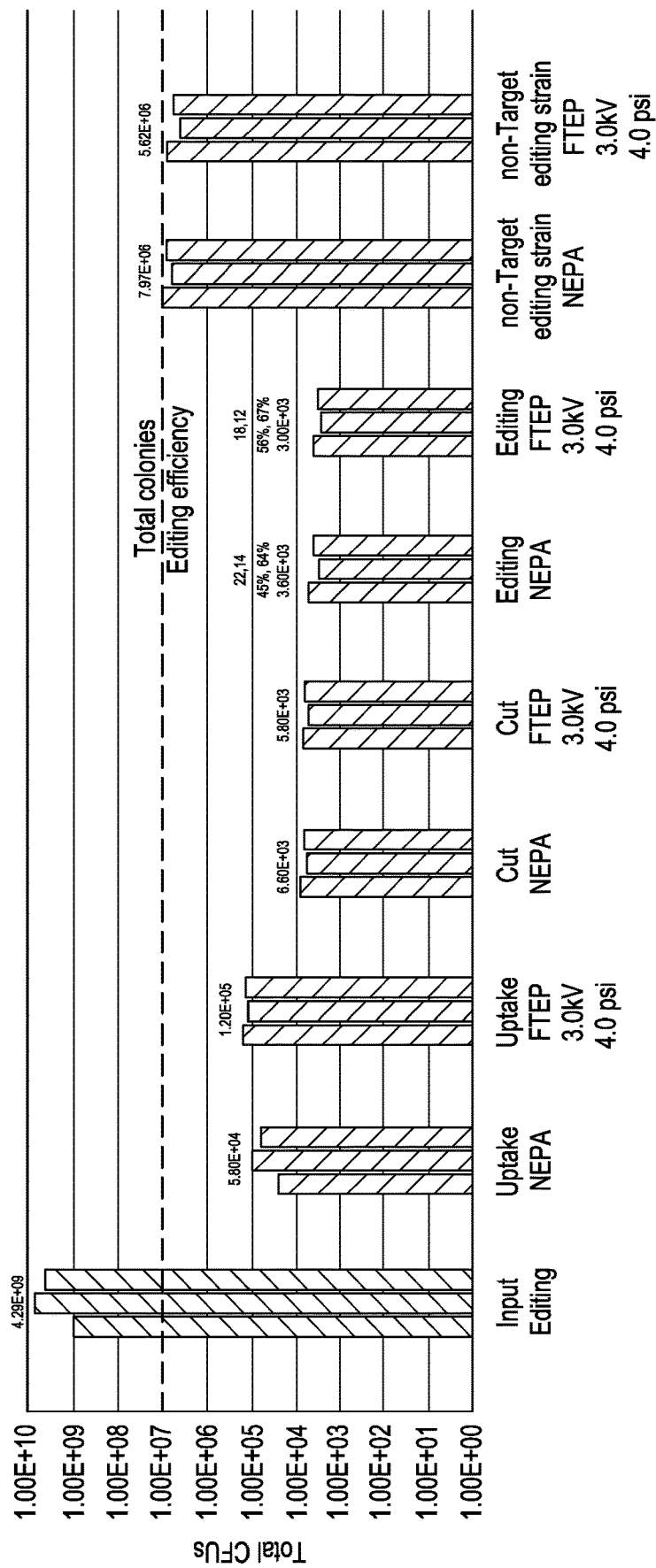
FIG. 16B is a bar graph showing uptake, cutting, and editing efficiencies of E. coli cells transformed via an FTEP as described herein benchmarked against a comparator electroporation device.

Additionally, a comparison of the NEPAGENE™ ELEPO21 and the FTEP device was made for efficiencies of transformation (uptake), cutting, and editing. In FIG. 16B, triplicate experiments were performed where the bars hatched /// denote the number of cells input for transformation, and the bars hatched \\\ denote the number of cells that were transformed (uptake), the number of cells where the genome of the cells was cut by a nuclease transcribed and translated from a vector transformed into the cells (cutting), and the number of cells where editing was effected (cutting and repair using a nuclease transcribed and translated from a vector transformed into the cells, and using a guide RNA and a donor DNA sequence both of which were transcribed from a vector transformed into the cells). Again, it can be seen that the FTEP showed equivalent transformation, cutting, and editing efficiencies as the NEPAGENE™ electroporator. The recovery rate in FIG. 16B for the FTEP is greater than 0.001.

For testing transformation of the FTEP device in yeast, S. cerevisiae cells were created using the methods as generally set forth in Bergkessel and Guthrie, Methods Enzymol., 529:311-20 (2013). Briefly, YFAP media was inoculated for overnight growth, with 3 ml inoculate to produce 100 ml of cells. Every 100 ml of culture processed resulted in approximately 1 ml of competent cells. Cells were incubated at 30° C. in a shaking incubator until they reached an OD600 of 1.5+/−0.1.

A conditioning buffer was prepared using 100 mM lithium acetate, 10 mM dithiothreitol, and 50 mL of buffer for every 100 mL of cells grown and kept at room temperature. Cells were harvested in 250 ml bottles at 4300 rpm for 3 minutes, and the supernatant removed. The cell pellets were suspended in 100 ml of cold 1 M sorbitol, spun at 4300 rpm for 3 minutes and the supernatant once again removed. The cells were suspended in conditioning buffer, then the suspension transferred into an appropriate flask and shaken at 200 RPM and 30° C. for 30 minutes. The suspensions were transferred to 50 ml conical vials and spun at 4300 rpm for 3 minutes. The supernatant was removed and the pellet resuspended in cold 1 M sorbitol. These steps were repeated three times for a total of three wash-spin-decant steps. The pellet was suspended in sorbitol to a final OD of 150+/−20.

A comparative electroporation experiment was performed to determine the efficiency of transformation of the electrocompetent S. cerevisiae using the FTEP device. The flow rate was controlled with a syringe pump (Harvard apparatus PHD ULTRA™ 4400). The suspension of cells with DNA was loaded into a 1 mL glass syringe (Hamilton 81320 Syringe, PTFE Luer Lock) before mounting on the pump. The output from the function generator was turned on immediately after starting the flow. The processed cells flowed directly into a tube with 1M sorbitol with carbenicillin. Cells were collected until the same volume electroporated in the NEPAGENE™ had been processed, at which point the flow and the output from the function generator were stopped. After a 3-hour recovery in an incubator shaker at 30° C. and 250 rpm, cells were plated to determine the colony forming units (CFUs) that survived electroporation and failed to take up a plasmid and the CFUs that survived electroporation and took up a plasmid. Plates were incubated at 30° C. Yeast colonies are counted after 48-76 hrs.

Figure 17:
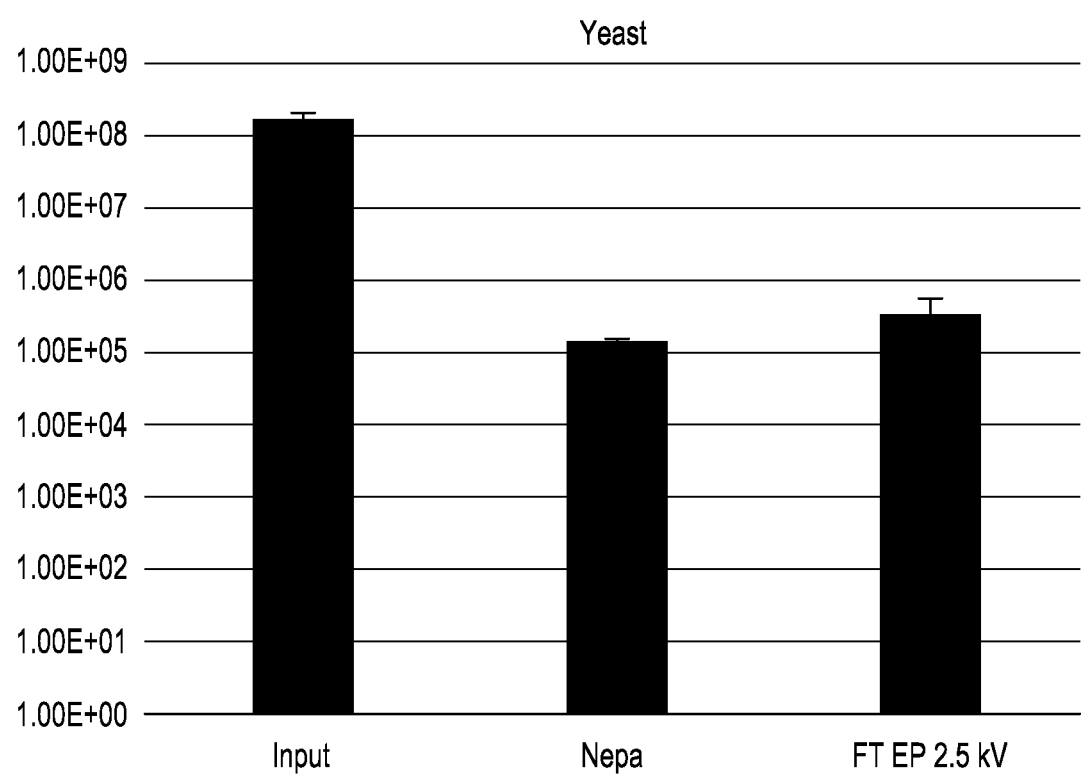
FIG. 17 is a bar graph showing the results of electroporation of S. cerevisiae using an FTEP device of the disclosure and a comparator electroporation method.

The flow-through electroporation experiments were benchmarked against 2 mm electroporation cuvettes (Bull dog Bio) using an in vitro high voltage electroporator (NEPAGENE™ ELEPO21). Stock tubes of cell suspensions with DNA were prepared and used for side-to-side experiments with the NEPAGENE™ and the flow-through electroporation. The results are shown in FIG. 17. The device showed better transformation and survival of electrocompetent S. Cerevisiae at 2.5 kV voltages as compared to the NEPAGENE™ method. Input is total number of cells that were processed.

Example IV: Bulk Liquid Protocol: Induction and Outgrowth 250 mL baffled shake flasks were prepared with 50 mL of SOB+100 µg/mL carbenicillin and 25 µg/mL chloramphenicol. For a full, deconvolution experiment, 3 shake flasks were prepared per transformation. 500 µL of undiluted culture from each transformation reaction was transferred into the prepared 250 mL shake flasks. The following temperature settings were set up on an incubator: 30° C. for 9 hours→42° C. for 2 hours→30° C. for 9 hours. This temperature regime was used to allow for additional recovery of the cells from transformation during the first eight hours. The lambda red system was induced one hour prior to induction of the nuclease, where lambda induction was triggered by the addition of arabinose (2.5 mL of 20% arabinose) to the culture, and the nuclease induction was triggered by increasing the temperature of the cultures to 42° C. For full deconvolution experiments, arabinose was not added to the UPTAKE and CUT flasks as those should not express lambda red; further, the UPTAKE flasks were not shifted to 42° C.

After the temperature cycling is complete (~21 hours), the shake flasks were removed. For NGS-SinglePlex: serial dilutions of $10^{-5}$ to $10^{-7}$ of each culture were prepared with 0.8% NaCl (50 µL of culture into 450 µL of sterile, 0.8% NaCl). Following dilution, 300 µL of each dilution was plated onto 150 mm LB agar plates with standard concentrations of chloramphenicol and carbenicillin. The plates were then placed in a 30° C. incubator for overnight growth and were picked for singleplex NGS the following day. For NGS-Amplicon: 250 µL of culture from each shake flask was removed and used as the input for a plasmid extraction protocol. The OD of this culture was measured to select a volume based on the desired number of cells to go into the plasmid purification. Optionally, an undiluted volume from each shake flask may be plated to see enrichment/depletion of cassettes and the plates were scraped the following day and processed.

Figure 18:
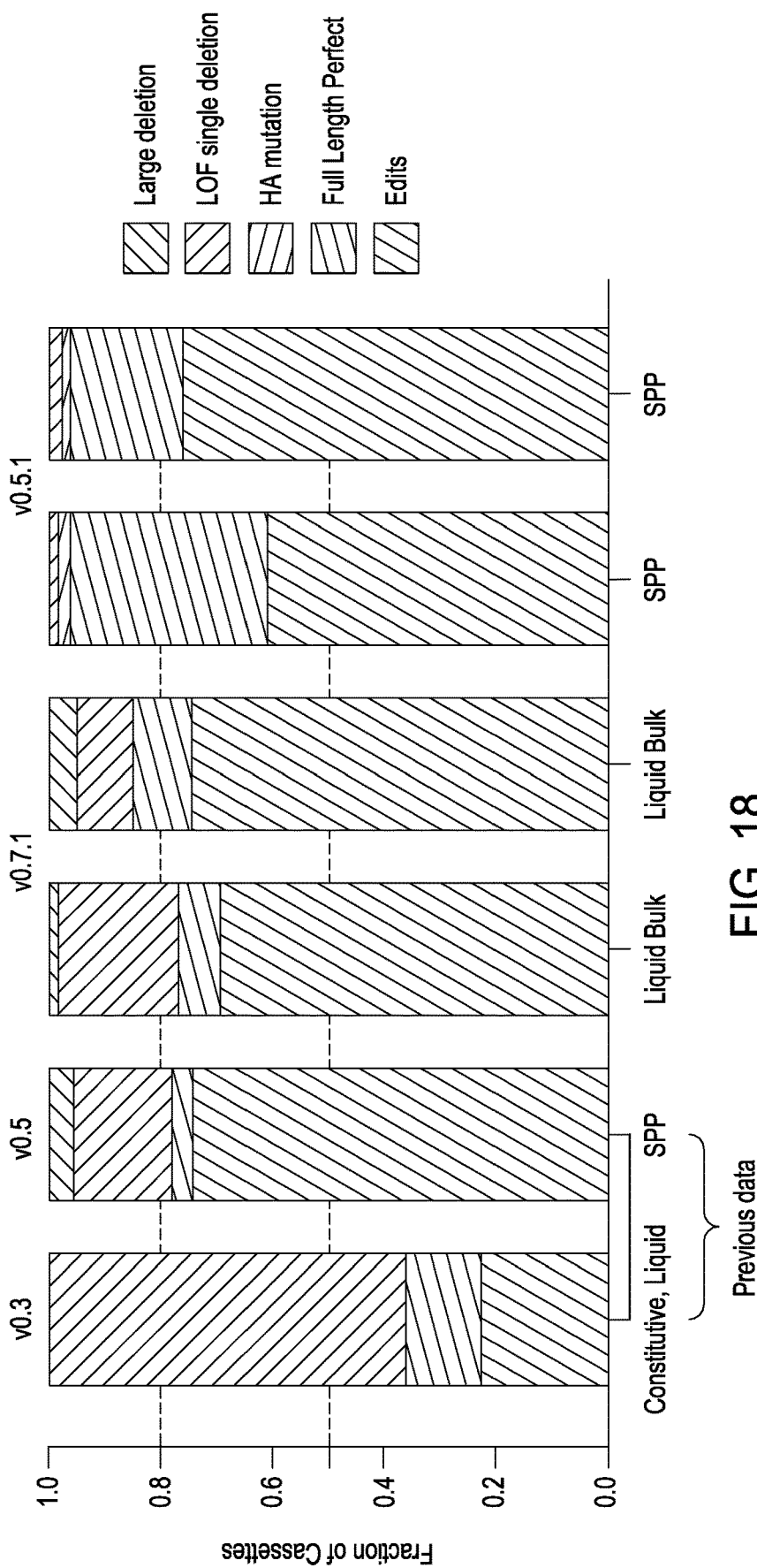
FIG. 18 is a graph showing the editing results obtained via the liquid bulk method for increasing observed editing in live cells.

FIG. 18 is a bar graph showing the various types of edits observed using constitutive editing in a liquid culture (approximately 20% editing observed), standard plating procedure (approximately 76% editing observed), two replica experiments of induced editing in liquid bulk (approximately 70% and 76% editing observed), and two replica experiments of induced editing using the standard plating procedure (approximately 60% and 76% editing observed). Editing clonality was also measured. The editing clonality of the standard plating procedure showed mixed clonality for the 96 wells, with some colonies achieving 100% clonality, most colonies achieving greater than 50% clonality, and an average clonality of 70% and 60% for two replicates (data not shown). The editing clonality of the liquid bulk procotol shows that the majority of the cells were either 100% edited, or 0% edited (e.g., wildtype), with a small number (approximately 8%) between 100% or 0%. The average editing efficiency was similar for these protocols.

Example V: Singulation, Growth and Editing of E. coli in 200K SWIIN

Singleplex automated genomic editing using MAD7 nuclease, a library with 94 different edits in a single gene (yagP) and employing a 200K singulation device such as those exemplified in FIGS. 6B-6E was successfully performed. The engine vector used comprised MAD7 under the control of the pL inducible promoter, and the editing vector used comprised the editing cassette being under the control of the pL inducible promoter, and the λ Red recombineering system under control of the pBAD inducible promoter pBAD—with the exception that the editing cassette comprises the 94 yagP gene edits (donor DNAs) and the appropriate corresponding gRNAs. Two SWIIN workflows were compared, and further were benchmarked against the standard plating protocol. The SWIIN protocols differ from one another that in one set of replicates LB medium containing arabinose was used to distribute the cells in the SWIIN (arabinose was used to induce the λ Red recombineering system (which allows for repair of double-strand breaks in E. coli that are created during editing), and in the other set of replicates SOB medium without arabinose was used to distribute the cells in the SWIIN and for initial growth, with medium exchange performed to replace the SOB medium without arabinose with SOB medium with arabinose. Approximately 70K cells were loaded into the 200K SWIIN.

Figure 19:
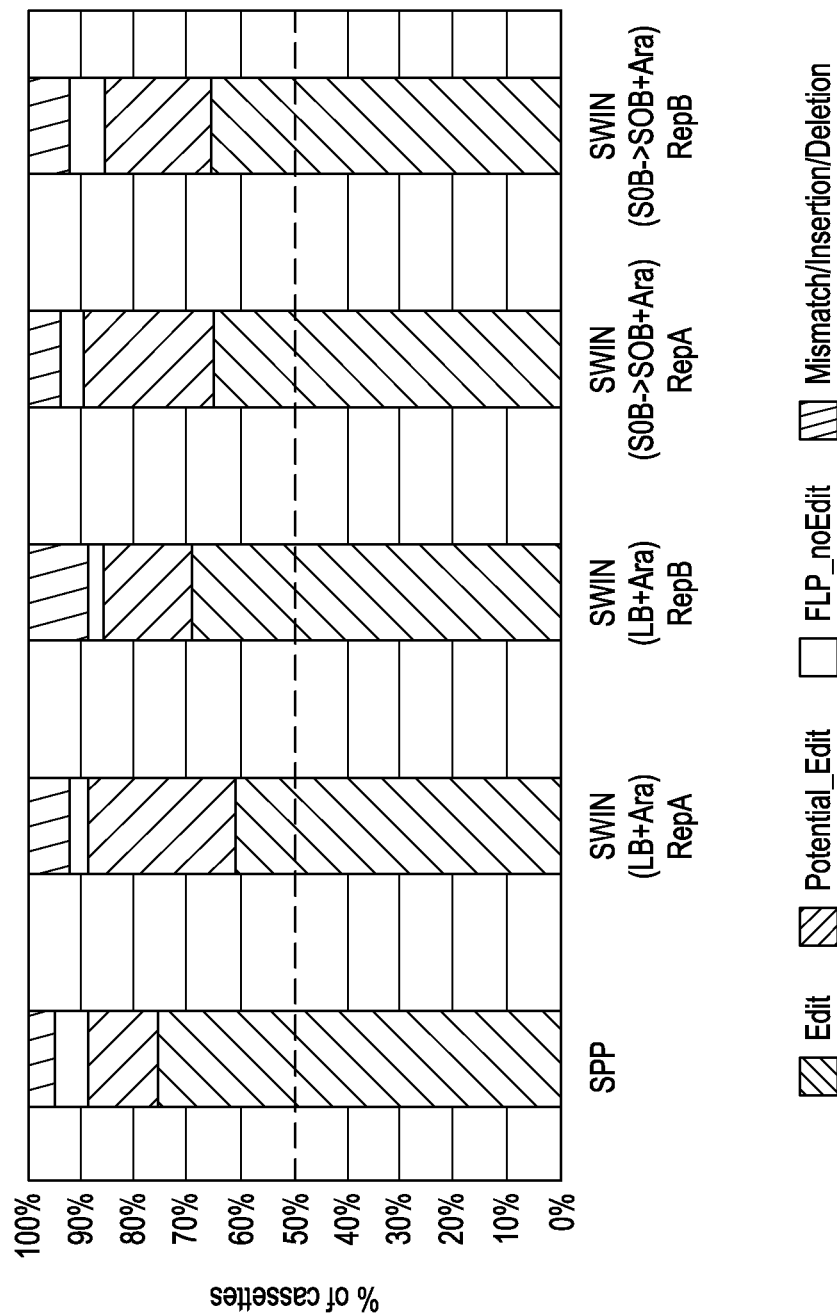
FIG. 19 is a graph comparing the percentage of editing obtained for a standard plating protocol (SPP), and replicate samples using two different conditions in a solid wall isolation, induction, and normalization device (SWIIN): the first with LB+arabinose; and the second with SOB followed by SOB+arabinose.

In all protocols (standard plating, LB-SWIIN, and SOB-SWIIN), the cells were allowed to grow at 30° C. for 9 hours and editing was induced by raising the temperature to 42° C. for 2.5 hours, then the temperature was returned to 30° C. and the cells were grown overnight. The results of this experiment are shown in FIG. 19 and in Table 1 below. Note that similar editing performance was observed with the four replicates of the two SWIIN workflows, indicating that the performance of SWIIN plating with and without arabinose in the initial medium is similar. Editing percentage in the standard plating protocol was approximately 77%, in bulk liquid was approximately 67%, and for the SWIIN replicates ranged from approximately 63% to 71%. Note that the percentage of unique edit cassettes divided by the total number of edit cassettes was similar for each protocol.

TABLE 1

|  | Standard Plating | SWIIN LB/Ara Rep. A | SWIIN LB/Ara Rep. B | SWIIN SOB then SOB/Ara Rep. A | SWIIN SOB then SOB/Ara Rep. B |
| --- | --- | --- | --- | --- | --- |
| 40006 edit calls/ identified wells | 0.777 | 0.633 | 0.719 | 0.663 | 0.695 |
| Unique edit cassettes/ total edit cassettes | 0.49 | 0.49 | 0.43 | 0.50 | 0.51 |

Example VI: Curing

Standard Plating Protocol: Three rounds of recursive editing and curing were performed. Intended edits introduced a stop codon in three sugar genes (XylA-Y194*, LacZ-F593*, and GalK-E249*). These mutations cause a loss of function in the target gene. This loss of function phenotype was observed by growing cells on MacConkey medium. The editing rate was determined by calculating the ratio of the number of cells with a loss of function mutation to the number of total cells. E. coli 181 cells comprising the engine vector depicted in FIG. 1C on left were made competent and transformed in a 100 µL volume with the editing vector depicted in FIG. 1C on right. The cells were allowed to recover for 3 hours in 3.0 mL total volume SOB medium. The recovered cells were then diluted 1:100 in 20 mL SOB medium containing chloramphenicol and the appropriate antibiotic for the editing vector. The cells were then plated on solid SOB medium containing chloramphenicol, the editing vector antibiotic (e.g., carbenicillin, kanamycin, bleomycin, streptomycin or nourseothricin N-acetyl transferase, and arabinose. The arabinose induces the pBAD promoter driving transcription of the λ Red recombinase system.

The cells were grown for 9 hours at 30° C., grown for 2 hours at 42° C. to induce the pL promoter driving transcription of the nuclease and editing gRNA, and then grown for another 9 hours at 30° C. The cells were scraped from the plate and diluted in SOB medium with chloramphenicol only. The cells were then washed 3× and 8 mL of cells were suspended in 12 mL SOB+chlor medium and grown to OD=3.0 to assure the cells were in stationary phase. The temperature of the culture was increased to 42° C. for two hours to induce the nuclease and 20 µL DAPG was added to a final concentration of 25 µM to induce transcription of the curing gRNA (e.g., the anti-pUC gRNA). The cells were grown at 30° C. for 6 hours. Following curing, the cells were washed in LB+chlor medium, resuspended in LB+chlor medium and grown again at 30° C. to OD=0.5. The cells were washed three times with 10% glycerol to render them electrocompetent and subjected to another round of editing. The engine vector was maintained throughout the rounds of editing. The succession of editing vectors comprised the same editing vector architecture as shown in at right in FIG. 1C; however, the editing gRNA/donor DNA and the selectable marker changed with each round. The editing gRNAs and editing vector antibiotic resistance genes used for each round of editing and curing are listed in Table 2.

TABLE 2

| SPP experimental description | | | |
|---|---|---|---|
| Round | 1 | 2 | 3 |
| gRNA type | editing | editing | editing |
| Editing locus | LacZ | GalK | XylA |
| Editing vector Abx | Carb | Nat | Kan |

Figure 20A:
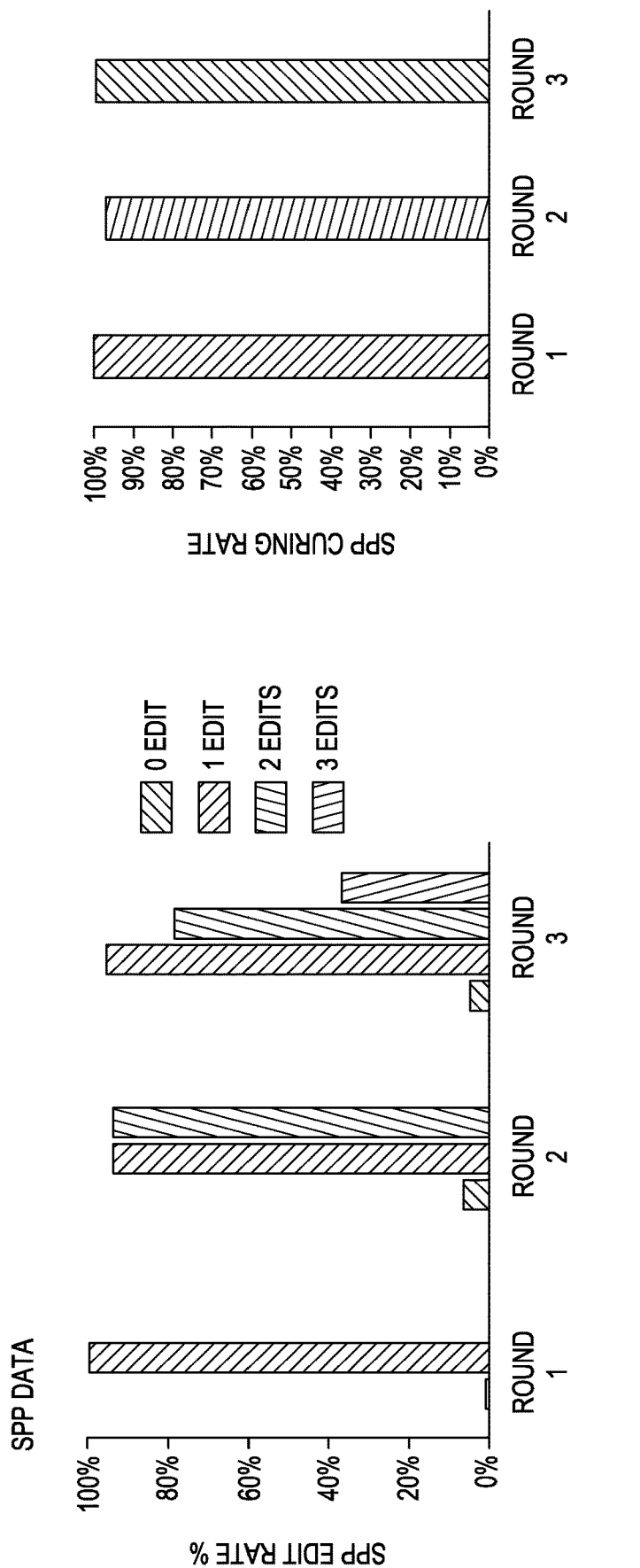
FIGS. 20A, 20B, and 20C are graphs of results obtained in experiments testing editing efficiency and curing efficiency in engine vector-driven recursive experiments performed by a standard plating protocol, a bulk liquid protocol, and a SWIIN protocol.

The results for both editing and curing rates are shown in FIG. 20A. For editing efficiency, note that after a first round of editing, 99% of cells had one edit; after a second round of editing a small percentage of cells had zero edits, approximately 95% of cells had one edit, approximately 95% of cells had two edits; and after a third round of editing, a small percentage of cells had zero edits, approximately 90% of cells had one edit, approximately 80% of cells had two edits, and approximately 38% of cells had all three edits. Note that these numbers are the fraction of cells that have at least 1, 2, or 3 edits; thus, if a cell has three edits it counts for each category, that is, it is the cumulative editing rate. Curing efficiency was calculated using the following equation:

$$1 - \frac{CFU_{cassette + engine}}{CFU_{engine}}$$

As seen in FIG. 20A, curing efficiency was well over 95% for each round.

Bulk Liquid Protocol: Four rounds of recursive editing and curing were performed using sugar editing gRNAs. Intended edits introduced a stop codon in three sugar genes (XylA-Y194*, LacZ-F593*, and GalK-E249*). These mutations cause a loss of function in the target gene. This loss of function phenotype can be observed by growing cells on MacConkey medium. The editing rate was determined by calculating the ratio of the number of cells with a loss of function mutation to the number of total cells. The fourth-round edit was YiaW_C183 and rate was determined by sampling colonies and Sanger sequencing 96 colonies at the edit loci. E. coli 181 strain cells comprising the engine vector depicted in FIG. 1C were made competent and transformed in a 100 µL volume with the editing vector depicted in FIG. 1C. The cells were allowed to recover for 3 hours in 3.0 mL total volume SOB medium. The recovered cells were then diluted 1:100 in 20 mL SOB medium containing chloramphenicol and the appropriate antibiotic for the editing vector (e.g., carbenicillin, kanamycin, nourseothricin N-acetyl transferase). The cells were then plated outgrown for 8 hours in SOB medium containing chloramphenicol and the antibiotic appropriate for the editing vector. Arabinose was added to the medium for a final concentration of 1%.

Figure 20B:
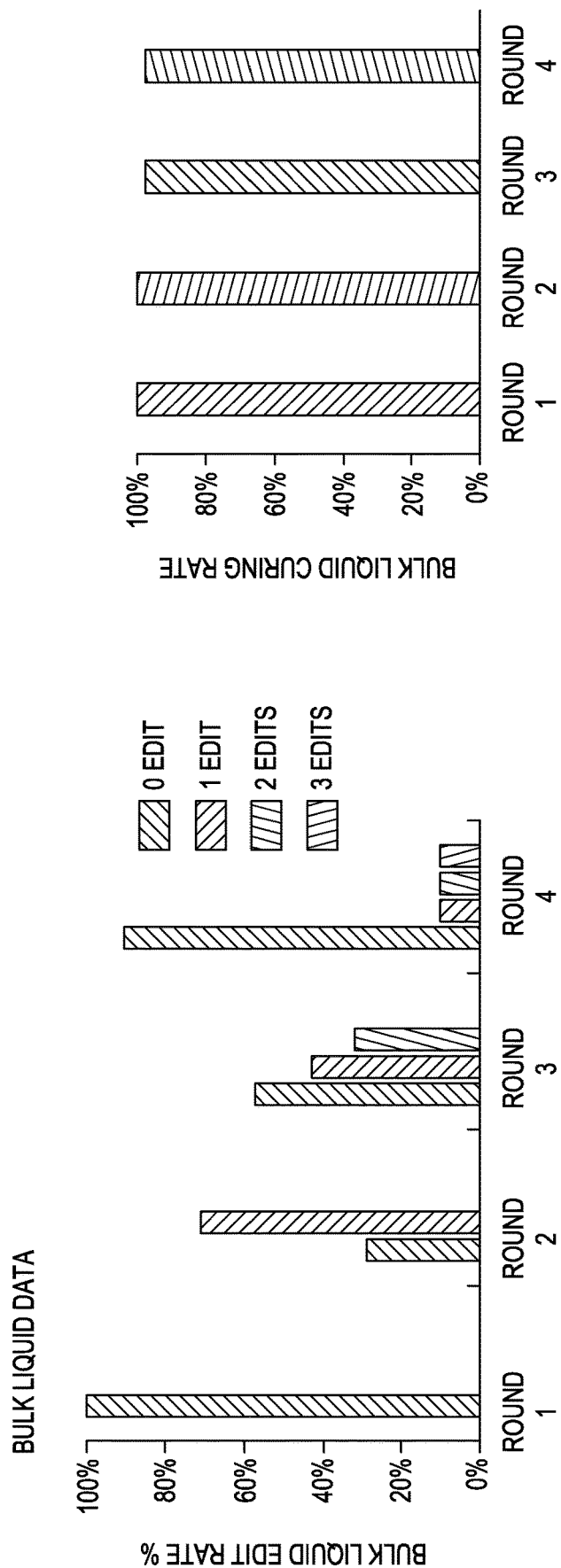

The cells were then grown for another hour at 30° C., grown for 2 hours at 42° C. to induce the pL promoter driving transcription of the nuclease and editing gRNA, then grown for another 9 hours at 30° C. The cells were then pelleted, washed 3', and resuspended in 20 mL SOB medium with chloramphenicol only. 12 mL of additional medium was added to 8 mL of the cells in suspension. Curing was induced (e.g., transcription of the nuclease and curing gRNA) by raising the temperature of the cell culture to 42° C. for 2 hours and by adding 20 µL DAPG to a final concentration of 25 µM. The cells were then grown at 30° C. for 6 hours to OD=2.5. Following curing, the cells were washed in LB+chlor medium, resuspended in LB+chlor medium and grown again at 30° C. to OD=0.5, and washed with 10% glycerol for another round of editing. The editing gRNAs and editing vector antibiotic resistance genes are listed in Table 3, and the results are shown in FIG. 20B. The succession of editing vectors comprised the same editing vector architecture as shown in at right in FIG. 1C; however, the editing gRNA/donor DNA and the selectable marker changed with each round.

For editing efficiency, note that after a first round of editing, 100% of cells had zero edits, which was expected since in the first round the editing vector did not comprise an editing gRNA or cellular target sequence; after a second round of editing approximately 30% of cells had zero edits, and approximately 70% of cells had one edit; and after a third round of editing, approximately 60% of cells had zero edits, approximately 40% of cells had one edit, approximately 30% of cells had two edits; and after a fourth round of editing, approximately 80% of cells had zero edits, and approximately 5% of cells had each of one, two or three edits. Note that these numbers are the fraction of cells that have at least 1, 2, or 3 edits; thus, if a cell has three edits it counts for each category, that is, it is the cumulative editing rate. The percentage curing achieved was over 95% after each round and was over 99% for the first two rounds.

TABLE 3

Bulk Liquid experimental description

| Round | 1 | 2 | 3 | 4 |
| --- | --- | --- | --- | --- |
| gRNA type | Non-editing | editing | editing | editing |
| Editing locus | None | XylA | GalK | LacZ |
| Editing vector Abx | Carb | Kan | Nat | Carb |

SWIIN Protocol: Four rounds of recursive editing and curing were performed using sugar editing gRNAs. Intended edits introduced a stop codon in three sugar genes (Xy1A-Y194*, LacZ-F593*, and GalK-E249*). These mutations caused a loss of function in the target gene. This loss of function phenotype can be observed by growing cells on MacConkey medium. The editing rate was determined by calculating the ratio of the number of cells with a loss of function mutation to the number of total cells. The fourth-round edit was YiaW_C183 and rate was determined by sampling colonies and Sanger sequencing 96 colonies at the edit loci. E. coli 181 strain cells comprising the engine vector depicted in FIG. 1C were made competent and transformed in a 100 µL volume with the editing vector depicted in FIG. 1C. The cells were allowed to recover for 3 hours in 2.7 mL SOB medium. The recovered cells were suspended in 10 mL and then loaded into a 200K SWIIN and grown for 8 hours in SOB medium containing chloramphenicol and the antibiotic appropriate for the editing vector. Medium exchange was performed with arabinose being added to the medium for a final concentration of 1%. The cells were then grown for another hour at 30° C., grown for 2.5 hours at 42° C. to induce the pL promoter driving transcription of the nuclease and editing gRNA, then grown for another 9 hours at 30° C. The cells were then recovered from the SWIIN, washed 3×, and resuspended in 20 mL SOB medium with chloramphenicol only. 12 mL of additional medium was added to 8 mL of the cells in suspension. The cells were grown to OD=3.0 and curing was induced (e.g., transcription of the curing gRNA and nuclease) by adding 20 µL DAPG to a final concentration of 25 µM and the temperature of the culture was increased to 42° C. for two hours.

Figure 20C:
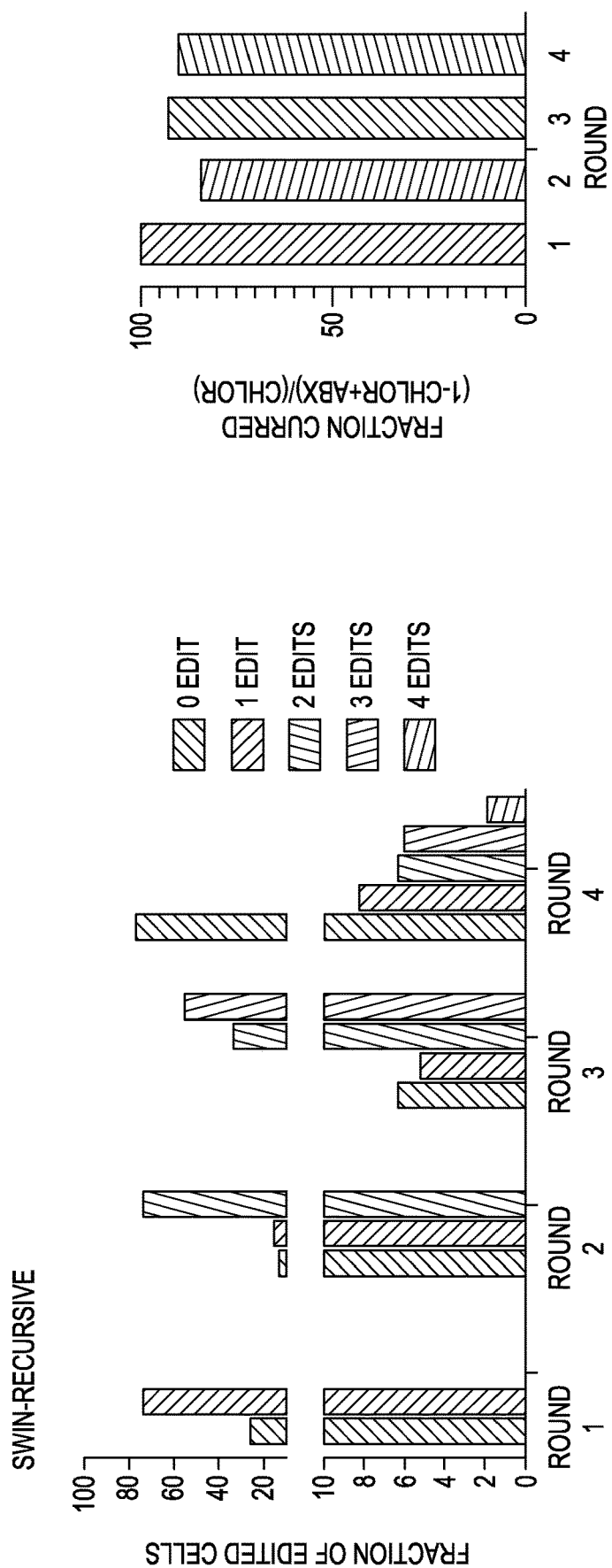

Following curing, the cells were washed in LB+chlor medium, resuspended in LB+chlor medium and grown again at 30° C. to OD=0.5 for another round of editing. The editing gRNAs and editing vector antibiotic resistance genes are listed in Table 4, and the results for curing and editing efficiency are shown in FIG. 20C. The succession of editing vectors comprised the same editing vector architecture as shown in at right in FIG. 1C; however, the editing gRNA/donor DNA and the selectable marker changed with each round. Editing on the SWIIN for the first round of editing resulted in approximately 20% of the cells having zero edits and 80% of the cells having one edit; for the second round of editing, approximately 20% of cells had zero edits, 20% had one edit, and 80% had two edits; for the third round of editing approximately 6% of the cells had zero edits, 4% had one edit, 40% had two edits, and 60% had three edits; finally after the fourth round of editing, approximately 80% of the cells had zero edits, 8% had one edit, 6% had two edits, and 2% had three edits. Note that these numbers are the fraction of cells that have at least 1, 2, or 3 edits; thus, if a cell has three edits it counts for each category, that is, it is the cumulative editing rate. All rounds of editing had a percentage of curing above 85%, and after rounds one and three, editing percentage was above 95%.

TABLE 4

SWIIN experimental description

| Round | 1 | 2 | 3 | 4 |
| --- | --- | --- | --- | --- |
| gRNA type | editing | editing | editing | editing |
| Editing locus | LacZ | GalK | XylA | yiaW |
| Editing vector Abx | Carb | Nat | Kan | Carb |

Example VII: Fully-Automated Singleplex RGN-Directed Editing Run

Singleplex automated genomic editing using MAD7 nuclease was successfully performed with an automated multi-module instrument of the disclosure. See U.S. Pat. No. 9,982,279; and U.S. Ser. Nos. 16/024,831 filed 30 Jun. 2018; 16/024,816 filed 30 Jun. 2018; 16/147,353 filed 28 Sep. 2018; 16/147,865 filed 30 Sep. 2018; and 16/147,871 filed 30 Jun. 2018.

An ampR plasmid backbone and a lacZ_F172* editing cassette were assembled via Gibson Assembly® into an "editing vector" in an isothermal nucleic acid assembly module included in the automated instrument. lacZ_F172 functionally knocks out the lacZ gene. "lacZ_F172*" indicates that the edit happens at the 172nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent E. coli cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module), and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on MacConkey agar base supplemented with lactose (as the sugar substrate), chloramphenicol and carbenicillin and grown until colonies appeared. White colonies represented functionally edited cells, purple colonies represented un-edited cells. All liquid transfers were performed by the automated liquid handling device of the automated multi-module cell processing instrument.

The result of the automated processing was that approximately $1.0E^{-03}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example VIII: Fully-Automated Recursive Editing Run

Recursive editing was successfully achieved using the automated multi-module cell processing system. An ampR plasmid backbone and a lacZ_V10* editing cassette were assembled via Gibson Assembly® into an "editing vector" in an isothermal nucleic acid assembly module included in the automated system. Similar to the lacZ_F172 edit, the lacZ_V10 edit functionally knocks out the lacZ gene. " lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent E. coli cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to OD600 of 2.7, then concentrated and rendered electrocompetent.

During cell growth, a second editing vector was prepared in the isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y154* cassette introduces a stop codon at the 154th amino acid reside, changing the tyrosine amino acid to a stop codon. This edit makes the galK gene product non-functional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent E. coli cells (that were transformed with and selected for the first editing vector) were transferred into a transformation module for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers were performed by the automated liquid handling device of the automated multi-module cell processing system.

In this recursive editing experiment, 41% of the colonies screened had both the lacZ and galK edits, the results of which were comparable to the double editing efficiencies obtained using a "benchtop" or manual approach.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶16.

We claim:

1. A method for curing cells of choice during recursive nucleic acid-directed nuclease editing comprising:
designing and synthesizing a first set of editing cassettes, wherein the first set of editing cassettes comprises one or more covalently-linked editing gRNA and donor DNA pairs, wherein each covalently-linked editing gRNA and donor DNA pair is under the control of a first inducible promoter;
assembling the first set of editing cassettes into a vector backbone thereby forming a first set of editing vectors, wherein the vector backbone comprises a first selectable marker, a curing gRNA under the control of a second inducible promoter, a nuclease under the control of a third inducible promoter; and a curing target sequence;
making cells of choice electrocompetent;
transforming the cells of choice with the first set of editing vectors to produce first transformed cells;
selecting for the first transformed cells via the first selectable marker thereby selecting for first selected cells;
inducing editing in the first selected cells by inducing the first and third inducible promoters thereby inducing transcription of the one or more covalently-linked editing gRNA and donor DNA pairs and the nuclease producing first edited cells;
curing the first set of editing vectors in the first edited cells by inducing the third and second inducible promoters thereby inducing transcription of the nuclease and curing gRNA which cuts the curing target sequence producing first cured cells;
growing the first cured cells;
rendering the first cured cells electrocompetent; and
transforming the first cured cells with a second set of editing vectors to produce second transformed cells, wherein the second set of editing vectors comprises editing cassettes each with one or more covalently-linked editing gRNA and donor DNA pairs under the control of the first inducible promoter; a second selectable marker; a curing gRNA under the control of the second inducible promoter; a nuclease under the control of the third inducible promoter; and the curing target sequence.

2. The method of claim 1, wherein the first inducible promoter and the third inducible promoters are the same inducible promoter.

3. The method of claim 1, wherein the first and third inducible promoters are pL promoters and either the first set of editing vectors comprises a c1857 gene under the control of a constitutive promoter.

4. The method of claim 1, wherein the curing target sequence is a pUC origin of replication.

5. The method of claim 4, wherein the curing gRNA is an anti-pUC origin gRNA.

6. The method of claim 1, wherein the second inducible promoter is a pPhlF promoter.

7. The method of claim 1, further comprising, after the second transforming step, the steps of:
selecting for the second transformed cells via the second selectable marker thereby selecting for second selected cells;
inducing editing in the second selected cells by inducing the first and third inducible promoters thereby inducing transcription of the one or more covalently-linked editing gRNA and donor DNA pairs and the nuclease producing second edited cells;
curing the second set of editing vectors in the second edited cells by inducing the third and second inducible promoters thereby inducing transcription of the nuclease and curing gRNA which cuts the curing target sequence producing second cured cells;
growing the second cured cells;
rendering the second cured cells electrocompetent; and
transforming the second cured cells with a third set of editing vectors to produce third transformed cells, wherein the third set of editing vectors comprises editing cassettes each with one or more covalently-linked editing gRNAs and donor DNA pairs under the control of the first inducible promoter; a third selectable marker; a curing gRNA under the control of the second inducible promoter; a nuclease under the control of the third inducible promoter; and the curing target sequence.

8. The method of claim 7, further comprising, after the third transforming step, the steps of:
selecting for the third transformed cells via the third selectable markers thereby selecting for third selected cells;
inducing editing in the third selected cells by inducing the first and third inducible promoters thereby inducing transcription of the one or more editing gRNA and donor DNA pairs and the nuclease producing third edited cells;
curing the third set of editing vectors in the third edited cells by inducing the third and second inducible promoters thereby inducing transcription of the nuclease and curing gRNA which cuts the curing target sequence producing third cured cells;
growing the third cured cells;
rendering the third cured cells electrocompetent; and
transforming the third cured cells with a fourth set of editing vectors to produce fourth transformed cells, wherein the fourth set of editing vectors comprises editing cassettes each with one or more covalently-linked editing gRNAs and donor DNA pairs under the control of the first inducible promoter; a fourth selectable marker; a curing gRNA under the control of the second inducible promoter; a nuclease under the control of the third inducible promoter; and the curing target sequence.

9. The method of claim 8, wherein the first, second, third and fourth sets of editing cassettes each comprises a library of editing gRNA and donor DNA pairs.

10. The method of claim 9, wherein each library of editing vectors comprises at least 1000 different editing gRNA and donor DNA pairs.

11. The method of claim 1, wherein the first and third inducible promoters are selected from a pL promoter, a pPhlF promoter, and a rhamnose inducible promoter.

12. The method of claim 1, further comprising after the inducing step and the curing step, a step of growing the first edited cells until the first edited cells reach a stationary phase of growth.

13. The method of claim 1, further comprising after the inducing step and the curing step, a step of growing the first edited cells until the first edited cells reach at least 60% of log phase growth.

14. The method of claim 13, further comprising after the inducing step and the curing step, a step of growing the first edited cells until the first edited cells reach at least 75% of log phase growth.

15. The method of claim 1, wherein the cells of choice are bacterial cells and the vector backbone further comprises a λ Red recombineering system.

16. The method of claim 1, wherein the cells of choice are yeast cells and the vector backbone is linear.

17. The method of claim 1, wherein the nuclease is MAD7.

18. The method of claim 1, further comprising between the transformation step and the inducing step, singulating the first transformed cells.

19. The method of claim 18, wherein the cells are singulated in a solid wall isolation incubation and normalization (SWIIN) module.

20. The method of claim 19, wherein the selecting, inducing, growing, and curing steps are performed in the SWIIN.

* * * * *